(12) United States Patent
Kohda

(10) Patent No.: US 7,189,577 B2
(45) Date of Patent: Mar. 13, 2007

(54) BIOCHEMICAL ANALYSIS KIT AND METHOD FOR EXPOSING STIMULABLE PHOSPHOR SHEET

(75) Inventor: Katsuhiro Kohda, Kanagawa (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 707 days.

(21) Appl. No.: 10/173,790

(22) Filed: Jun. 19, 2002

(65) Prior Publication Data
US 2006/0128026 A1   Jun. 15, 2006

(30) Foreign Application Priority Data
Jul. 2, 2001   (JP) .............................. 2001-201160

(51) Int. Cl.
*G01N 21/76*   (2006.01)
(52) U.S. Cl. .......................................... 436/172; 435/6
(58) Field of Classification Search ............... 436/172; 435/6
See application file for complete search history.

(56) References Cited
U.S. PATENT DOCUMENTS
2002/0119455 A1*   8/2002   Chan .............................. 435/6

* cited by examiner

*Primary Examiner*—Jill Warden
*Assistant Examiner*—Natalia Levkovich
(74) *Attorney, Agent, or Firm*—Sughrue Mion, PLLC

(57) ABSTRACT

A biochemical analysis kit includes a biochemical analysis unit including a substrate capable of attenuating radiation energy and light energy and formed with a plurality of absorptive regions to be spaced apart from each other, and a stimulable phosphor sheet including a support formed with a plurality of stimulable phosphor layer regions in substantially the same pattern as that of the plurality of absorptive regions, the plurality of absorptive regions of the biochemical analysis unit and the plurality of stimulable phosphor layer regions of the stimulable phosphor sheet being formed so that an average area Sm of the plurality of absorptive regions of the biochemical analysis unit and an average area Sp of the plurality of stimulable phosphor layer regions of the stimulable phosphor sheet meet a requirement that Sp is equal to or larger than a quarter of Sm. According to the thus constituted biochemical analysis kit, it is possible to produce biochemical analysis data having excellent quantitative characteristics with high resolution by reading radiation data or chemiluminescence data transferred from the biochemical analysis unit to the stimulable phosphor sheet.

38 Claims, 15 Drawing Sheets

BIOCHEMICAL ANALYSIS KIT AND METHOD FOR EXPOSING STIMULABLE PHOSPHOR SHEET

BACKGROUND OF THE INVENTION

The present invention relates to a biochemical analysis kit and a method for exposing a stimulable phosphor sheet and, particularly, to a biochemical analysis kit and a method for exposing a stimulable phosphor sheet which can prevent noise caused by the scattering of electron beams (β rays) released from a radioactive labeling substance selectively contained in a plurality of spot-like regions of a biochemical analysis unit from being generated in biochemical analysis data and produce biochemical analysis data having an excellent quantitative characteristic by reading radiation data with high resolution even in the case of forming a plurality of spot-like regions containing specific binding substances, which can specifically bind with a substance derived from a living organism and whose sequence, base length, composition and the like are known, in the biochemical analysis unit at a high density, selectively labeling the plurality of spot-like regions of the biochemical analysis unit with a radioactive labeling substance to record radiation data therein, facing the thus prepared biochemical analysis unit toward a stimulable phosphor layer of a stimulable phosphor sheet to expose the stimulable phosphor layer to the radioactive labeling substance, irradiating the thus exposed stimulable phosphor layer with a stimulating ray, and photoelectrically detecting stimulated emission released from the stimulable phosphor layer to produce biochemical analysis data, and can also prevent noise caused by the scattering of chemiluminescence emission selectively released from a plurality of spot-like regions of a biochemical analysis unit from being generated in biochemical analysis data and produce biochemical analysis data having an excellent quantitative characteristic by reading radiation data with high resolution even in the case of forming a plurality of spot-like regions containing specific binding substances, which can specifically bind with a substance derived from a living organism and whose sequence, base length, composition and the like are known, in the biochemical analysis unit at a high density, selectively labeling the plurality of spot-like regions of the biochemical analysis unit with a labeling substance which generates chemiluminescence emission when it contacts a chemiluminescent substrate to record chemiluminescence data therein, bringing the plurality of spot-like regions of the biochemical analysis unit into contact with a chemiluminescent substrate, thereby causing the plurality of spot-like regions of the biochemical analysis unit to release chemiluminescence emission, facing the biochemical analysis unit releasing chemiluminescence emission toward a stimulable phosphor layer of a stimulable phosphor sheet to expose the stimulable phosphor layer to chemiluminescence emission, irradiating the thus exposed stimulable phosphor layer with a stimulating ray, and photoelectrically detecting stimulated emission released from the stimulable phosphor layer to produce biochemical analysis data.

DESCRIPTION OF THE PRIOR ART

An autoradiographic analyzing system using as a detecting material for detecting radiation a stimulable phosphor which can absorb, store and record the energy of radiation when it is irradiated with radiation and which, when it is then stimulated by an electromagnetic wave having a specified wavelength, can release stimulated emission whose light amount corresponds to the amount of radiation with which it was irradiated is known, which comprises the steps of introducing a radioactively labeled substance into an organism, using the organism or a part of the tissue of the organism as a specimen, superposing the specimen and a stimulable phosphor sheet formed with a stimulable phosphor layer for a certain period of time, storing and recording radiation energy in a stimulable phosphor contained in the stimulable phosphor layer, scanning the stimulable phosphor layer with an electromagnetic wave to excite the stimulable phosphor, photoelectrically detecting the stimulated emission released from the stimulable phosphor to produce digital image signals, effecting image processing on the obtained digital image signals, and reproducing an image on displaying means such as a CRT or the like or a photographic film (see, for example, Japanese Patent Publication No. 1-60784, Japanese Patent Publication No. 1-60782, Japanese Patent Publication No. 4-3952 and the like).

There is further known chemiluminescence analysis system comprising the steps of employing, as a detecting material for light, a stimulable phosphor which can absorb and store the energy of light upon being irradiated therewith and release a stimulated emission whose amount is proportional to that of the received light upon being stimulated with an electromagnetic wave having a specific wavelength range, selectively labeling a fixed high molecular substance such as a protein or a nucleic acid sequence with a labeling substance which generates chemiluminescence emission when it contacts a chemiluminescent substance, contacting the high molecular substance selectively labeled with the labeling substance and the chemiluminescent substance, storing and recording the chemiluminescence emission in the wavelength of visible light generated by the contact of the chemiluminescent substance and the labeling substance in the stimulable phosphor contained in a stimulable phosphor layer formed on a stimulable phosphor sheet, scanning the stimulable phosphor layer with an electromagnetic wave to excite the stimulable phosphor, photoelectrically detecting the stimulated emission released from the stimulable phosphor to produce digital signals, effecting data processing on the obtained digital signals, and reproducing data on displaying means such as a CRT or a recording material such as a photographic film (see for example, U.S. Pat. No. 5,028,793, UK Patent Application 2,246,197 A and the like).

Unlike the system using a photographic film, according to these systems using the stimulable phosphor as a detecting material, development, which is chemical processing, becomes unnecessary. Further, it is possible reproduce a desired image by effecting image processing on the obtained image data and effect quantitative analysis using a computer. Use of a stimulable phosphor in these processes is therefore advantageous.

On the other hand, a fluorescence analyzing system using a fluorescent substance as a labeling substance instead of a radioactive labeling substance in the autoradiographic analyzing system is known. According to this system, it is possible to study a genetic sequence, study the expression level of a gene, and to effect separation or identification of protein or estimation of the molecular weight or properties of protein or the like. For example, this system can perform a process including the steps of distributing a plurality of DNA fragments on a gel support by means of electrophoresis after a fluorescent dye was added to a solution containing a plurality of DNA fragments to be distributed, or distributing a plurality of DNA fragments on a gel support containing a fluorescent dye, or dipping a gel support on which a plurality of DNA fragments have been distributed by means of electrophoresis in a solution containing a fluorescent dye, thereby labeling the electrophoresed DNA fragments, exciting the fluorescent dye by a stimulating ray to cause it to release fluorescence emission, detecting the released fluorescence emission to produce an image and detecting the distribution of the DNA fragments on the gel support. This system can also perform a process including the steps of distributing a plurality of DNA fragments on a gel support by means of electrophoresis, denaturing the DNA fragments, transferring at least a part of the denatured DNA fragments onto a transfer support such as a nitrocellulose support by the Southern-blotting method, hybridizing a probe prepared by labeling target DNA and DNA or RNA complementary thereto with the denatured DNA fragments, thereby selectively labeling only the DNA fragments complementary to the probe DNA or probe RNA, exciting the fluorescent dye by a stimulating ray to cause it to release fluorescence emission, detecting the released fluorescence emission to produce an image and detecting the distribution of the target DNA on the transfer support. This system can further perform a process including the steps of preparing a DNA probe complementary to DNA containing a target gene labeled by a labeling substance, hybridizing it with DNA on a transfer support, combining an enzyme with the complementary DNA labeled by a labeling substance, causing the enzyme to contact a fluorescent substance, transforming the fluorescent substance to a fluorescent substance having fluorescence emission releasing property, exciting the thus produced fluorescent substance by a stimulating ray to release fluorescence emission, detecting the fluorescence emission to produce an image and detecting the distribution of the target DNA on the transfer support. This fluorescence detecting system is advantageous in that a genetic sequence or the like can be easily detected without using a radioactive substance.

Similarly, there is known a chemiluminescence detecting system comprising the steps of fixing a substance derived from a living organism such as a protein or a nucleic acid sequence on a support, selectively labeling the substance derived from a living organism with a labeling substance which generates chemiluminescence emission when it contacts a chemiluminescent substrate, contacting the substance derived from a living organism and selectively labeled with the labeling substance and the chemiluminescent substrate, photoelectrically detecting the chemiluminescence emission in the wavelength of visible light generated by the contact of the chemiluminescent substrate and the labeling substance to produce digital image signals, effecting image processing thereon, and reproducing a chemiluminescent image on a display means such as a CRT or a recording material such as a photographic film, thereby obtaining information relating to the high molecular substance such as genetic information Further, a micro-array analyzing system has been recently developed, which comprises the steps of using a spotting device to drop at different positions on the surface of a carrier such as a slide glass plate, a membrane filter or the like specific binding substances which can specifically bind with a substance derived from a living organism such as a cell, virus, hormone, tumor marker, enzyme, antibody, antigen, abzyme, other protein, a nuclear acid, cDNA, DNA, RNA or the like and whose sequence, base length, composition and the like are known, thereby forming a number of independent spots, specifically binding the specific binding substances using a hybridization method or the like with a substance derived from a living organism such as a cell, virus, hormone, tumor marker, enzyme, antibody, antigen, abzyme, other protein, a nuclear acid, cDNA, DNA or mRNA by extraction, isolation or the like and optionally further subjected to chemical processing, chemical modification or the like and which is labeled with a labeling substance such as a fluorescent substance, dye or the like, thereby forming a micro-array, irradiating the micro-array with a stimulating ray, photoelectrically detecting light such as fluorescence emission released from a labeling substance such as a fluorescent substance, dye or the like, and analyzing the substance derived from a living organism. This micro-array analyzing system is advantageous in that a substance derived from a living organism can be analyzed in a short time period by forming a number of spots of specific binding substances at different positions of the surface of a carrier such as a slide glass plate at a high density and hybridizing them with a substance derived from a living organism and labeled with a labeling substance.

In addition, a macro-array analyzing system using a radioactive labeling substance as a labeling substance has been further developed, which comprises the steps of using a spotting device to drop at different positions on the surface of a carrier such as a membrane filter or the like specific binding substances which can specifically bind with a substance derived from a living organism such as a cell, virus, hormone, tumor marker, enzyme, antibody, antigen, abzyme, other protein, a nuclear acid, cDNA, DNA, RNA or the like and whose sequence, base length, composition and the like are known, thereby forming a number of independent spots, specifically binding the specific binding substance using a hybridization method or the like with a substance derived from a living organism such as a cell, virus, hormone, tumor marker, enzyme, antibody, antigen, abzyme, other protein, a nuclear acid, cDNA, DNA or mRNA by extraction, isolation or the like and optionally further subjected to chemical processing, chemical modification or the like and which is labeled with a radioactive labeling substance, thereby forming a macro-array, superposing the macro-array and a stimulable phosphor sheet formed with a stimulable phosphor layer, exposing the stimulable phosphor layer to the radioactive labeling substance, irradiating the stimulable phosphor layer with a stimulating ray to excite the stimulable phosphor, photoelectrically detecting the stimulated emission released from the stimulable phosphor to produce biochemical analysis data, and analyzing the substance derived from a living organism.

However, in the macro-array analyzing system using a radioactive labeling substance as a labeling substance, when the stimulable phosphor layer is exposed to a radioactive labeling substance, since the radiation energy of the radioactive labeling substance contained in spot-like regions formed on the surface of a carrier such as a membrane filter is very large, electron beams (β rays) released from the radioactive labeling substance contained in the individual spot-like regions are scattered in the carrier such as a membrane filter, thereby impinging on regions of the stimulable phosphor layer that should be exposed only to the radioactive labeling substance contained in neighboring spot-like regions, or electron beams released from the radioactive labeling substance adhering to the surface of the carrier such as a membrane filter between neighboring spot-like regions impinge on the stimulable phosphor layer, to generate noise in biochemical analysis data produced by photoelectrically detecting stimulated emission, thus making data of neighboring spot-like regions hard to separate and lowering resolution, and to lower the accuracy of biochemical analysis when a substance derived from a living organism is analyzed by quantifying the radiation amount of each spot. The degradation of the resolution and accuracy of biochemical analysis is particularly pronounced when spots are formed close to each other at a high density.

In order to solve these problems by preventing noise caused by the scattering of electron beams released from radioactive labeling substance contained in neighboring spot-like regions, it is inevitably required to increase the distance between neighboring spot-like regions and this makes the density of the spot-like regions lower and the test efficiency lower.

Furthermore, in the field of biochemical analysis, it is often required to analyze a substance derived from a living organism by forming at different positions on the surface of a carrier such as a membrane filter or the like a plurality of spot-like regions containing specific binding substances which can specifically bind with a substance derived from a living organism such as a cell, virus, hormone, tumor marker, enzyme, antibody, antigen, abzyme, other protein, a nuclear acid, cDNA, DNA, RNA or the like and whose sequence, base length, composition and the like are known, specifically binding, using a hybridization method or the like, the specific binding substances contained in the plurality of spot-like regions with a substance derived from a living organism labeled with a labeling substance which generates chemiluminescence emission when it contacts a chemiluminescent substrate, thereby selectively labeling the plurality of spot-like regions, causing the plurality of spot-like regions to come into contact with a chemiluminescent substrate, exposing the stimulable phosphor layer of a stimulable phosphor sheet to chemiluminescence emission in the wavelength of visible light generated by the contact of the chemiluminescent substrate and the labeling substance, thereby storing the energy of chemiluminescence emission in the stimulable phosphor layer, irradiating the stimulable phosphor layer with a stimulating ray, and photoelectrically detecting stimulated emission released from the stimulable phosphor layer, thereby effecting biochemical analysis. In this case, chemiluminescence emission released from any particular spot-like region is scattered in the carrier such as a membrane filter, thereby impinging on regions of the stimulable phosphor layer that should be exposed only to the chemiluminescence emission released from neighboring spot-like regions to generate noise in biochemical analysis data produced by photoelectrically detecting stimulated emission, thus making data of neighboring spot-like regions hard to separate and lowering resolution, and to lower the quantitative characteristics of biochemical analysis data.

SUMMARY OF THE INVENTION

It is therefore an object of the present invention to provide a biochemical analysis kit and a method for exposing a stimulable phosphor sheet which can prevent noise caused by the scattering of electron beams (β rays) released from a radioactive labeling substance selectively contained in a plurality of spot-like regions of a biochemical analysis unit from being generated in biochemical analysis data and produce biochemical analysis data having an excellent quantitative characteristic by reading radiation data with high resolution even in the case of forming a plurality of spot-like regions containing specific binding substances, which can specifically bind with a substance derived from a living organism and whose sequence, base length, composition and the like are known, in the biochemical analysis unit at a high density, selectively labeling the plurality of spot-like regions of the biochemical analysis unit with a radioactive labeling substance to record radiation data therein, facing the thus prepared biochemical analysis unit toward a stimulable phosphor layer of a stimulable phosphor sheet to expose the stimulable phosphor layer to a radioactive labeling substance, irradiating the thus exposed stimulable phosphor layer with a stimulating ray, and photoelectrically detecting stimulated emission released from the stimulable phosphor layer to produce biochemical analysis data, and can also prevent noise caused by the scattering of chemiluminescence emission selectively released from a plurality of spot-like regions of a biochemical analysis unit from being generated in biochemical analysis data and produce biochemical analysis data having an excellent quantitative characteristic by reading radiation data with high resolution even in the case of forming a plurality of spot-like regions containing specific binding substances, which can specifically bind with a substance derived from a living organism and whose sequence, base length, composition and the like are known, in the biochemical analysis unit at a high density, selectively labeling the plurality of spot-like regions of the biochemical analysis unit with a labeling substance which generates chemiluminescence emission when it contacts a chemiluminescent substrate to record chemiluminescence data therein, bringing the plurality of spot-like regions of the biochemical analysis unit into contact with a chemiluminescent substrate, thereby causing the plurality of spot-like regions of the biochemical analysis unit to release chemiluminescence emission, facing the biochemical analysis unit releasing chemiluminescence emission toward a stimulable phosphor layer of a stimulable phosphor sheet to expose the stimulable phosphor layer to chemiluminescence emission, irradiating the thus exposed stimulable phosphor layer with a stimulating ray, and photoelectrically detecting stimulated emission released from the stimulable phosphor layer to produce biochemical analysis data.

The above and other objects of the present invention can be accomplished by a biochemical analysis kit comprising a biochemical analysis unit including a substrate capable of attenuating radiation energy and/or light energy and formed with a plurality of absorptive regions to be spaced apart from each other, and a stimulable phosphor sheet including a support formed with a plurality of stimulable phosphor layer regions to be spaced apart from each other in substantially the same pattern as that of the plurality of absorptive regions formed in the substrate of the biochemical analysis unit, the plurality of absorptive regions of the biochemical analysis unit and the plurality of stimulable phosphor layer regions of the stimulable phosphor sheet being formed so that an average area Sm of the plurality of absorptive regions of the biochemical analysis unit and an average area Sp of the plurality of stimulable phosphor layer regions of the stimulable phosphor sheet meet a requirement that Sp is equal to or larger than a quarter of Sm.

According to the present invention, even in the case of forming a plurality of absorptive regions in a biochemical analysis unit at a high density, spotting a solution containing specific binding substances whose sequence, base length, composition and the like are known onto the plurality of absorptive regions of the biochemical analysis unit, thereby absorbing the specific binding substances in the plurality of absorptive regions, specifically binding the specific binding substances absorbed in the plurality of absorptive regions with a substance derived from a living organism and labeled with a radioactive labeling substance by means of hybridization or the like, thereby selective labeling the plurality of absorptive regions of the biochemical analysis unit with the radioactive labeling substance and recording radiation data therein, superposing a stimulable phosphor sheet formed with a plurality of stimulable phosphor layer regions on the thus prepared biochemical analysis unit, exposing the plurality of stimulable phosphor layer regions of the stimulable phosphor sheet to the radioactive labeling substance selectively contained in the plurality of absorptive regions of the biochemical analysis unit, irradiating the plurality of stimulable phosphor layer regions of the stimulable phosphor sheet with a stimulating ray, and photoelectrically detecting stimulated emission released from the plurality of stimulable phosphor layer regions of the stimulable phosphor sheet to produce biochemical analysis data, since the plurality of stimulable phosphor layer regions are formed in the support of the stimulable phosphor sheet in substantially the same pattern as that of the plurality of absorptive regions formed in the substrate of the biochemical analysis unit and the substrate of the biochemical analysis unit substrate of the biochemical analysis unit is capable of attenuating radiation energy, electron beams (β rays) released from the radioactive labeling substance contained in the individual absorptive regions of the biochemical analysis unit can be effectively prevented from scattering in the substrate of the biochemical analysis unit and entering stimulable phosphor layer regions other than that to be exposed to electron beams (β rays) released from the radioactive labeling substance contained in the absorptive region and, therefore, it is possible to produce biochemical analysis data having an excellent quantitative characteristic with high resolution by scanning the plurality of the thus exposed stimulable phosphor layer regions with a stimulating ray and photoelectrically detecting stimulated emission released from the plurality of stimulable phosphor layer regions.

Further, even in the case where the substrate of the biochemical analysis unit is capable of attenuating radiation energy, when each of the stimulable phosphor layer regions is formed in the surface of the stimulable phosphor sheet so as to have a much smaller area than that of the corresponding absorptive regions formed in the substrate of the biochemical analysis unit, some electron beams (β rays) released from the radioactive labeling substance contained in a particular absorptive region of the biochemical analysis unit do not enter the corresponding stimulable phosphor layer region but enter stimulable phosphor layer regions next to the corresponding stimulable phosphor layer region and, therefore, there is some risk of lowering the quantitative characteristic of biochemical analysis data produced by scanning the plurality of the thus exposed stimulable phosphor layer regions with a stimulating ray and photoelectrically detecting stimulated emission released from the plurality of stimulable phosphor layer regions. However, according to the present invention, since the plurality of absorptive regions of the biochemical analysis unit and the plurality of stimulable phosphor layer regions of the stimulable phosphor sheet are formed so that the average area $S_m$ of the plurality of absorptive regions of the biochemical analysis unit and the average area $S_p$ of the plurality of stimulable phosphor layer regions off the stimulable phosphor sheet meet the requirement that $S_p$ is equal to or larger than a quarter of $S_m$, electron beams (β rays) released from the radioactive labeling substance contained in the individual absorptive regions of the biochemical analysis unit can be effectively prevented from entering stimulable phosphor layer regions next to the corresponding stimulable phosphor layer region and, therefore, it is possible to produce biochemical analysis data having an excellent quantitative characteristic with high resolution by scanning the plurality of the thus exposed stimulable phosphor layer regions with a stimulating ray and photoelectrically detecting stimulated emission released from the plurality of stimulable phosphor layer regions.

To the contrary, it has been ascertained that in the case where the average area $S_p$ of the plurality of stimulable phosphor layer regions formed in the support of the stimulable phosphor sheet is smaller than a quarter of the average area $S_m$ of the plurality of absorptive regions formed in the substrate of the biochemical analysis unit, since electron beams (β rays) released from a particular absorptive region cannot be prevented from entering stimulable phosphor layer regions next to the corresponding stimulable phosphor layer region, the quantitative characteristic of biochemical analysis data the quantitative characteristic of biochemical analysis data is markedly lowered and this cannot be ignored.

On the other hand, according to the present invention, even in the case of forming a plurality of absorptive regions in a biochemical analysis unit at a high density, spotting a solution containing specific binding substances whose sequence, base length, composition and the like are known onto the plurality of absorptive regions of the biochemical analysis unit, thereby absorbing the specific binding substances in the plurality of absorptive regions, specifically binding, by means of hybridization or the like, the specific binding substances absorbed in the plurality of absorptive regions with a substance derived from a living organism and labeled with a labeling substance which generates chemiluminescence emission when it contacts a chemiluminescent substrate, thereby selective labeling the plurality of absorptive regions of the biochemical analysis unit with the labeling substance which generates chemiluminescence emission when it contacts a chemiluminescent substrate and recording chemiluminescence data therein, bringing the thus prepared biochemical analysis unit into contact with a chemiluminescent substrate, thereby causing the plurality of absorptive regions of the biochemical analysis unit to release chemiluminescence emission, superposing a stimulable phosphor sheet formed with a plurality of stimulable phosphor layer regions on the biochemical analysis unit releasing chemiluminescence emission, exposing the plurality of stimulable phosphor layer regions of the stimulable phosphor sheet to chemiluminescence emission selectively released from the plurality of absorptive regions of the biochemical analysis unit, irradiating the plurality of stimulable phosphor layer regions of the stimulable phosphor sheet with a stimulating ray, and photoelectrically detecting stimulated emission released from the plurality of stimulable phosphor layer regions of the stimulable phosphor sheet to produce biochemical analysis data, since the plurality of stimulable phosphor layer regions are formed in the support of the stimulable phosphor sheet in substantially the same pattern as that of the plurality of absorptive regions formed in the substrate of the biochemical analysis unit and the substrate of the biochemical analysis unit substrate of the biochemical analysis unit is capable of attenuating light energy, chemiluminescence emission released from the individual absorptive regions of the biochemical analysis unit can be effectively prevented from scattering in the substrate of the biochemical analysis unit and entering stimulable phosphor layer regions other than that to be exposed to chemiluminescence emission released from the absorptive region and, therefore, it is possible to produce biochemical analysis data having an excellent quantitative characteristic with high resolution by scanning the plurality of the thus exposed stimulable phosphor layer regions with a stimulating ray and photoelectrically detecting stimulated emission released from the plurality of stimulable phosphor layer regions.

Further, even in the case where the substrate of the biochemical analysis unit is capable of attenuating light energy, when each of the stimulable phosphor layer regions is formed in the surface of the stimulable phosphor sheet so as to have a much smaller area than that of the corresponding absorptive regions formed in the substrate of the biochemical analysis unit, some chemiluminescence emission released from a particular absorptive region of the biochemical analysis unit does not enter the corresponding stimulable phosphor layer region but enters stimulable phosphor layer regions next to the corresponding stimulable phosphor layer region and, therefore, there is some risk of lowering the quantitative characteristic of biochemical analysis data produced by scanning the plurality of the thus exposed stimulable phosphor layer regions with a stimulating ray and photoelectrically detecting stimulated emission released from the plurality of stimulable phosphor layer regions. However, according to the present invention, since the plurality of absorptive regions of the biochemical analysis unit and the plurality of stimulable phosphor layer regions of the stimulable phosphor sheet are formed so that the average area Sm of the plurality of absorptive regions of the biochemical analysis unit and the average area Sp of the plurality of stimulable phosphor layer regions off the stimulable phosphor sheet meet the requirement that Sp is equal to or larger than a quarter of Sm, chemiluminescence emission released from the individual absorptive regions of the biochemical analysis unit can be effectively prevented from entering stimulable phosphor layer regions next to the corresponding stimulable phosphor layer region and, therefore, it is possible to produce biochemical analysis data having an excellent quantitative characteristic with high resolution by scanning the plurality of the thus exposed stimulable phosphor layer regions with a stimulating ray and photoelectrically detecting stimulated emission released from the plurality of stimulable phosphor layer regions.

To the contrary, it has been ascertained that in the case where the average area Sp of the plurality of stimulable phosphor layer regions formed in the support of the stimulable phosphor sheet is smaller than a quarter of the average area Sm of the plurality of absorptive regions formed in the substrate of the biochemical analysis unit, since some chemiluminescence emission released from a particular absorptive region cannot be prevented from entering stimulable phosphor layer regions next to the corresponding stimulable phosphor layer region, the quantitative characteristic of biochemical analysis data the quantitative characteristic of biochemical analysis data is markedly lowered and this cannot be ignored.

In the present invention, the case where a plurality of absorptive regions are selectively labeled with a labeling substance which generates chemiluminescence emission when it contacts a chemiluminescent substrate as termed herein includes the case where a plurality of absorptive regions are selectively labeled with a labeling substance which generates chemiluminescence emission when it contacts a chemiluminescent substrate by selectively binding a substance derived from a living organism and labeled with a labeling substance which generates chemiluminescence emission when it contacts a chemiluminescent substrate and the case where a plurality of absorptive regions are selectively labeled with a labeling substance which generates chemiluminescence emission when it contacts a chemiluminescent substrate by selectively binding a substance derived from a living organism and labeled with a hapten, and binding an antibody for the hapten labeled with an enzyme which generates chemiluminescence emission when it contacts a chemiluminescent substrate with the hapten by an antigen-antibody reaction.

In the present invention, illustrative examples of the combination of hapten and antibody include digoxigenin and anti-digoxigenin antibody, theophylline and anti-theophylline antibody, fluorosein and anti-fluorosein antibody, and the like. Further, the combination of biotin and avidin, antigen and antibody may be utilized instead of the combination of hapten and antibody.

In a preferred aspect of the present invention, the plurality of absorptive regions of the biochemical analysis unit and the plurality of stimulable phosphor layer regions of the stimulable phosphor sheet are formed so that an average area Sm of the plurality of absorptive regions of the biochemical analysis unit and an average area Sp of the plurality of stimulable phosphor layer regions off the stimulable phosphor sheet meet a requirement that Sp is equal to or larger than a half of Sm.

According to this preferred aspect of the present invention, since the plurality of absorptive regions of the biochemical analysis unit and the plurality of stimulable phosphor layer regions of the stimulable phosphor sheet are formed so that the average area Sm of the plurality of absorptive regions of the biochemical analysis unit and the average area Sp of the plurality of stimulable phosphor layer regions of the stimulable phosphor sheet meet the requirement that Sp is equal to or larger than a half of Sm, electron beams ($\beta$ rays) released from the radioactive labeling substance contained in a particular absorptive region of the biochemical analysis unit can be more effectively prevented from entering stimulable phosphor layer regions next to the corresponding stimulable phosphor layer region and, therefore, it is possible to produce biochemical analysis data having an excellent quantitative characteristic with high resolution.

Further, according to this preferred aspect of the present invention, since the plurality of absorptive regions of the biochemical analysis unit and the plurality of stimulable phosphor layer regions of the stimulable phosphor sheet are formed so that the average area Sm of the plurality of absorptive regions of the biochemical analysis unit and the average area Sp of the plurality of stimulable phosphor layer regions of the stimulable phosphor sheet meet a requirement that Sp is equal to or larger than a half of Sm, chemiluminescence emission released from a particular absorptive region of the biochemical analysis unit can be more effectively prevented from entering stimulable phosphor layer regions next to the corresponding stimulable phosphor layer region and, therefore, it is possible to produce biochemical analysis data having an excellent quantitative characteristic with high resolution.

In a further preferred aspect of the present invention, the plurality of absorptive regions of the biochemical analysis unit and the plurality of stimulable phosphor layer regions of the stimulable phosphor sheet are formed so that an average area Sm of the plurality of absorptive regions of the biochemical analysis unit and an average area Sp of the plurality of stimulable phosphor layer regions of the stimulable phosphor sheet meet a requirement that Sp is equal to or larger than Sm.

According to this preferred aspect of the present invention, since the plurality of absorptive regions of the biochemical analysis unit and the plurality of stimulable phosphor layer regions of the stimulable phosphor sheet are formed so that the average area Sm of the plurality of absorptive regions of the biochemical analysis unit and the average area Sp of the plurality of stimulable phosphor layer regions of the stimulable phosphor sheet meet the requirement that Sp is equal to or larger than Sm, electron beams (β rays) released from the radioactive labeling substance contained in a particular absorptive region of the biochemical analysis unit can be much more effectively prevented from entering stimulable phosphor layer regions next to the corresponding stimulable phosphor layer region and, therefore, it is possible to produce biochemical analysis data having an excellent quantitative characteristic with high resolution.

Further, according to this preferred aspect of the present invention, since the plurality of absorptive regions of the biochemical analysis unit and the plurality of stimulable phosphor layer regions of the stimulable phosphor sheet are formed so that the average area Sm of the plurality of absorptive regions of the biochemical analysis unit and the average area Sp of the plurality of stimulable phosphor layer regions of the stimulable phosphor sheet meet the requirement that Sp is equal to or larger than Sm, chemiluminescence emission released from a particular absorptive region of the biochemical analysis unit can be much more effectively prevented from entering stimulable phosphor layer regions next to the corresponding stimulable phosphor layer region and, therefore, it is possible to produce biochemical analysis data having an excellent quantitative characteristic with high resolution.

In a preferred aspect of the present invention, the plurality of absorptive regions of the biochemical analysis unit and the plurality of stimulable phosphor layer regions of the stimulable phosphor sheet are formed substantially circular so that an average diameter Dm of the plurality of absorptive regions of the biochemical analysis unit and an average diameter Dp of the plurality of stimulable phosphor layer regions of the stimulable phosphor sheet meet a requirement that Dp is equal to or larger than a half of Dm.

In a further preferred aspect of the present invention, the plurality of absorptive regions of the biochemical analysis unit and the plurality of stimulable phosphor layer regions of the stimulable phosphor sheet are formed substantially circular so that an average diameter Dm of the plurality of absorptive regions of the biochemical analysis unit and an average diameter Dp of the plurality of stimulable phosphor layer regions of the stimulable phosphor sheet meet a requirement that Dp is equal to or larger than $Dm^{1/2}$.

In a further preferred aspect of the present invention, the plurality of absorptive regions of the biochemical analysis unit and the plurality of stimulable phosphor layer regions of the stimulable phosphor sheet are formed substantially circular so that an average diameter Dm of the plurality of absorptive regions of the biochemical analysis unit and an average diameter Dp of the plurality of stimulable phosphor layer regions of the stimulable phosphor sheet meet a requirement that Dp is equal to or larger than Dm.

In a preferred aspect of the present invention, the substrate of the biochemical analysis unit is formed with 10 or more absorptive regions.

In a further preferred aspect of the present invention, the substrate of the biochemical analysis unit is formed with 50 or more absorptive regions.

In a further preferred aspect of the present invention, the substrate of the biochemical analysis unit is formed with 100 or more absorptive regions.

In a further preferred aspect of the present invention, the substrate of the biochemical analysis unit is formed with 500 or more absorptive regions.

In a further preferred aspect of the present invention, the substrate of the biochemical analysis unit is formed with 1,000 or more absorptive regions.

In a further preferred aspect of the present invention, the substrate of the biochemical analysis unit is formed with 5,000 or more absorptive regions.

In a further preferred aspect of the present invention, the substrate of the biochemical analysis unit is formed with 10,000 or more absorptive regions.

In a further preferred aspect of the present invention, the substrate of the biochemical analysis unit is formed with 50,000 or more absorptive regions.

In a further preferred aspect of the present invention, the substrate of the biochemical analysis unit is formed with 100,000 or more absorptive regions.

In a preferred aspect of the present invention, each of the plurality of absorptive regions formed in the substrate of the biochemical analysis unit has a size of less than 5 $mm^2$.

In a further preferred aspect of the present invention, each of the plurality of absorptive regions formed in the substrate of the biochemical analysis unit has a size of less than 1 $mm^2$.

In a further preferred aspect of the present invention, each of the plurality of absorptive regions formed in the substrate of the biochemical analysis unit has a size of less than 0.5 $mm^2$.

In a further preferred aspect of the present invention, each of the plurality of absorptive regions formed in the substrate of the biochemical analysis unit has a size of less than 0.1 $mm^2$.

In a further preferred aspect of the present invention, each of the plurality of absorptive regions formed in the substrate of the biochemical analysis unit has a size of less than 0.05 $mm^2$.

In a further preferred aspect of the present invention, each of the plurality of absorptive regions formed in the substrate of the biochemical analysis unit has a size of less than 0.01 $mm^2$.

In the present invention, the density of the absorptive regions formed in the substrate of the biochemical analysis unit is determined depending upon the material for forming the substrate, the kind of electron beam released from a radioactive substance or the like.

In a preferred aspect of the present invention, the plurality of absorptive regions are formed in the substrate of the biochemical analysis unit at a density of 10 or more per $cm^2$.

In a further preferred aspect of the present invention, the plurality of absorptive regions are formed in the substrate of the biochemical analysis unit at a density of 50 or more per $cm^2$.

In a further preferred aspect of the present invention, the plurality of absorptive regions are formed in the substrate of the biochemical analysis unit at a density of 100 or more per $cm^2$.

In a further preferred aspect of the present invention, the plurality of absorptive regions are formed in the substrate of the biochemical analysis unit at a density of 500 or more per $cm^2$.

In a further preferred aspect of the present invention, the plurality of absorptive regions are formed in the substrate of the biochemical analysis unit at a density of 1,000 or more per $cm^2$.

In a further preferred aspect of the present invention, the plurality of absorptive regions are formed in the substrate of the biochemical analysis unit at a density of 5,000 or more per $cm^2$.

In a further preferred aspect of the present invention, the plurality of absorptive regions are formed in the substrate of the biochemical analysis unit at a density of 10,000 or more per $cm^2$.

In a further preferred aspect of the present invention, the plurality of absorptive regions are formed in the substrate of the biochemical analysis unit at a density of 50,000 or more per $cm^2$.

In a further preferred aspect of the present invention, the plurality of absorptive regions are formed in the substrate of the biochemical analysis unit at a density of 100,000 or more per $cm^2$.

In a preferred aspect of the present invention, the plurality of absorptive regions are formed in the substrate of the biochemical analysis unit in a regular pattern.

In a preferred aspect of the present invention, the plurality of absorptive regions are formed by charging an absorptive material in a plurality of holes formed in the substrate of the biochemical analysis unit.

In a further preferred aspect of the present invention, the plurality of absorptive regions are formed by charging an absorptive material in a plurality of through-holes formed in the substrate of the biochemical analysis unit.

In a further preferred aspect of the present invention, the plurality of absorptive regions are formed by embedding an absorptive material in a plurality of through-holes formed in the substrate of the biochemical analysis unit.

In a further preferred aspect of the present invention, the plurality of absorptive regions are formed by pressing an absorptive membrane containing an absorptive material into a plurality of through-holes formed in the substrate of the biochemical analysis unit.

According to this preferred aspect of the present invention, since the plurality of absorptive regions can be formed only by pressing an absorptive membrane containing an absorptive material into a plurality of through-holes formed in the substrate of the biochemical analysis unit, it is possible to extremely easily produce a biochemical analysis unit formed with a plurality of absorptive regions spaced apart from each other.

In another preferred aspect of the present invention, the plurality of absorptive regions are formed by charging an absorptive material in a plurality of recesses formed in the substrate of the biochemical analysis unit.

In a further preferred aspect of the present invention, the plurality of absorptive regions are formed by embedding an absorptive material in a plurality of recesses formed in the substrate of the biochemical analysis unit.

In a preferred aspect of the present invention, the substrate of the biochemical analysis unit has a property of reducing the energy of radiation to $1/5$ or less when the radiation travels in the substrate by a distance equal to that between neighboring absorptive layers.

In a further preferred aspect of the present invention, the substrate of the biochemical analysis unit has a property of reducing the energy of radiation to $1/10$ or less when the radiation travels in the substrate by a distance equal to that between neighboring absorptive layers.

In a further preferred aspect of the present invention, the substrate of the biochemical analysis unit has a property of reducing the energy of radiation to $1/50$ or less when the radiation travels in the substrate by a distance equal to that between neighboring absorptive layers.

In a further preferred aspect of the present invention, the substrate of the biochemical analysis unit has a property of reducing the energy of radiation to $1/100$ or less when the radiation travels in the substrate by a distance equal to that between neighboring absorptive layers.

In a further preferred aspect of the present invention, the substrate of the biochemical analysis unit has a property of reducing the energy of radiation to $1/500$ or less when the radiation travels in the substrate by a distance equal to that between neighboring absorptive layers.

In a further preferred aspect of the present invention, the substrate of the biochemical analysis unit has a property of reducing the energy of radiation to $1/1,000$ or less when the radiation travels in the substrate by a distance equal to that between neighboring absorptive layers.

In a preferred aspect of the present invention, the substrate of the biochemical analysis unit has a property of reducing the energy of light to $1/5$ or less when the light travels in the substrate by a distance equal to that between neighboring absorptive layers.

In a further preferred aspect of the present invention, the substrate of the biochemical analysis unit has a property of reducing the energy of light to $1/10$ or less when the light travels in the substrate by a distance equal to that between neighboring absorptive layers.

In a further preferred aspect of the present invention, the substrate of the biochemical analysis unit has a property of reducing the energy of light to $1/50$ or less when the light travels in the substrate by a distance equal to that between neighboring absorptive layers.

In a further preferred aspect of the present invention, the substrate of the biochemical analysis unit has a property of reducing the energy of light to $1/100$ or less when the light travels in the substrate by a distance equal to that between neighboring absorptive layers.

In a further preferred aspect of the present invention, the substrate of the biochemical analysis unit has a property of reducing the energy of light to $1/500$ or less when the light travels in the substrate by a distance equal to that between neighboring absorptive layers.

In a further preferred aspect of the present invention, the substrate of the biochemical analysis unit has a property of reducing the energy of light to $1/1,000$ or less when the light travels in the substrate by a distance equal to that between neighboring absorptive layers.

In the present invention, a material for forming the substrate of the biochemical analysis unit is not particularly limited but may be any type of inorganic compound material or organic compound material insofar as it can attenuate radiation energy and/or light energy. The substrate of the biochemical analysis unit can preferably be formed of metal material, ceramic material or plastic material.

Illustrative examples of inorganic compound materials preferably usable for forming the substrate of the biochemical analysis unit and capable of attenuating radiation energy and/or light energy in the present invention include metals such as gold, silver, copper, zinc, aluminum, titanium, tantalum, chromium, iron, nickel, cobalt, lead, tin, selenium and the like; alloys such as brass, stainless steel, bronze and the like; silicon materials such as silicon, amorphous silicon, glass, quartz, silicon carbide, silicon nitride and the like; metal oxides such as aluminum oxide, magnesium oxide, zirconium oxide and the like; and inorganic salts such as tungsten carbide, calcium carbide, calcium sulfate, hydroxy apatite, gallium arsenide and the like. These may have either a monocrystal structure or a polycrystal sintered structure such as amorphous, ceramic or the like.

In the present invention, a high molecular compound is preferably used as an organic compound material preferably usable for forming the substrate of the biochemical analysis unit and capable of attenuating radiation energy and/or light energy. Illustrative examples of high molecular compounds preferably usable for forming the substrate of the biochemical analysis unit in the present invention include polyolefins such as polyethylene, polypropylene and the like; acrylic resins such as polymethyl methacrylate, polybutylacrylate/polymethyl methacrylate copolymer and the like; polyacrylonitrile; polyvinyl chloride; polyvinylidene chloride; polyvinylidene fluoride; polytetrafluoroethylene; polychlorotrifuluoroethylene; polycarbonate; polyesters such as polyethylene naphthalate, polyethylene terephthalate and the like; nylons such as nylon-6, nylon-6,6, nylon-4,10 and the like; polyimide; polysulfone; polyphenylene sulfide; silicon resins such as polydiphenyl siloxane and the like; phenol resins such as novolac and the like; epoxy resin; polyurethane; polystyrene, butadiene-styrene copolymer; polysaccharides such as cellulose, acetyl cellulose, nitrocellulose, starch, calcium alginate, hydroxypropyl methyl cellulose and the like; chitin; chitosan; urushi (Japanese lacquer); polyamides such as gelatin, collagen, keratin and the like; and copolymers of these high molecular materials. These may be a composite compound, and metal oxide particles, glass fiber or the like may be added thereto as occasion demands. Further, an organic compound material may be blended therewith.

Since the capability of attenuating radiation energy generally increases as specific gravity increases, the substrate of the biochemical analysis unit is preferably formed of a compound material or a composite material having specific gravity of 1.0 g/cm$^3$ or more and more preferably formed of a compound material or a composite material having specific gravity of 1.5 g/cm$^3$ to 23 g/cm$^3$.

Since the capability of attenuating light energy generally increases as scattering and/or absorption of light increases, the substrate of the biochemical analysis unit preferably has absorbance of 0.3 per cm (thickness) or more and more preferably has absorbance of 1 per cm (thickness) or more. The absorbance can be determined by placing an integrating sphere immediately behind a plate-like member having a thickness of T cm, measuring an amount A of transmitted light at a wavelength of probe light or emission light used for measurement by a spectrophotometer, and calculating A/T. In the present invention, a light scattering substance or a light absorbing substance may be added to the substrate of the biochemical analysis unit in order to improve the capability of attenuating light energy. Particles of a material different from a material forming the substrate of the biochemical analysis unit may be preferably used as a light scattering substance and a pigment or dye may be preferably used as a light absorbing substance.

In the present invention, a porous material or a fiber material may be preferably used as the absorptive material for forming the absorptive regions of the biochemical analysis unit. The absorptive regions may be formed by combining a porous material and a fiber material.

In the present invention, a porous material for forming the absorptive regions of the biochemical analysis unit may be any type of an organic material or an inorganic material and may be an organic/inorganic composite material.

In the present invention, an organic porous material used for forming the absorptive regions of the biochemical analysis unit is not particularly limited but a carbon porous material such as an activated carbon or a porous material capable of forming a membrane filter is preferably used. Illustrative examples of porous materials capable of forming a membrane filter include nylons such as nylon-6, nylon-6,6, nylon-4,10; cellulose derivatives such as nitrocellulose, acetyl cellulose, butyric-acetyl cellulose; collagen; alginic acids such as alginic acid, calcium alginate, alginic acid/poly-L-lysine polyionic complex; polyolefins such as polyethylene, polypropylene; polyvinyl chloride; polyvinylidene chloride; polyfluoride such as polyvinylidene fluoride, polytetrafluoride; and copolymers or composite materials thereof.

In the present invention, an inorganic porous material used for forming the absorptive regions of the biochemical analysis unit is not particularly limited. Illustrative examples of inorganic porous materials preferably usable in the present invention include metals such as platinum, gold, iron, silver, nickel, aluminum and the like; metal oxides such as alumina, silica, titania, zeolite and the like; metal salts such as hydroxy apatite, calcium sulfate and the like; and composite materials thereof.

In the present invention, a fiber material used for forming the absorptive regions of the biochemical analysis unit is not particularly limited. Illustrative examples of fiber materials preferably usable in the present invention include nylons such as nylon-6, nylon-6,6, nylon-4,10; and cellulose derivatives such as nitrocellulose, acetyl cellulose, butyric-acetyl cellulose.

In a preferred aspect of the present invention, specific binding substances whose sequence, base length, composition and the like are known are absorbed in the plurality of absorptive regions of the biochemical analysis unit.

In a preferred aspect of the present invention, the plurality of stimulable phosphor layer regions of the stimulable phosphor sheet are formed by charging stimulable phosphor in a plurality of holes formed in the support of the stimulable phosphor sheet.

In a further preferred aspect of the present invention, the plurality of stimulable phosphor layer regions of the stimulable phosphor sheet are formed by charging stimulable phosphor in a plurality of through-holes formed in the support of the stimulable phosphor sheet.

In a further preferred aspect of the present invention, the plurality of stimulable phosphor layer regions of the stimulable phosphor sheet are formed by pressing a stimulable phosphor membrane containing stimulable phosphor into a plurality of through-holes formed in the support of the stimulable phosphor sheet.

According to this preferred aspect of the present invention, since the plurality of stimulable phosphor layer regions of the stimulable phosphor sheet can be formed only by pressing a stimulable phosphor membrane containing stimulable phosphor into a plurality of through-holes formed in the support of the stimulable phosphor sheet, it is possible to extremely easily produce a stimulable phosphor sheet formed with a plurality of stimulable phosphor layer regions spaced apart from each other.

In a further preferred aspect of the present invention, the plurality of stimulable phosphor layer regions of the stimulable phosphor sheet are formed by embedding stimulable phosphor in a plurality of through-holes formed in the support of the stimulable phosphor sheet.

In another preferred aspect of the present invention, the plurality of stimulable phosphor layer regions of the stimulable phosphor sheet are formed by charging stimulable phosphor in a plurality of recesses formed in the support of the stimulable phosphor sheet.

In a further preferred aspect of the present invention, the plurality of stimulable phosphor layer regions of the stimulable phosphor sheet are formed by embedding stimulable phosphor in a plurality of recesses formed in the support of the stimulable phosphor sheet.

In a preferred aspect of the present invention, the support of the stimulable phosphor sheet is capable of attenuating radiation energy.

According to this preferred aspect of the present invention, even in the case of forming a plurality of absorptive regions in a biochemical analysis unit at a high density, spotting a solution containing specific binding substances whose sequence, base length, composition and the like are known onto the plurality of absorptive regions of the biochemical analysis unit, thereby absorbing the specific binding substances in the plurality of absorptive regions, specifically binding the specific binding substances absorbed in the plurality of absorptive regions with a substance derived from a living organism and labeled with a radioactive labeling substance by means of hybridization or the like, thereby selective labeling the plurality of absorptive regions of the biochemical analysis unit with the radioactive labeling substance and recording radiation data therein, superposing a stimulable phosphor sheet formed with a plurality of stimulable phosphor layer regions on the thus prepared biochemical analysis unit, exposing the plurality of stimulable phosphor layer regions of the stimulable phosphor sheet to the radioactive labeling substance selectively contained in the plurality of absorptive regions of the biochemical analysis unit, irradiating the plurality of stimulable phosphor layer regions of the stimulable phosphor sheet with a stimulating ray, and photoelectrically detecting stimulated emission released from the plurality of stimulable phosphor layer regions of the stimulable phosphor sheet to produce biochemical analysis data, since the substrate of the biochemical analysis unit and the support of the stimulable phosphor sheet are capable of attenuating radiation energy, electron beams ($\beta$ rays) released from the radioactive labeling substance contained in the individual absorptive regions of the biochemical analysis unit can be effectively prevented from scattering in the substrate of the biochemical analysis unit and can be also effectively prevented from scattering in the support of the stimulable phosphor sheet and, therefore, electron beams ($\beta$ rays) released from the radioactive labeling substance contained in a particular absorptive region of the biochemical analysis unit can be effectively prevented from entering stimulable phosphor layer regions next the corresponding stimulable phosphor layer region. Accordingly, it is possible to produce biochemical analysis data having an excellent quantitative characteristic with high resolution by scanning the plurality of the thus exposed stimulable phosphor layer regions with a stimulating ray and photoelectrically detecting stimulated emission released from the plurality of stimulable phosphor layer regions.

In a preferred aspect of the present invention, the support of the stimulable phosphor sheet has a property of reducing the energy of radiation to $1/5$ or less when the radiation travels in the support by a distance equal to that between neighboring stimulable phosphor layer regions.

In a further preferred aspect of the present invention, the support of the stimulable phosphor sheet has a property of reducing the energy of radiation to $1/10$ or less when the radiation travels in the support by a distance equal to that between neighboring stimulable phosphor layer regions.

In a further preferred aspect of the present invention, the support of the stimulable phosphor sheet has a property of reducing the energy of radiation to $1/50$ or less when the radiation travels in the support by a distance equal to that between neighboring stimulable phosphor layer regions.

In a further preferred aspect of the present invention, the support of the stimulable phosphor sheet has a property of reducing the energy of radiation to $1/100$ or less when the radiation travels in the support by a distance equal to that between neighboring stimulable phosphor layer regions.

In a further preferred aspect of the present invention, the support of the stimulable phosphor sheet has a property of reducing the energy of radiation to $1/500$ or less when the radiation travels in the support by a distance equal to that between neighboring stimulable phosphor layer regions.

In a further preferred aspect of the present invention, the support of the stimulable phosphor sheet has a property of reducing the energy of radiation to $1/1,000$ or less when the radiation travels in the support by a distance equal to that between neighboring stimulable phosphor layer regions.

In a preferred aspect of the present invention, the support of the stimulable phosphor sheet is capable of attenuating light energy.

According to this preferred aspect of the present invention, even in the case of forming a plurality of absorptive regions in a biochemical analysis unit at a high density, spotting a solution containing specific binding substances whose sequence, base length, composition and the like are known onto the plurality of absorptive regions of the biochemical analysis unit, thereby absorbing the specific binding substances in the plurality of absorptive regions, specifically binding, by means of hybridization or the like, the specific binding substances absorbed in the plurality of absorptive regions with a substance derived from a living organism and labeled with a labeling substance which generates chemiluminescence emission when it contacts a chemiluminescent substrate, thereby selective labeling the plurality of absorptive regions of the biochemical analysis unit with the labeling substance which generates chemiluminescence emission when it contacts a chemiluminescent substrate and recording chemiluminescence data therein, bringing the thus prepared biochemical analysis unit into contact with a chemiluminescent substrate, thereby causing the plurality of absorptive regions of the biochemical analysis unit to release chemiluminescence emission, superposing a stimulable phosphor sheet formed with a plurality of stimulable phosphor layer regions on the biochemical analysis unit releasing chemiluminescence emission, exposing the plurality of stimulable phosphor layer regions of the stimulable phosphor sheet to chemiluminescence emission selectively released from the plurality of absorptive regions of the biochemical analysis unit, irradiating the plurality of stimulable phosphor layer regions of the stimulable phosphor sheet with a stimulating ray, and photoelectrically detecting stimulated emission released from the plurality of stimulable phosphor layer regions of the stimulable phosphor sheet to produce biochemical analysis data, since the substrate of the biochemical analysis unit and the support of the stimulable phosphor sheet are capable of attenuating light energy, chemiluminescence emission released from the individual absorptive regions of the biochemical analysis unit can be effectively prevented from scattering in the substrate of the biochemical analysis unit and can be also effectively prevented from scattering in the support of the stimulable phosphor sheet and, therefore, chemiluminescence emission released from a particular absorptive region of the biochemical analysis unit can be effectively prevented from entering stimulable phosphor layer regions next the corresponding stimulable phosphor layer region. Accordingly, it is possible to produce biochemical analysis data having an excellent quantitative characteristic with high resolution by scanning the plurality of the thus exposed stimulable phosphor layer regions with a stimulating ray and photoelectrically detecting stimulated emission released from the plurality of stimulable phosphor layer regions.

In a preferred aspect of the present invention, the support of the stimulable phosphor sheet has a property of reducing the energy of light to ⅕ or less when the light travels in the support by a distance equal to that between neighboring stimulable phosphor layer regions.

In a further preferred aspect of the present invention, the support of the stimulable phosphor sheet has a property of reducing the energy of light to ¹/₁₀ or less when the light travels in the support by a distance equal to that between neighboring stimulable phosphor layer regions.

In a further preferred aspect of the present invention, the support of the stimulable phosphor sheet has a property of reducing the energy of light to ¹/₅₀ or less when the light travels in the support by a distance equal to that between neighboring stimulable phosphor layer regions.

In a further preferred aspect of the present invention, the support of the stimulable phosphor sheet has a property of reducing the energy of light to ¹/₁₀₀ or less when the light travels in the support by a distance equal to that between neighboring stimulable phosphor layer regions.

In a further preferred aspect of the present invention, the support of the stimulable phosphor sheet has a property of reducing the energy of light to ¹/₅₀₀ or less when the light travels in the support by a distance equal to that between neighboring stimulable phosphor layer regions.

In a further preferred aspect of the present invention, the support of the stimulable phosphor sheet has a property of reducing the energy of light to ¹/₁,₀₀₀ or less when the light travels in the support by a distance equal to that between neighboring stimulable phosphor layer regions.

In the present invention, the material for forming the support of the stimulable phosphor sheet is preferably capable of attenuating radiation energy and/or light energy but is not particularly limited. The material for forming the plate-like member of the stimulable phosphor sheet may be any type of inorganic compound material or organic compound material and the plate-like member of the stimulable phosphor sheet can preferably be formed of metal material, ceramic material or plastic material.

Illustrative examples of inorganic compound materials preferably usable for forming the support of the stimulable phosphor sheet in the present invention include metals such as gold, silver, copper, zinc, aluminum, titanium, tantalum, chromium, iron, nickel, cobalt, lead, tin, selenium and the like; alloys such as brass, stainless steel, bronze and the like; silicon materials such as silicon, amorphous silicon, glass, quartz, silicon carbide, silicon nitride and the like; metal oxides such as aluminum oxide, magnesium oxide, zirconium oxide and the like; and inorganic salts such as tungsten carbide, calcium carbide, calcium sulfate, hydroxy apatite, gallium arsenide and the like. These may have either a monocrystal structure or a polycrystal sintered structure such as amorphous, ceramic or the like.

In the present invention, a high molecular compound is preferably used as an organic compound material preferably usable for forming the support of the stimulable phosphor sheet. Illustrative examples of high molecular compounds preferably usable for forming the support of the stimulable phosphor sheet in the present invention include polyolefins such as polyethylene, polypropylene and the like; acrylic resins such as polymethyl methacrylate, polybutylacrylate/polymethyl methacrylate copolymer and the like; polyacrylonitrile; polyvinyl chloride; polyvinylidene chloride; polyvinylidene fluoride; polytetrafluoroethylene; polychlorotrifuluoroethylene; polycarbonate; polyesters such as polyethylene naphthalate, polyethylene terephthalate and the like; nylons such as nylon-6, nylon-6,6, nylon-4,10 and the like; polyimide; polysulfone; polyphenylene sulfide; silicon resins such as polydiphenyl siloxane and the like; phenol resins such as novolac and the like; epoxy resin; polyurethane; polystyrene, butadiene-styrene copolymer; polysaccharides such as cellulose, acetyl cellulose, nitrocellulose, starch, calcium alginate, hydroxypropyl methyl cellulose and the like; chitin; chitosan; urushi (Japanese lacquer); polyamides such as gelatin, collagen, keratin and the like; and copolymers of these high molecular materials. These may be a composite compound, and metal oxide particles, glass fiber or the like may be added thereto as occasion demands. Further, an organic compound material may be blended therewith.

Since the capability of attenuating radiation energy generally increases as specific gravity increases, the support of the stimulable phosphor sheet is preferably formed of a compound material or a composite material having specific gravity of 1.0 g/cm³ or more and more preferably formed of a compound material or a composite material having specific gravity of 1.5 g/cm³ to 23 g/cm³.

Since the capability of attenuating light energy generally increases as scattering and/or absorption of light increases, the support of the stimulable phosphor sheet preferably has absorbance of 0.3 per cm (thickness) or more and more preferably has absorbance of 1 per cm (thickness) or more. The absorbance can be determined by placing an integrating sphere immediately behind a plate-like member having a thickness of T cm, measuring an amount A of transmitted light at a wavelength of probe light or emission light used for measurement by a spectrophotometer, and calculating A/T. In the present invention, a light scattering substance or a light absorbing substance may be added to the support of the stimulable phosphor sheet in order to improve the capability of attenuating light energy. Particles of a material different from a material forming the support of the stimulable phosphor sheet may be preferably used as a light scattering substance and a pigment or dye may be preferably used as a light absorbing substance.

In a preferred aspect of the present invention, the support of the stimulable phosphor is formed with 10 or more stimulable phosphor layer regions.

In a further preferred aspect of the present invention, the support of the stimulable phosphor is formed with 50 or more stimulable phosphor layer regions.

In a further preferred aspect of the present invention, the support of the stimulable phosphor is formed with 100 or more stimulable phosphor layer regions.

In a further preferred aspect of the present invention, the support of the stimulable phosphor is formed with 500 or more stimulable phosphor layer regions.

In a further preferred aspect of the present invention, the support of the stimulable phosphor is formed with 1,000 or more stimulable phosphor layer regions.

In a further preferred aspect of the present invention, the support of the stimulable phosphor is formed with 5,000 or more stimulable phosphor layer regions.

In a further preferred aspect of the present invention, the support of the stimulable phosphor is formed with 10,000 or more stimulable phosphor layer regions.

In a further preferred aspect of the present invention, the support of the stimulable phosphor is formed with 50,000 or more stimulable phosphor layer regions.

In a further preferred aspect of the present invention, the support of the stimulable phosphor is formed with 100,000 or more stimulable phosphor layer regions.

In the present invention, the density of the stimulable phosphor layer regions formed in the stimulable phosphor sheet can be determined based upon the material of the support, the kind of electron beam released from the radioactive labeling substance and the like.

In a preferred aspect of the present invention, the plurality of stimulable phosphor layer regions are formed in the support of the stimulable phosphor sheet at a density of 10 or more per $cm^2$.

In a further preferred aspect of the present invention, the plurality of stimulable phosphor layer regions are formed in the support of the stimulable phosphor sheet at a density of 50 or more per $cm^2$.

In a further preferred aspect of the present invention, the plurality of stimulable phosphor layer regions are formed in the support of the stimulable phosphor sheet at a density of 100 or more per $cm^2$.

In a further preferred aspect of the present invention, the plurality of stimulable phosphor layer regions are formed in the support of the stimulable phosphor sheet at a density of 500 or more per $cm^2$.

In a further preferred aspect of the present invention, the plurality of stimulable phosphor layer regions are formed in the support of the stimulable phosphor sheet at a density of 1,000 or more per $cm^2$.

In a further preferred aspect of the present invention, the plurality of stimulable phosphor layer regions are formed in the support of the stimulable phosphor sheet at a density of 5,000 or more per $cm^2$.

In a further preferred aspect of the present invention, the plurality of stimulable phosphor layer regions are formed in the support of the stimulable phosphor sheet at a density of 10,000 or more per $cm^2$.

In a further preferred aspect of the present invention, the plurality of stimulable phosphor layer regions are formed in the support of the stimulable phosphor sheet at a density of 50,000 or more per $cm^2$.

In a further preferred aspect of the present invention, the plurality of stimulable phosphor layer regions are formed in the support of the stimulable phosphor sheet at a density of 100,000 or more per $cm^2$.

In a preferred aspect of the present invention, the plurality of stimulable phosphor layer regions are formed in the support of the stimulable phosphor sheet in a regular pattern.

In the present invention, the stimulable phosphor usable for storing radiation energy may be of any type insofar as it can store radiation energy or electron beam energy and can be stimulated by an electromagnetic wave to release the radiation energy or the electron beam energy stored therein in the form of light. More specifically, preferably employed stimulable phosphors include alkaline earth metal fluorohalide phosphors $(Ba_{1-x}, M^{2+}_x)FX:yA$ (where $M^{2+}$ is at least one alkaline earth metal selected from the group consisting of Mg, Ca, Sr, Zn and Cd; X is at least one element selected from the group consisting of Cl, Br and I, A is at least one element selected from the group consisting of Eu, Tb, Ce, Tm, Dy, Pr, Ho, Nd, Yb and Er; x is equal to or greater than 0 and equal to or less than 0.6 and y is equal to or greater than 0 and equal to or less than 0.2) disclosed in U.S. Pat. No. 4,239,968, alkaline earth metal fluorohalide phosphors SrFX:Z (where X is at least one halogen selected from the group consisting of Cl, Br and I; Z is at least one of Eu and Ce) disclosed in Japanese Patent Application Laid Open No. 2-276997, europium activated complex halide phosphors $BaFX_xNaX':aEu^{2+}$ (where each of X or X' is at least one halogen selected from the group consisting of Cl, Br and I; x is greater than 0 and equal to or less than 2; and y is greater than 0 and equal to or less than 0.2) disclosed in Japanese Patent Application Laid Open No. 59-56479, cerium activated trivalent metal oxyhalide phosphors MOX:xCe (where M is at least one trivalent metal selected from the group consisting of Pr, Nd, Pm, Sm, Eu, Tb, Dy, Ho, Er, Tm, Yb and Bi; X is at least one halogen selected from the group consisting of Br and I; and x is greater than 0 and less than 0.1) disclosed in Japanese Patent Application laid Open No. 58-69281, cerium activated rare earth oxyhalide phosphors LnOX:xCe (where Ln is at least one rare earth element selected from the group consisting of Y, La, Gd and Lu; X is at least one halogen selected from the group consisting of Cl, Br and I; and x is greater than 0 and equal to or less than 0.1) disclosed in U.S. Pat. No. 4,539,137, and europium activated complex halide phosphors $M^{II}FXaM^IX'bM^{II}X''_2cM^{III}X'''_3xA:yEu^{2+}$ (where $M^{II}$ is at least one alkaline earth metal selected from the group consisting of Ba, Sr and Ca; $M^I$ is at least one alkaline metal selected from the group consisting of Li, Na, K, Rb and Cs; $M^{II}$ is at least one divalent metal selected from the group consisting of Be and Mg; $M^{III}$ is at least one trivalent metal selected from the group consisting of Al, Ga, In and Ti; A is at least one metal oxide; X is at least one halogen selected from the group consisting of Cl, Br and I; each of X', X'' and X''' is at least one halogen selected from the group consisting of F, Cl, Br and I; a is equal to or greater than 0 and equal to or less than 2; b is equal to or greater than 0 and equal to or less than $10^{-2}$; c is equal to or greater than 0 and equal to or less than $10^{-2}$; a+b+c is equal to or greater than $10^{-2}$; x is greater than 0 and equal to or less than 0.5; and y is greater than 0 and equal to or less than 0.2) disclosed in U.S. Pat. No. 4,962,047.

In the present invention, the stimulable phosphor usable for storing the energy of chemiluminescence emission may be of any type insofar as it can store the energy of light in the wavelength band of visible light and can be stimulated by an electromagnetic wave to release in the form of light the energy of light in the wavelength band of visible light stored therein. More specifically, preferably employed stimulable phosphors include at least one selected from the group consisting of metal halophosphates, rare-earth-activated sulfide-host phosphors, aluminate-host phosphors, silicate-host phosphors, fluoride-host phosphors and mixtures of two, three or more of these phosphors. Among them, rare-earth-activated sulfide-host phosphors are more preferable and, particularly, rare-earth-activated alkaline earth metal sulfide-host phosphors disclosed in U.S. Pat. Nos. 5,029,253 and 4,983,834, zinc germanate such as $Zn_2GeO_4$: Mn, V; $Zn_2GeO_4$:Mn disclosed in Japanese Patent Application Laid Open No. 2001-131545, alkaline-earth aluminate such as $Sr_4Al_{14}O_{25}$:Ln (wherein Ln is a rare-earth element) disclosed in Japanese Patent Application Laid Open No. 2001-123162, $Y_{0.8}Lu_{1.2}SiO_5$:Ce, Zr; GdOCl:Ce disclosed in Japanese Patent Publication No. 6-31904 and the like are most preferable.

The above and other objects of the present invention can be also accomplished by a method for exposing a stimulable phosphor sheet comprising the steps of superposing a biochemical analysis unit including a substrate capable of attenuating radiation energy and formed with a plurality of absorptive regions spaced apart from each other and selectively containing a radioactive labeling substance and a stimulable phosphor sheet including a support formed with a plurality of stimulable phosphor layer regions to be space apart from each other in substantially the same pattern as that of the plurality of absorptive regions formed in the substrate of the biochemical analysis unit and exposing the plurality of stimulable phosphor layer regions of the stimulable phosphor sheet to a radioactive labeling substance selectively contained in the plurality of absorptive regions of the biochemical analysis unit, the plurality of absorptive regions of the biochemical analysis unit and the plurality of stimulable phosphor layer regions of the stimulable phosphor sheet being formed so that an average area Sm of the plurality of absorptive regions of the biochemical analysis unit and an average area Sp of the plurality of stimulable phosphor layer regions of the stimulable phosphor sheet meet a requirement that Sp is equal to or larger than a quarter of Sm.

According to the present invention, even in the case of forming a plurality of absorptive regions in a biochemical analysis unit at a high density, spotting a solution containing specific binding substances whose sequence, base length, composition and the like are known onto the plurality of absorptive regions of the biochemical analysis unit, thereby absorbing the specific binding substances in the plurality of absorptive regions, specifically binding the specific binding substances absorbed in the plurality of absorptive regions with a substance derived from a living organism and labeled with a radioactive labeling substance by means of hybridization or the like, thereby selective labeling the plurality of absorptive regions of the biochemical analysis unit with the radioactive labeling substance and recording radiation data therein, superposing a stimulable phosphor sheet formed with a plurality of stimulable phosphor layer regions on the thus prepared biochemical analysis unit, exposing the plurality of stimulable phosphor layer regions of the stimulable phosphor sheet to the radioactive labeling substance selectively contained in the plurality of absorptive regions of the biochemical analysis unit, irradiating the plurality of stimulable phosphor layer regions of the stimulable phosphor sheet with a stimulating ray, and photoelectrically detecting stimulated emission released from the plurality of stimulable phosphor layer regions of the stimulable phosphor sheet to produce biochemical analysis data, since the plurality of stimulable phosphor layer regions are formed in the support of the stimulable phosphor sheet in substantially the same pattern as that of the plurality of absorptive regions formed in the substrate of the biochemical analysis unit and the substrate of the biochemical analysis unit substrate of the biochemical analysis unit is capable of attenuating radiation energy, electron beams ($\beta$ rays) released from the radioactive labeling substance contained in the individual absorptive regions of the biochemical analysis unit can be effectively prevented from scattering in the substrate of the biochemical analysis unit and entering stimulable phosphor layer regions other than that to be exposed to electron beams ($\beta$ rays) released from the radioactive labeling substance contained in the absorptive region and, therefore, it is possible to produce biochemical analysis data having an excellent quantitative characteristic with high resolution by scanning the plurality of the thus exposed stimulable phosphor layer regions with a stimulating ray and photoelectrically detecting stimulated emission released from the plurality of stimulable phosphor layer regions.

Further, even in the case where the substrate of the biochemical analysis unit is capable of attenuating radiation energy, when each of the stimulable phosphor layer regions is formed in the surface of the stimulable phosphor sheet so as to have a much smaller area than that of the corresponding absorptive regions formed in the substrate of the biochemical analysis unit, some electron beams ($\beta$ rays) released from the radioactive labeling substance contained in a particular absorptive region of the biochemical analysis unit do not enter the corresponding stimulable phosphor layer region but enter stimulable phosphor layer regions next to the corresponding stimulable phosphor layer region and, therefore, there is some risk of lowering the quantitative characteristic of biochemical analysis data produced by scanning the plurality of the thus exposed stimulable phosphor layer regions with a stimulating ray and photoelectrically detecting stimulated emission released from the plurality of stimulable phosphor layer regions. However, according to the present invention, since the plurality of absorptive regions of the biochemical analysis unit and the plurality of stimulable phosphor layer regions of the stimulable phosphor sheet are formed so that the average area Sm of the plurality of absorptive regions of the biochemical analysis unit and the average area Sp of the plurality of stimulable phosphor layer regions of the stimulable phosphor sheet meet the requirement that Sp is equal to or larger than a quarter of Sm, electron beams ($\beta$ rays) released from the radioactive labeling substance contained in the individual absorptive regions of the biochemical analysis unit can be effectively prevented from entering stimulable phosphor layer regions next to the corresponding stimulable phosphor layer region and, therefore, it is possible to produce biochemical analysis data having an excellent quantitative characteristic with high resolution by scanning the plurality of the thus exposed stimulable phosphor layer regions with a stimulating ray and photoelectrically detecting stimulated emission released from the plurality of stimulable phosphor layer regions.

The above and other objects of the present invention can be also accomplished by a method for exposing a stimulable phosphor sheet comprising the steps of superposing a biochemical analysis unit including a substrate capable of attenuating light energy and formed with a plurality of absorptive regions spaced apart from each other, selectively containing a labeling substance which generates chemiluminescence emission when it contacts a chemiluminescent substrate and selectively releasing chemiluminescence emission as a result of being brought into contact with a chemiluminescent substrate, and a stimulable phosphor sheet including a support formed with a plurality of stimulable phosphor layer regions to be space apart from each other in substantially the same pattern as that of the plurality of absorptive regions formed in the substrate of the biochemical analysis unit and exposing the plurality of stimulable phosphor layer regions of the stimulable phosphor sheet to chemiluminescence emission selectively released from the plurality of absorptive regions of the biochemical analysis unit, the plurality of absorptive regions of the biochemical analysis unit and the plurality of stimulable phosphor layer regions of the stimulable phosphor sheet being formed so that an average area Sm of the plurality of absorptive regions of the biochemical analysis unit and an average area Sp of the plurality of stimulable phosphor layer regions of the stimulable phosphor sheet meet a requirement that Sp is equal to or larger than a quarter of Sm.

According to the present invention, even in the case of forming a plurality of absorptive regions in a biochemical analysis unit at a high density, spotting a solution containing specific binding substances whose sequence, base length, composition and the like are known onto the plurality of absorptive regions of the biochemical analysis unit, thereby absorbing the specific binding substances in the plurality of absorptive regions, specifically binding, by means of hybridization or the like, the specific binding substances absorbed in the plurality of absorptive regions with a substance derived from a living organism and labeled with a labeling substance which generates chemiluminescence emission when it contacts a chemiluminescent substrate, thereby selective labeling the plurality of absorptive regions of the biochemical analysis unit with the labeling substance which generates chemiluminescence emission when it contacts a chemiluminescent substrate and recording chemiluminescence data therein, bringing the thus prepared biochemical analysis unit into contact with a chemiluminescent substrate, thereby causing the plurality of absorptive regions of the biochemical analysis unit to release chemiluminescence emission, superposing a stimulable phosphor sheet formed with a plurality of stimulable phosphor layer regions on the biochemical analysis unit releasing chemiluminescence emission, exposing the plurality of stimulable phosphor layer regions of the stimulable phosphor sheet to chemiluminescence emission selectively released from the plurality of absorptive regions of the biochemical analysis unit, irradiating the plurality of stimulable phosphor layer regions of the stimulable phosphor sheet with a stimulating ray, and photoelectrically detecting stimulated emission released from the plurality of stimulable phosphor layer regions of the stimulable phosphor sheet to produce biochemical analysis data, since the plurality of stimulable phosphor layer regions are formed in the support of the stimulable phosphor sheet in substantially the same pattern as that of the plurality of absorptive regions formed in the substrate of the biochemical analysis unit and the substrate of the biochemical analysis unit substrate of the biochemical analysis unit is capable of attenuating light energy, chemiluminescence emission released from the individual absorptive regions of the biochemical analysis unit can be effectively prevented from scattering in the substrate of the biochemical analysis unit and entering stimulable phosphor layer regions other than that to be exposed to chemiluminescence emission released from the absorptive region and, therefore, it is possible to produce biochemical analysis data having an excellent quantitative characteristic with high resolution by scanning the plurality of the thus exposed stimulable phosphor layer regions with a stimulating ray and photoelectrically detecting stimulated emission released from the plurality of stimulable phosphor layer regions.

Further, even in the case where the substrate of the biochemical analysis unit is capable of attenuating light energy, when each of the stimulable phosphor layer regions is formed in the surface of the stimulable phosphor sheet so as to have a much smaller area than that of the corresponding absorptive regions formed in the substrate of the biochemical analysis unit, some chemiluminescence emission released from a particular absorptive region of the biochemical analysis unit does not enter the corresponding stimulable phosphor layer region but enters stimulable phosphor layer regions next to the corresponding stimulable phosphor layer region and, therefore, there is some risk of lowering the quantitative characteristic of biochemical analysis data produced by scanning the plurality of the thus exposed stimulable phosphor layer regions with a stimulating ray and photoelectrically detecting stimulated emission released from the plurality of stimulable phosphor layer regions. However, according to the present invention, since the plurality of absorptive regions of the biochemical analysis unit and the plurality of stimulable phosphor layer regions of the stimulable phosphor sheet are formed so that the average area Sm of the plurality of absorptive regions of the biochemical analysis unit and the average area Sp of the plurality of stimulable phosphor layer regions of the stimulable phosphor sheet meet the requirement that Sp is equal to or larger than a quarter of Sm, chemiluminescence emission released from the individual absorptive regions of the biochemical analysis unit can be effectively prevented from entering stimulable phosphor layer regions next to the corresponding stimulable phosphor layer region and, therefore, it is possible to produce biochemical analysis data having an excellent quantitative characteristic with high resolution by scanning the plurality of the thus exposed stimulable phosphor layer regions with a stimulating ray and photoelectrically detecting stimulated emission released from the plurality of stimulable phosphor layer regions.

In a preferred aspect of the present invention, specific binding substances whose sequence, base length, composition and the like are known are absorbed in the plurality of absorptive regions of the biochemical analysis unit and the plurality of absorptive regions of the biochemical analysis unit are selectively labeled with a radioactive labeling substance or a labeling substance which generates chemiluminescence emission when it contacts a chemiluminescent substrate by selectively specifically binding a substance derived from a living organism and labeled with the radioactive labeling substance or a substance derived from a living organism and labeled with the labeling substance which generates chemiluminescence emission when it contacts a chemiluminescent substrate with the specific binding substances absorbed in the plurality of absorptive regions of the biochemical analysis unit.

The above and other objects and features of the present invention will become apparent from the following description made with reference to the accompanying drawings.

DESCRIPTION OF THE PREFERRED EMBODIMENTS

Figure 1:
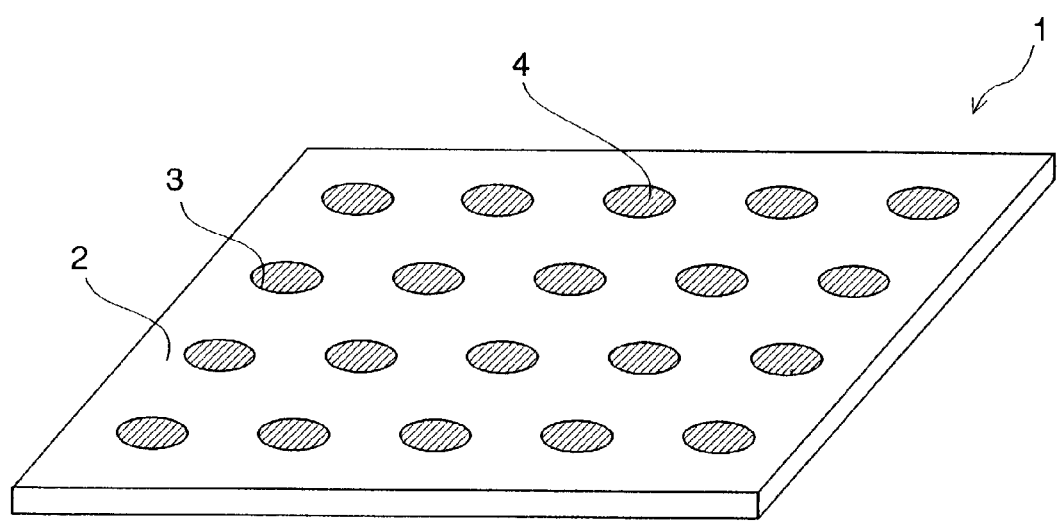
FIG. 1 is a schematic front view showing a biochemical analysis unit which is a preferred embodiment of the present invention.

FIG. 1 is a schematic front view showing a biochemical analysis unit which is a preferred embodiment of the present invention.

As shown in FIG. 1, a biochemical analysis unit 1 according to this embodiment includes a substrate 2 made of stainless steel and formed with a number of substantially circular through-holes 3 at a high density, and a number of absorptive regions 4 are dot-like formed by charging nylon-6 in the through-holes 3.

Although not accurately shown in FIG. 1, in this embodiment, about 10,000 through-holes 3 having an average diameter Dm are regularly formed in the substrate 2 at a density of about 5,000 per $cm^2$.

A number of the absorptive regions 4 are formed by charging nylon-6 in the through-holes 3 formed in the substrate in such a manner that the surfaces of the absorptive regions 4 lie at the same height level as that of the surface of the substrate.

Figure 2:
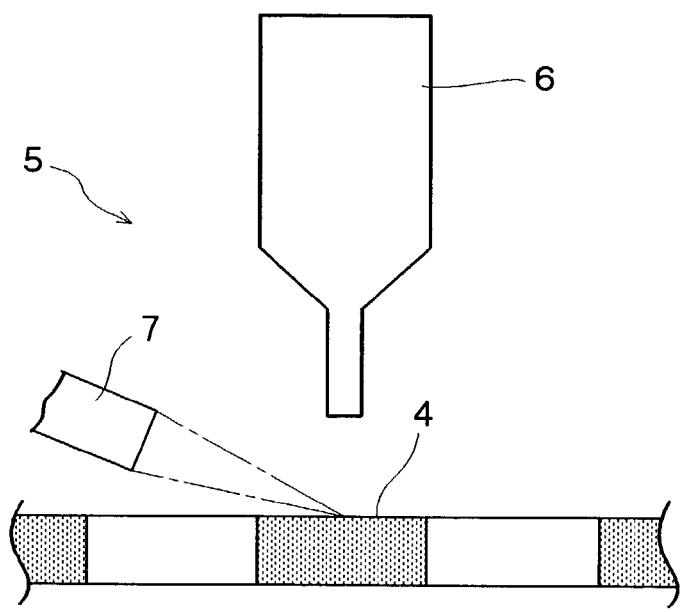
FIG. 2 is a schematic front view showing a spotting device.

FIG. 2 is a schematic front view showing a spotting device.

As shown in FIG. 2, when biochemical analysis is performed, a solution containing specific binding substances such as a plurality of cDNAs whose sequences are known but differ from each other are spotted using a spotting device 5 onto a number of the absorptive regions 4 of the biochemical analysis unit 1 and the specific binding substances are fixed therein.

As shown in FIG. 2, the spotting device 5 includes an injector 6 for ejecting a solution of specific binding substances toward the biochemical analysis unit 1 and a CCD camera 7 and is constituted so that the solution of specific binding substances such as cDNAs are spotted from the injector 6 when the tip end portion of the injector 6 and the center of the absorptive region 4 into which the solution containing specific binding substances is to be spotted are determined to coincide with each other as a result of viewing them using the CCD camera, thereby ensuring that the solution of specific binding substances can be accurately spotted into a number of the absorptive regions 4 of the biochemical analysis unit 1.

Figure 3:
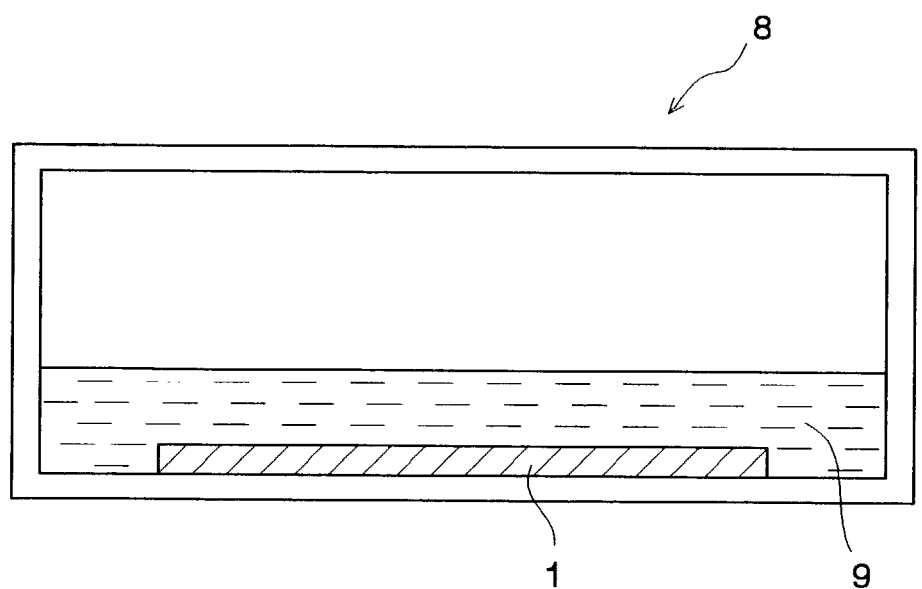
FIG. 3 is a schematic longitudinal cross sectional view showing a hybridization reaction vessel.

FIG. 3 is a schematic longitudinal cross sectional view showing a hybridization reaction vessel.

As shown in FIG. 3, a hybridization reaction vessel 8 is formed to have a substantially rectangular cross section and accommodates a hybridization reaction solution 9 containing as a probe a substance derived from a living organism labeled with a labeling substance therein.

In the case where a specific binding substance such as cDNA is to be labeled with a radioactive labeling substance, a hybridization reaction solution 9 containing a substance derived from a living organism and labeled with a radioactive labeling substance as a probe is prepared and is accommodated in the hybridization reaction vessel 8.

On the other hand, in the case where a specific binding substance such as cDNA is to be labeled with a labeling substance which generates chemiluminescence emission when it contacts a chemiluminescent substrate, a hybridization reaction solution 9 containing a substance derived from a living organism and labeled with a labeling substance which generates chemiluminescence emission when it contacts a chemiluminescent substrate as a probe is prepared and is accommodated in the hybridization reaction vessel 8.

Further, in the case where a specific binding substance such as cDNA is to be labeled with a fluorescent substance such as a fluorescent dye, a hybridization reaction solution 9 containing a substance derived from a living organism and labeled with a fluorescent substance such as a fluorescent dye as a probe is prepared and is accommodated in the hybridization reaction vessel 8.

It is possible to prepare a hybridization reaction solution 9 containing two or more substances derived from a living organism among a substance derived from a living organism and labeled with a radioactive labeling substance, a substance derived from a living organism and labeled with a labeling substance which generates chemiluminescence emission when it contacts a chemiluminescent substrate and a substance derived from a living organism and labeled with a fluorescent substance such as a fluorescent dye and accommodate it in the hybridization vessel 8. In this embodiment, a hybridization reaction solution 9 containing a substance derived from a living organism and labeled with a radioactive labeling substance, a substance derived from a living organism and labeled with a labeling substance which generates chemiluminescence emission when it contacts a chemiluminescent substrate and a substance derived from a living organism and labeled with a fluorescent substance such as a fluorescent dye is prepared and accommodated in the hybridization reaction vessel 8.

When hybridization is to be performed, the biochemical analysis unit 1 containing specific binding substances such as a plurality of cDNAs spotted into a number of absorptive regions 4 is accommodated in the hybridization reaction vessel 8.

As a result, specific binding substances spotted in a number of the absorptive regions 4 of the biochemical analysis unit 1 can be selectively hybridized with a substance derived from a living organism, labeled with a radioactive labeling substance and contained in the hybridization reaction solution 9, a substance derived from a living organism, labeled with a labeling substance which generates chemiluminescence emission when it contacts a chemiluminescent substrate and contained in the hybridization reaction solution 9 and a substance derived from a living organism, labeled with a fluorescent substance such as a fluorescent dye and contained in the hybridization reaction solution 9.

In this manner, radiation data of a radioactive labeling substance, chemiluminescence data of a labeling substance which generates chemiluminescence emission when it contacts a chemiluminescent substrate and fluorescence data of a fluorescent substance such as a fluorescent dye are recorded in a number of absorptive regions 4 formed in the biochemical analysis unit 1.

Fluorescence data recorded in a number of absorptive regions 4 formed in the biochemical analysis unit 1 are read by a scanner described later, thereby producing biochemical analysis data.

On the other hand, radiation data of the radioactive labeling substance recorded in a number of absorptive regions 4 formed in the biochemical analysis unit 1 are transferred onto a stimulable phosphor sheet and read by the scanner described later, thereby producing biochemical analysis data.

Further, chemiluminescence data recorded in a number of absorptive regions 4 formed in the biochemical analysis unit 1 are transferred onto a stimulable phosphor sheet and read by the scanner described later, thereby producing biochemical analysis data.

Figure 4:
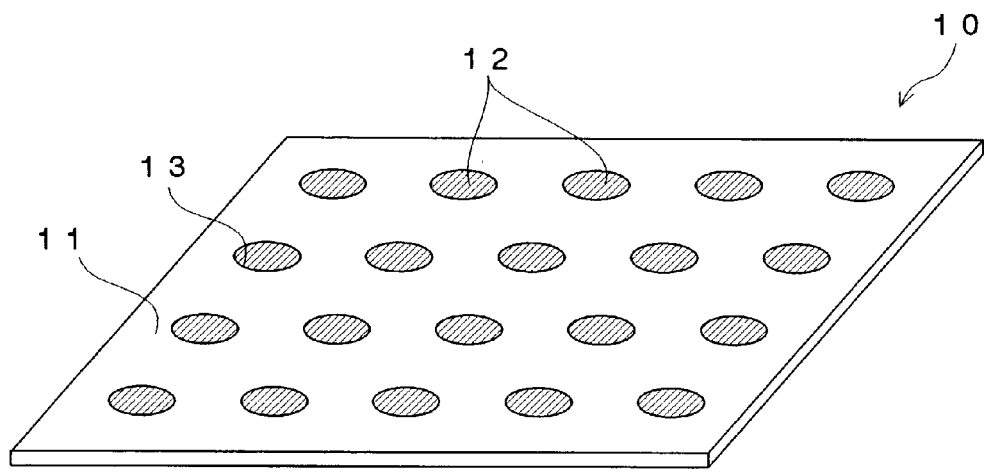
FIG. 4 is a schematic perspective view showing a stimulable phosphor sheet which is a preferred embodiment of the present invention.

FIG. 4 is a schematic perspective view showing a stimulable phosphor sheet which is a preferred embodiment of the present invention.

As shown in FIG. 4, a stimulable phosphor sheet 10 according to this embodiment includes a support 11 made of stainless steel and regularly formed with a number of through-holes 13 and a number of stimulable phosphor layer regions 12 are dot-like formed by charging BaFX system stimulable phosphor (where X is at least one halogen atom selected from the group consisting of Cl, Br and I) capable of absorbing and storing radiation energy and a binder in a number of the through-holes 13 formed in the support 11.

A number of the stimulable phosphor layer regions 12 are formed in the support 11 in the same pattern as that of a number of the absorptive regions 4 formed in the substrate 2 of the biochemical analysis unit 1 and have an average diameter Dp.

In this embodiment, a number of the stimulable phosphor layer regions 12 are formed in the support 11 of the stimulable phosphor sheet 1 so that the average diameter Dp of a number of the stimulable phosphor layer regions 12 is equal to a half of the average diameter Dm of a number of the absorptive regions 4 formed in the substrate 2 of the biochemical analysis unit 1.

Therefore, although not accurately shown in FIG. 4, about 10,000 substantially circular stimulable phosphor layer regions 12 are dot-like formed in the support 11 of the stimulable phosphor sheet 10 at a density of 5,000 per cm$^2$ and in the same regular pattern as that of a number of the absorptive regions 4 formed in the substrate 2 of the biochemical analysis unit 1.

Further, in this embodiment, the stimulable phosphor sheet 10 is formed by charging stimulable phosphor in a number of the through-holes 13 formed in the support 11 so that the surface of the support 11 lies at the same height level as those of a number of the stimulable phosphor layer regions 12.

Figure 5:
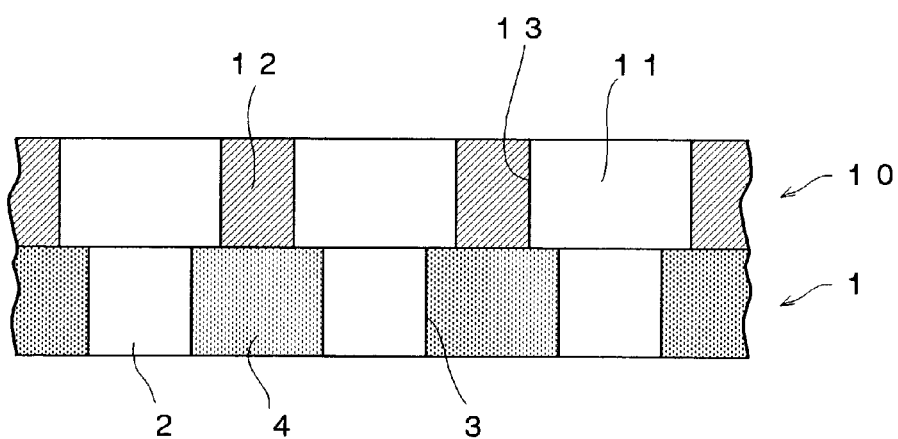
FIG. 5 is a schematic cross-sectional view showing a method for exposing a number of stimulable phosphor layer regions formed in a support of a stimulable phosphor sheet to a radioactive labeling substance contained in a number of absorptive regions formed in a substrate of a biochemical analysis unit.

FIG. 5 is a schematic cross-sectional view showing a method for exposing a number of the stimulable phosphor layer regions 12 formed in the support 11 of the stimulable phosphor sheet 10 to a radioactive labeling substance contained in a number of the absorptive regions 4 formed in the substrate 2 of the biochemical analysis unit 1.

As shown in FIG. 5, when the stimulable phosphor layer regions 12 of a stimulable phosphor sheet 10 are to be exposed, the stimulable phosphor sheet 10 is superposed on the biochemical analysis unit 1 in such a manner that a number of the absorptive regions 4 formed in the biochemical analysis unit 1 face the corresponding stimulable phosphor layer regions 12 formed in the stimulable phosphor sheet 10.

In this embodiment, since the biochemical analysis unit 1 is formed by charging nylon-6 in a number of the through-holes 3 formed in the substrate 2 made of stainless steel, the biochemical analysis unit 1 does not shrink or stretch when it is subjected to liquid processing such as hybridization and, therefore, it is possible to easily and accurately superpose the stimulable phosphor sheet 10 on the biochemical analysis unit 1 so that each of the stimulable phosphor layer regions 12 formed in the stimulable phosphor sheet 10 accurately faces the corresponding absorptive region 4 formed in the substrate 2 of the biochemical analysis unit 1, thereby exposing the stimulable phosphor layer regions 12.

Further, in this embodiment, since a number of the stimulable phosphor layer regions 12 are formed in the support 11 of the stimulable phosphor sheet 10 in the same regular pattern as that of a number of the absorptive regions 4 formed in the substrate 2 of the biochemical analysis unit 1 so that the average diameter Dp thereof is equal to a half of the average diameter Dm of a number of the absorptive regions 4 formed in the substrate 2 of the biochemical analysis unit 1, the stimulable phosphor sheet 10 is typically superposed on the biochemical analysis unit 1 in such a manner that, as shown in FIG. 5, the centers of the absorptive region 4 of the biochemical analysis unit 1 and the stimulable phosphor layer region 12 of the stimulable phosphor sheet 10 facing each other coincide with each other and that a circular region having a quarter area of each of the absorptive regions 4 directly faces the corresponding stimulable phosphor layer region 12.

In this manner, each of the stimulable phosphor layer regions 12 formed in the stimulable phosphor sheet 10 is kept to face the corresponding absorptive region 4 formed in the substrate 2 of the biochemical analysis unit 1 for a predetermined time period, whereby a number of the stimulable phosphor layer regions 12 formed in the stimulable phosphor sheet 10 are exposed to the radioactive labeling substance selectively contained in a number of the absorptive regions 4 formed in the substrate 2 of the biochemical analysis unit 1.

During the exposure operation, electron beams (β rays) are released from the radioactive labeling substance contained in the absorptive regions 4 of the biochemical analysis unit 1. However, since the substrate 2 of the biochemical analysis unit 1 is made of stainless steel and is capable of attenuating radiation energy, electron beams (β rays) released from the radioactive labeling substance contained in a particular absorptive region 4 of the biochemical analysis unit 1 can be efficiently prevented from scattering in the substrate 2 of the biochemical analysis unit 1 and entering stimulable phosphor layer regions 12 next the stimulable phosphor layer region 12 corresponding thereto.

Further, electron beams (β rays) released from the radioactive labeling substance contained in the circular region of the absorptive region 4 directly facing the corresponding stimulable phosphor layer region 12 reliably impinge on the corresponding stimulable phosphor layer region 12.

On the other hand, electron beams (β rays) released from the radioactive labeling substance contained in an area of the absorptive region 4 which does not directly face the corresponding stimulable phosphor layer region 12 may impinge onto stimulable phosphor layer regions 12 next to the corresponding stimulable phosphor layer region 12. However, in this embodiment, since a number of the stimulable phosphor layer regions 12 are formed in the support 11 of the stimulable phosphor sheet 10 so that the average diameter Dp thereof is equal to a half of the average diameter Dm of a number of the absorptive regions formed in the substrate 2 of the biochemical analysis unit 1 and the stimulable phosphor sheet 10 is superposed on the biochemical analysis unit 1 so that a circular area of each absorptive region 4 equal to a quarter of its total area directly faces the corresponding stimulable phosphor layer region 12, even if electron beams (β rays) released from the radioactive labeling substance contained in an area of the absorptive region 4 which does not directly face the corresponding stimulable phosphor layer region 12 impinge onto stimulable phosphor layer regions 12 next to the corresponding stimulable phosphor layer region 12, the amount of the electron beams (β rays) is less than a tolerance value and, therefore, it is possible to prevent degradation of the quantitative characteristic of biochemical analysis data produced by irradiating the exposed stimulable phosphor layer regions 12 with a stimulating ray to excite stimulable phosphor contained in the stimulable phosphor layer regions 12 and photoelectrically detecting stimulated emission released from the stimulable phosphor.

To the contrary, it has been ascertained that, in the case where the average diameter Dp of a number of the stimulable phosphor layer regions 12 formed in the support 11 of the stimulable phosphor sheet 10 is smaller than the average diameter Dm of a number of the absorptive regions 4 formed in the substrate 2 of the biochemical analysis unit 1, the degradation of the quantitative characteristic of biochemical analysis data caused by the incidence of electron beams (β rays) released from the radioactive labeling substance contained in an area of the absorptive region 4 which does not directly face the corresponding stimulable phosphor layer region 12 to stimulable phosphor layer regions 12 next to the corresponding stimulable phosphor layer region 12 cannot be ignored.

Furthermore, in this embodiment, since the support 11 of the stimulable phosphor sheet 10 is made of stainless steel and is capable of attenuating radiation energy, electron beams (β rays) released from the radioactive labeling substance contained in an area of the absorptive region 4 which does not directly face the corresponding stimulable phosphor layer region 12 can be prevented from entering stimulable phosphor layer regions 12 next to the corresponding stimulable phosphor layer region 12, and, therefore, it is possible to expose each of the stimulable phosphor layer regions 12 to only electron beams (β rays) released from the radioactive labeling substance contained in the corresponding absorptive region 4 of the biochemical analysis unit 1.

In this manner, radiation data recorded in a number of the absorptive regions 4 of the biochemical analysis unit 1 are transferred onto and recorded in a number of the stimulable phosphor layer regions 12 of the stimulable phosphor sheet 10.

Figure 6:
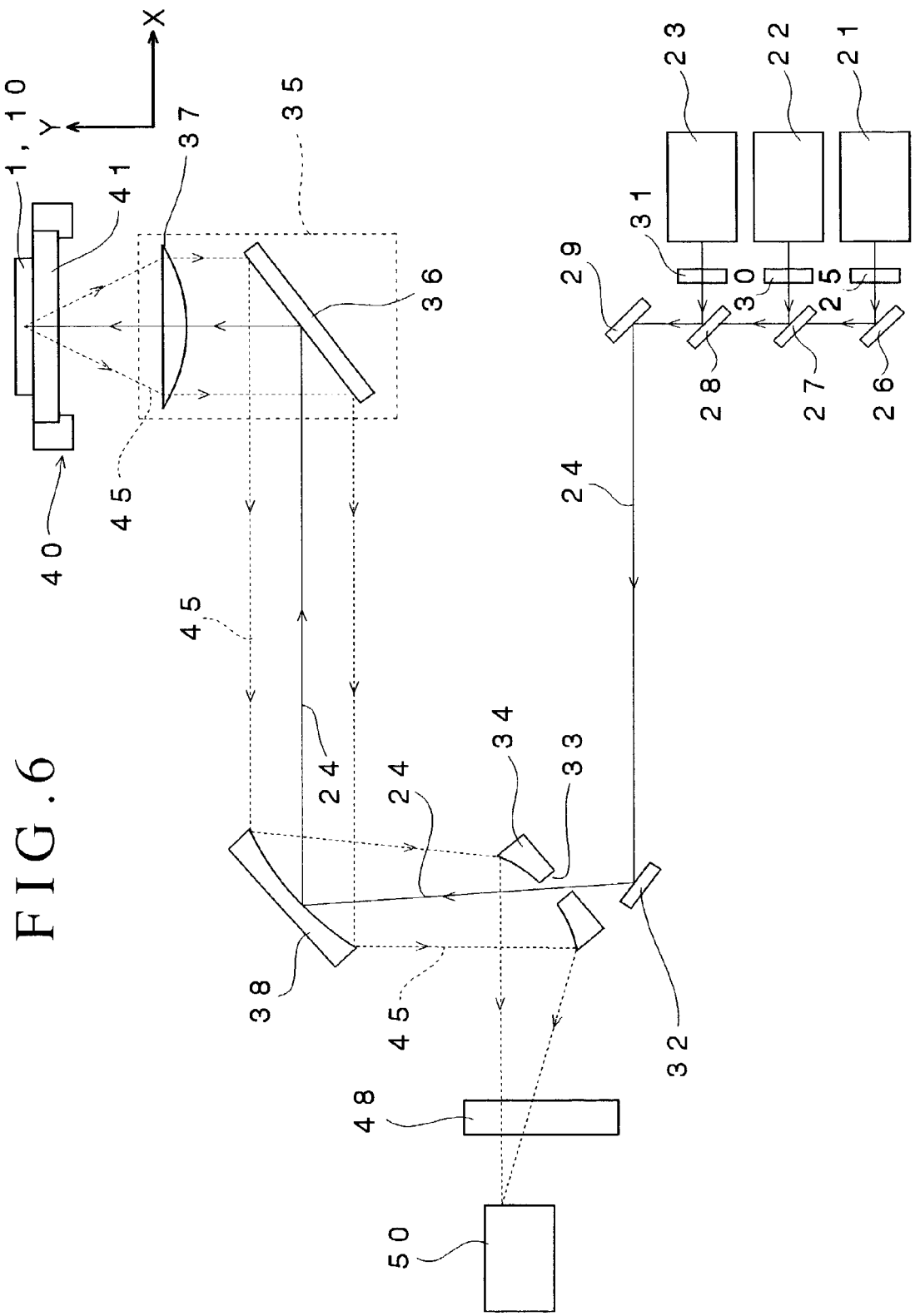
FIG. 6 is a schematic perspective view showing a scanner for reading radiation data recorded in a number of stimulable phosphor layer regions formed in a support of a stimulable phosphor sheet to produce biochemical analysis data.
Figure 7:
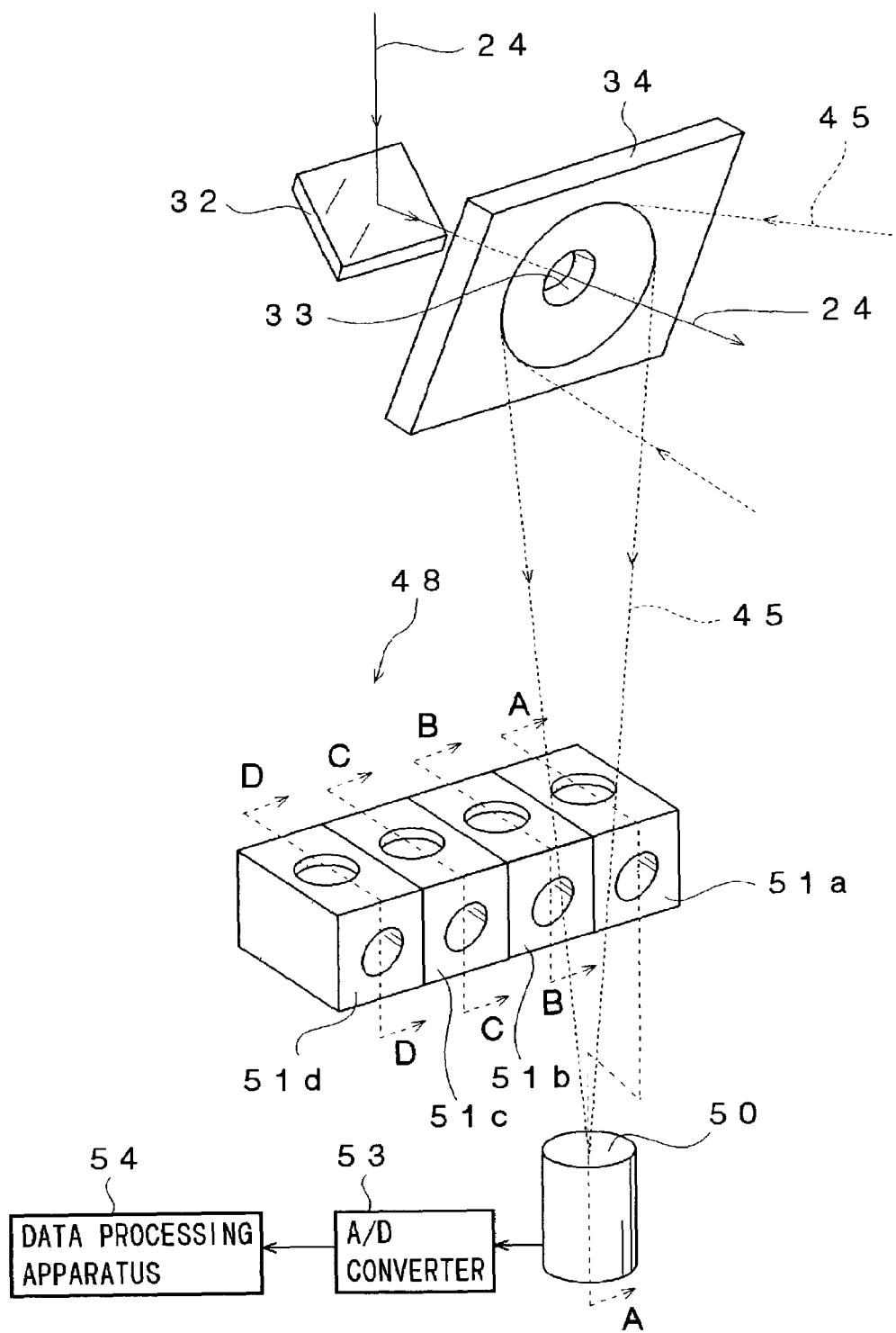
FIG. 7 is a schematic perspective view showing details in the vicinity of a photomultiplier of a scanner shown in FIG. 6.

FIG. 6 is a schematic perspective view showing a scanner for reading radiation data recorded in a number of the stimulable phosphor layer regions 12 formed in the support 11 of the stimulable phosphor sheet 10 to produce biochemical analysis data and FIG. 7 is a schematic perspective view showing details in the vicinity of a photomultiplier of a scanner shown in FIG. 6.

The scanner shown in FIG. 6 is constituted so as to read radiation data recorded in a number of the stimulable phosphor layer regions 12 formed in the support 11 of the stimulable phosphor sheet 10 and fluorescence data of a fluorescent substance such as a fluorescent dye recorded in a number of the absorptive regions 4 formed in the substrate 2 of the biochemical analysis unit 1 to produce biochemical analysis data.

As shown in FIG. 6, the scanner includes a first laser stimulating ray source 21 for emitting a laser beam having a wavelength of 640 nm, a second laser stimulating ray source 22 for emitting a laser beam having a wavelength of 532 nm and a third laser stimulating ray source 23 for emitting a laser beam having a wavelength of 473 nm.

In this embodiment, the first laser stimulating ray source 21 is constituted by a semiconductor laser beam source and the second laser stimulating ray source 22 and the third laser stimulating ray source 23 are constituted by a second harmonic generation element.

A laser beam 24 emitted from the first laser stimulating source 21 passes through a collimator lens 25, thereby being made a parallel beam, and is reflected by a mirror 26. A first dichroic mirror 27 for transmitting light having a wavelength of 640 nm but reflecting light having a wavelength of 532 nm and a second dichroic mirror 28 for transmitting light having a wavelength equal to and longer than 532 nm but reflecting light having a wavelength of 473 nm are provided in the optical path of the laser beam 24 emitted from the first laser stimulating ray source 21. The laser beam 24 emitted from the first laser stimulating ray source 21 and reflected by the mirror 26 passes through the first dichroic mirror 27 and the second dichroic mirror 28 and advances to a mirror 29.

On the other hand, the laser beam 24 emitted from the second laser stimulating ray source 22 passes through a collimator lens 30, thereby being made a parallel beam, and is reflected by the first dichroic mirror 27, thereby changing its direction by 90 degrees. The laser beam 24 then passes through the second dichroic mirror 28 and advances to the mirror 29.

Further, the laser beam 24 emitted from the third laser stimulating ray source 23 passes through a collimator lens 31, thereby being made a parallel beam, and is reflected by the second dichroic mirror 28, thereby changing its direction by 90 degrees. The laser beam 24 then advances to the mirror 29.

The laser beam 24 advancing to the mirror 29 is reflected by the mirror 29 and advances to a mirror 32 to be reflected thereby.

A perforated mirror 34 formed with a hole 33 at the center portion thereof is provided in the optical path of the laser beam 24 reflected by the mirror 32. The laser beam 24 reflected by the mirror 32 passes through the hole 33 of the perforated mirror 34 and advances to a concave mirror 38.

The laser beam 24 advancing to the concave mirror 38 is reflected by the concave mirror 38 and enters an optical head 35.

The optical head 35 includes a mirror 36 and an aspherical lens 37. The laser beam 24 entering the optical head 35 is reflected by the mirror 36 and condensed by the aspherical lens 37 onto the stimulable phosphor sheet 10 or the biochemical analysis unit 1 placed on the glass plate 41 of a stage 40.

When the laser beam 24 impinges on one of the stimulable phosphor layer regions 12 formed in the support 11 of the stimulable phosphor sheet 10, stimulable phosphor contained in the stimulable phosphor layer region 12 is excited, thereby releasing stimulated emission 45. On the other hand, when the laser beam 24 impinges on one of the absorptive regions 4 formed in the substrate 2 of the biochemical analysis unit 1, a fluorescent dye or the like contained in the absorptive region 4 is excited, thereby releasing fluorescence emission 45.

The stimulated emission 45 released from the stimulable phosphor layer region 12 formed in the support 11 of the stimulable phosphor 10 or the fluorescence emission 45 released from the absorptive region 4 formed in the substrate 2 of the biochemical analysis unit 1 is condensed onto the mirror 36 by the aspherical lens 37 provided in the optical head 35 and reflected by the mirror 36 on the side of the optical path of the laser beam 24, thereby being made a parallel beam to advance to the concave mirror 38.

The stimulated emission 45 or the fluorescence emission 45 advancing to the concave mirror 38 is reflected by the concave mirror 38 and advances to the perforated mirror 34.

As shown in FIG. 7, the stimulated emission 45 or the fluorescence emission 45 advancing to the perforated mirror 34 is reflected downward by the perforated mirror 34 formed as a concave mirror and advances to a filter unit 48, whereby light having a predetermined wavelength is cut. The stimulated emission 45 or the fluorescence emission 45 then impinges on a photomultiplier 50, thereby being photoelectrically detected.

As shown in FIG. 7, the filter unit 48 is provided with four filter members 51a, 51b, 51c and 51d and is constituted to be laterally movable in FIG. 7 by a motor (not shown).

Figure 8:
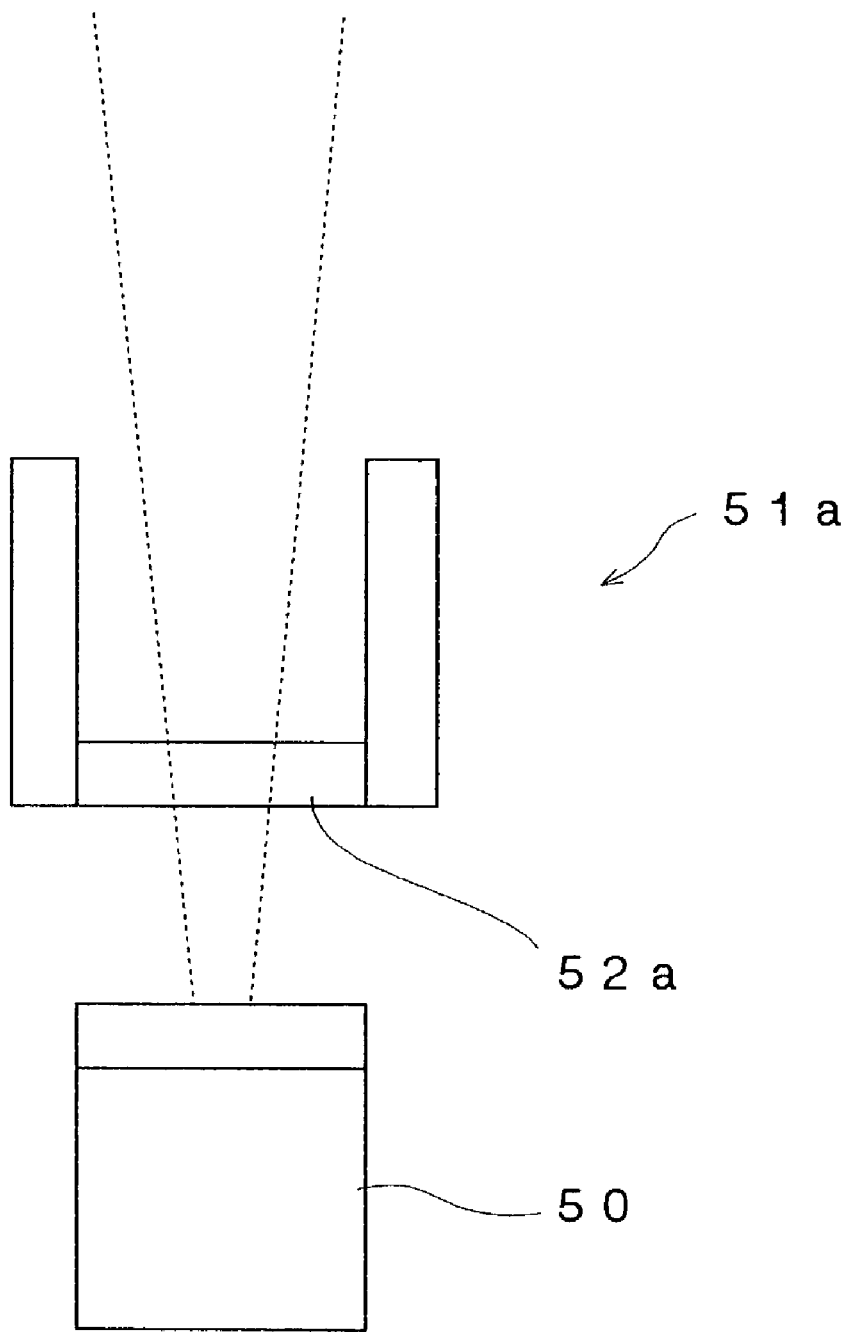
FIG. 8 is a schematic cross-sectional view taken along a line A—A in FIG. 7.

FIG. 8 is a schematic cross-sectional view taken along a line A—A in FIG. 7.

As shown in FIG. 8, the filter member 51a includes a filter 52a and the filter 52a is used for reading fluorescence emission 45 by stimulating a fluorescent substance such as a fluorescent dye contained in a number of the absorptive regions 4 formed in the substrate 2 of the biochemical analysis unit 1 using the first laser stimulating ray source 21 and has a property of cutting off light having a wavelength of 640 nm but transmitting light having a wavelength longer than 640 nm.

Figure 9:
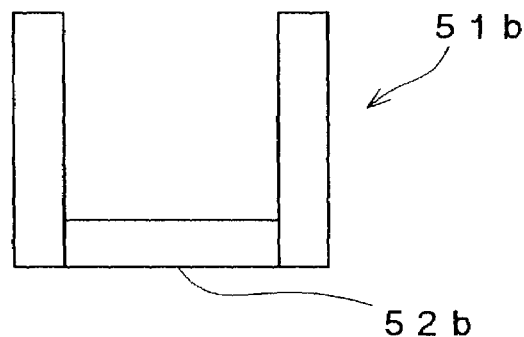
FIG. 9 is a schematic cross-sectional view taken along a line B—B in FIG. 7.

FIG. 9 is a schematic cross-sectional view taken along a line B—B in FIG. 7.

As shown in FIG. 9, the filter member 51b includes a filter 52b and the filter 52b is used for reading fluorescence emission 45 by stimulating a fluorescent substance such as a fluorescent dye contained in a number of the absorptive regions 4 formed in the substrate 2 of the biochemical analysis unit 1 using the second laser stimulating ray source 22 and has a property of cutting off light having a wavelength of 532 nm but transmitting light having a wavelength longer than 532 nm.

Figure 10:
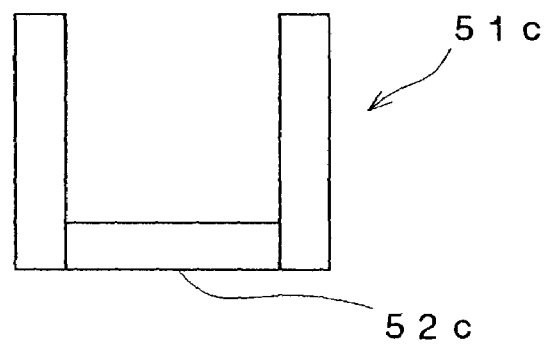
FIG. 10 is a schematic cross-sectional view taken along a line C—C in FIG. 7.

FIG. 10 is a schematic cross-sectional view taken along a line C—C in FIG. 7.

As shown in FIG. 10, the filter member 51c includes a filter 52c and the filter 52c is used for reading fluorescence emission 45 by stimulating a fluorescent substance such as a fluorescent dye contained in in a number of the absorptive regions 4 formed in the substrate 2 of the biochemical analysis unit 1 using the third laser stimulating ray source 23 and has a property of cutting off light having a wavelength of 473 nm but transmitting light having a wavelength longer than 473 nm.

Figure 11:
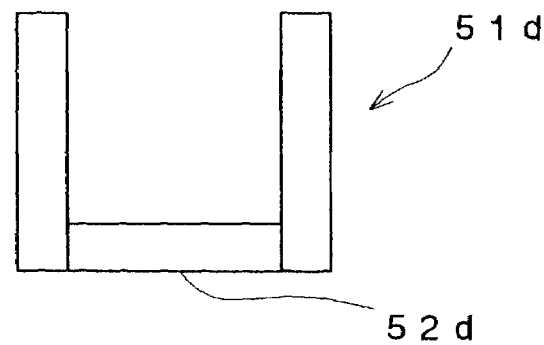
FIG. 11 is a schematic cross-sectional view taken along a line D—D in FIG. 7.

FIG. 11 is a schematic cross-sectional view taken along a line D—D in FIG. 7.

As shown in FIG. 11, the filter member 51d includes a filter 52d and the filter 52d is used for reading stimulated emission 45 released from stimulable phosphor contained in the stimulable phosphor layer 12 formed in the support 11 of the stimulable phosphor sheet 10 upon being stimulated using the first laser stimulating ray source 1 and has a property of transmitting only light having a wavelength corresponding to that of stimulated emission 45 emitted from stimulable phosphor and cutting off light having a wavelength of 640 nm.

Therefore, in accordance with the kind of a stimulating ray source to be used, one of these filter members 51a, 51b, 51c, 51d is selectively positioned in front of the photomultiplier 50, thereby enabling the photomultiplier 50 to photoelectrically detect only light to be detected.

The analog data produced by photoelectrically detecting stimulated emission 45 or fluorescence emission 45 with the photomultiplier 50 are converted by an A/D converter 53 into digital data and the digital data are fed to a data processing apparatus 54.

Although not shown in FIG. 6, the optical head 35 is constituted to be movable by a scanning mechanism in a main scanning direction indicated by an arrow X and a sub-scanning direction indicated by an arrow Y in FIG. 6 so that all of the stimulable phosphor layer regions 12 formed in the support 11 of the stimulable phosphor sheet 10 or all of the absorptive regions 4 formed in the substrate 2 of the biochemical analysis unit 1 can be scanned by the laser beam 24.

Figure 12:
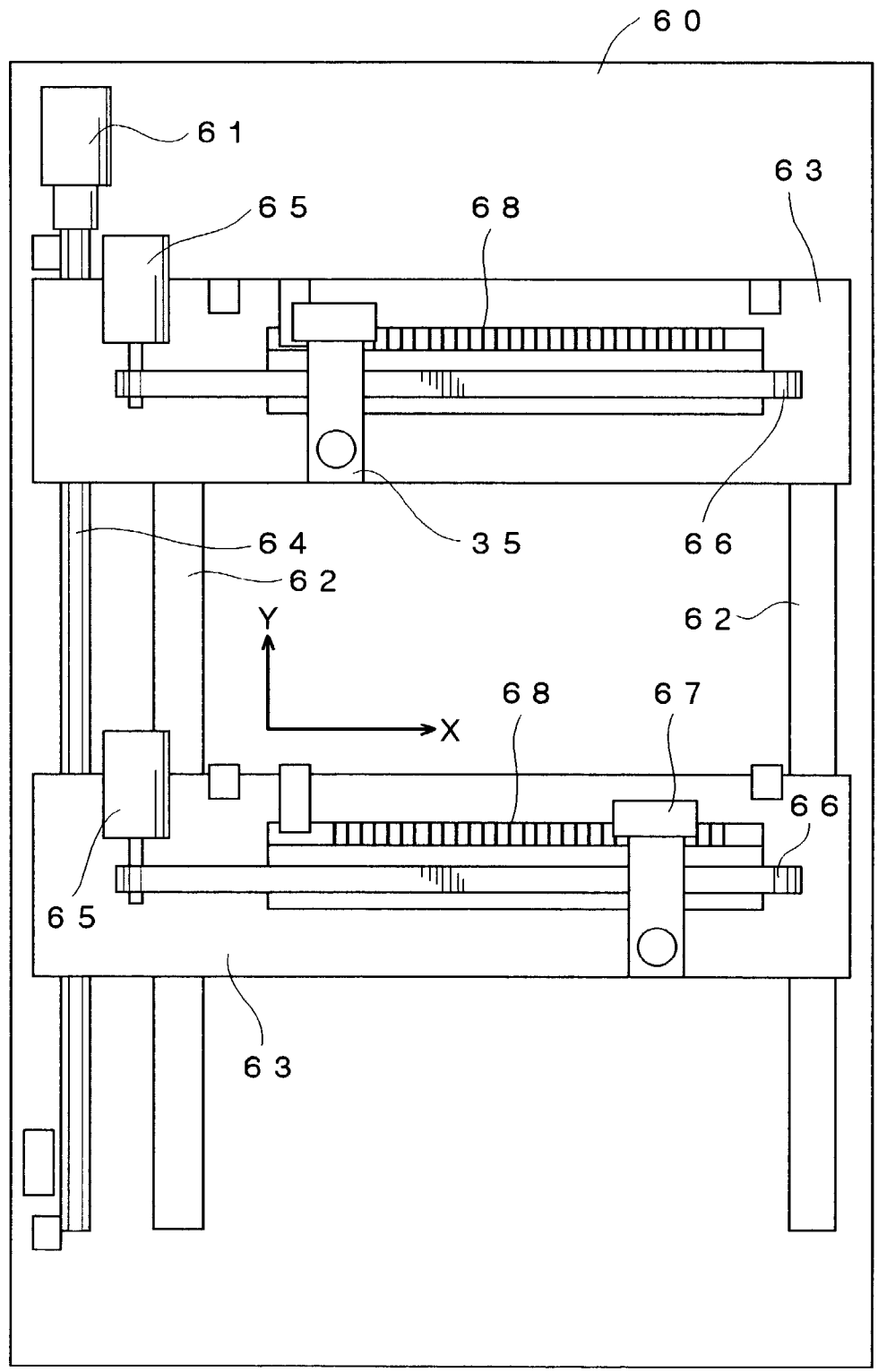
FIG. 12 is a schematic plan view showing a scanning mechanism of an optical head.

FIG. 12 is a schematic plan view showing the scanning mechanism of the optical head 35.

In FIG. 12, optical systems other than the optical head 35 and the paths of the laser beam 24 and stimulated emission 45 or fluorescence emission 45 are omitted for simplification.

As shown in FIG. 12, the scanning mechanism of the optical head 35 includes a base plate 60, and a sub-scanning pulse motor 61 and a pair of rails 62, 62 are fixed on the base plate 60. A movable base plate 63 is further provided so as to be movable in the sub-scanning direction indicated by an arrow Y in FIG. 12.

The movable base plate 63 is formed with a threaded hole (not shown) and a threaded rod 64 rotated by the sub-scanning pulse motor 61 is engaged with the inside of the hole.

A main scanning stepping motor 65 is provided on the movable base plate 63. The main scanning stepping motor 65 is adapted for intermittently driving an endless belt 66 at a pitch equal to the distance between neighboring absorptive regions 4 formed in the biochemical analysis unit 1, namely, the distance between neighboring stimulable phosphor layer regions 12 formed in the stimulable phosphor sheet 10.

The optical head 35 is fixed to the endless belt 66 and when the endless belt 66 is driven by the main scanning stepping motor 65, the optical head 35 is moved in the main scanning direction indicated by an arrow X in FIG. 12.

In FIG. 12, the reference numeral 67 designates a linear encoder for detecting the position of the optical head 35 in the main scanning direction and the reference numeral 68 designates slits of the linear encoder 67.

Therefore, the optical head 35 is moved in the main scanning direction indicated by the arrow X and the sub-scanning direction indicated by the arrow Y in FIG. 12 by driving the endless belt 66 in the main scanning direction by the main scanning stepping motor 65 and intermittently moving the movable base plate 63 in the sub-scanning direction by the sub-scanning pulse motor 61, thereby scanning all of the stimulable phosphor layer regions 12 formed in the support 11 of the stimulable phosphor sheet 10 or all of the absorptive regions 4 formed in the substrate 2 of the biochemical analysis unit 1 with the laser beam 24.

Figure 13:
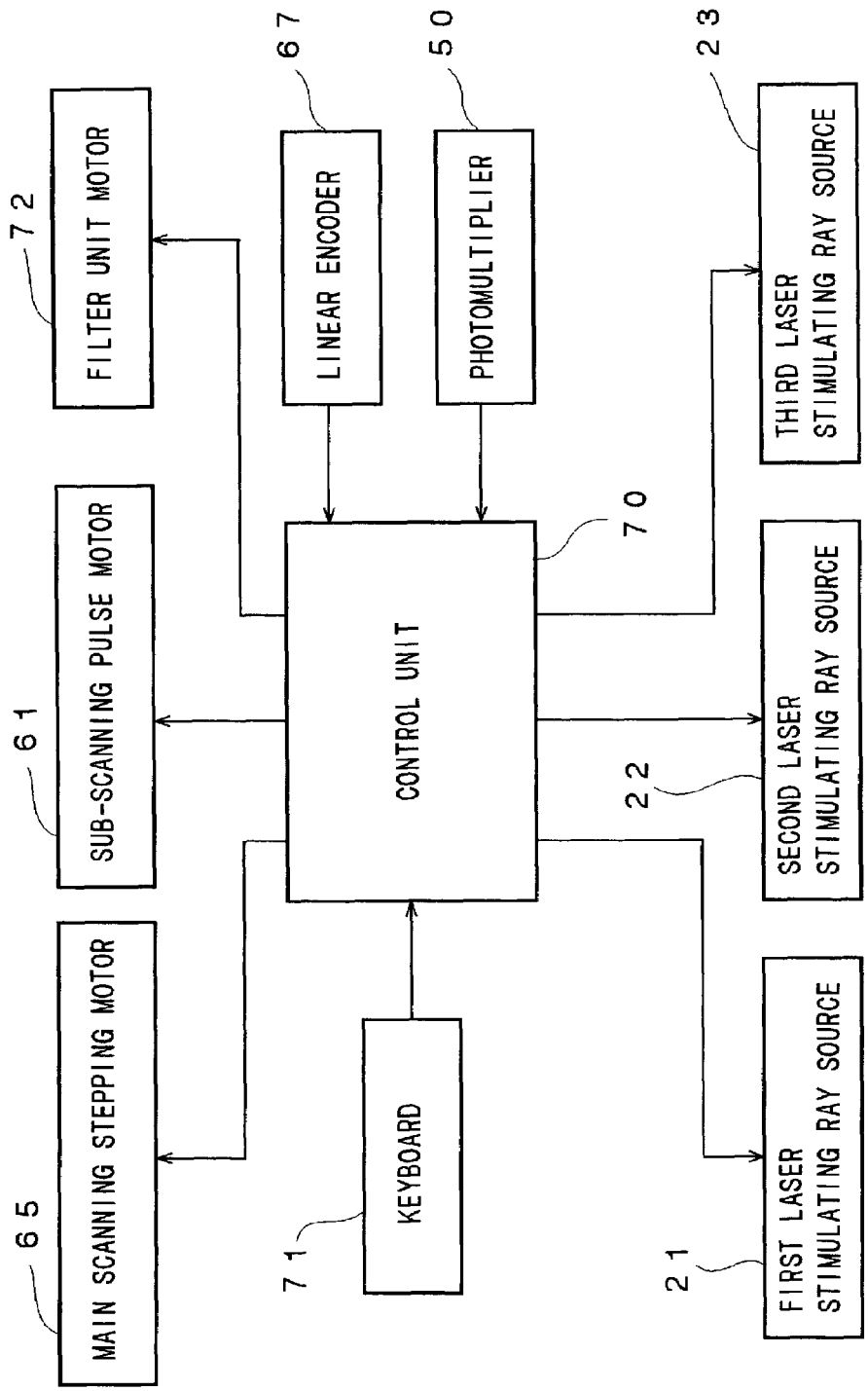
FIG. 13 is a block diagram of a control system, an input system, a drive system and a detection system of the scanner shown in FIG. 6.

FIG. 13 is a block diagram of a control system, an input system, a drive system and a detection system of the scanner shown in FIG. 6.

As shown in FIG. 13, the control system of the scanner includes a control unit 70 for controlling the overall operation of the scanner and the input system of the scanner includes a keyboard 71 which can be operated by a user and through which various instruction signals can be input.

As shown in FIG. 13, the drive system of the scanner includes the main scanning stepping motor 65 for intermittently moving the optical head 35 in the main scanning direction, the sub-scanning pulse motor 61 for moving the optical head 35 in the sub-scanning direction and a filter unit motor 72 for moving the filter unit 48 provided with the four filter members 51a, 51b, 51c and 51d.

The control unit 70 is adapted for selectively outputting a drive signal to the first laser stimulating ray source 21, the second laser stimulating ray source 22 or the third laser stimulating ray source 23 and outputting a drive signal to the filter unit motor 72.

As shown in FIG. 13, the detection system of the scanner includes the photomultiplier 50 and the linear encoder 67 for detecting the position of the optical head 35 in the main scanning direction.

In this embodiment, the control unit 70 is adapted to control the on and off operation of the first laser stimulating ray source 21, the second laser stimulating ray source 22 or the third laser stimulating ray source 23 in accordance with a detection signal indicating the position of the optical head 35 input from the linear encoder 67.

The thus constituted scanner reads radiation data recorded in a number of the stimulable phosphor layer regions 12 formed in the support 11 of the stimulable phosphor sheet 10 and produces biochemical analysis data in the following manner.

A stimulable phosphor sheet 10 is first set on the glass plate 41 of the stage 40 by a user.

An instruction signal indicating that radiation data recorded in the stimulable phosphor layer region 15 formed in the support 11 of the stimulable phosphor sheet 10 are to be read is then input through the keyboard 71.

The instruction signal input through the keyboard 71 is input to the control unit 70 and the control unit 70 outputs a drive signal to the filter unit motor 72 in accordance with the instruction signal, thereby moving the filter unit 48 so as to locate the filter member 51d provided with the filter 52d having a property of transmitting only light having a wavelength corresponding to that of stimulated emission emitted from stimulable phosphor but cutting off light having a wavelength of 640 nm in the optical path of stimulated emission 45.

The control unit 70 further outputs a drive signal to the main scanning stepping motor 65 to move the optical head 35 in the main scanning direction and when it determines based on a detection signal indicating the position of the optical head 35 input from the linear encoder 67 that the optical head 35 has reached a position where a laser beam 24 can be projected onto a first stimulable phosphor layer region 12 among a number of the stimulable phosphor layer regions 12 formed in the support 11 of the stimulable phosphor sheet 10, it outputs a drive stop signal to the main scanning stepping motor 65 and a drive signal to the first stimulating ray source 21, thereby actuating it to emit a laser beam 24 having a wavelength of 640 nm.

A laser beam 24 emitted from the first laser stimulating source 21 passes through the collimator lens 25, thereby being made a parallel beam, and is reflected by the mirror 26.

The laser beam 24 reflected by the mirror 26 passes through the first dichroic mirror 27 and the second dichroic mirror 28 and advances to the mirror 29.

The laser beam 24 advancing to the mirror 29 is reflected by the mirror 29 and advances to the mirror 32 to be reflected thereby.

The laser beam 24 reflected by the mirror 32 passes through the hole 33 of the perforated mirror 34 and advances to the concave mirror 38.

The laser beam 24 advancing to the concave mirror 38 is reflected by the concave mirror 38 and enters the optical head 35.

The laser beam 24 entering the optical head 35 is reflected by the mirror 36 and condensed by the aspherical lens 37 onto the first stimulable phosphor layer region 12 of the stimulable phosphor sheet 10 placed on the glass plate 41 of a stage 40.

In this embodiment, since the stimulable phosphor layer regions 12 are formed by charging stimulable phosphor in a number of the through-holes 13 formed in the support 11 made of stainless steel capable of attenuating light energy, it is possible to effectively prevent the laser beam 24 from scattering in each of the stimulable phosphor layer regions 12 and entering the neighboring stimulable phosphor layer regions 12 to excite stimulable phosphor contained in the neighboring stimulable phosphor layer regions 12.

When the laser beam 24 impinges onto the first stimulable phosphor layer region 12 formed in the support 11 of the stimulable phosphor sheet 10, stimulable phosphor contained in the first stimulable phosphor layer region 12 is excited by the laser beam 24, thereby releasing stimulated emission 45 from the first stimulable phosphor layer region 12.

The stimulated emission 45 released from the first stimulable phosphor layer region 12 is condensed onto the mirror 36 by the aspherical lens 37 provided in the optical head 35 and reflected by the mirror 36 on the side of the optical path of the laser beam 24, thereby being made a parallel beam to advance to the concave mirror 38.

The stimulated emission 45 advancing to the concave mirror 38 is reflected by the concave mirror 38 and advances to the perforated mirror 34.

As shown in FIG. 7, the stimulated emission 45 advancing to the perforated mirror 34 is reflected downward by the perforated mirror 34 formed as a concave mirror and advances to the filter 52d of the filter unit 48.

Since the filter 52d has a property of transmitting only light having a wavelength corresponding to that of stimulated emission emitted from stimulable phosphor and cutting off light having a wavelength of 640 nm, light having a wavelength of 640 nm corresponding to that of the stimulating ray is cut off by the filter 52d and only light having a wavelength corresponding to that of stimulated emission passes through the filter 52d to be photoelectrically detected by the photomultiplier 50.

Analog data produced by photoelectrically detecting stimulated emission 45 with the photomultiplier 50 are converted by an A/D converter 53 into digital data and the digital data are fed to a data processing apparatus 54.

When a predetermined time, for example, several microseconds, has passed after the first stimulating ray source 21 was turned on, the control unit 70 outputs a drive stop signal to the first stimulating ray source 21, thereby turning it off and outputs a drive signal to the main scanning stepping motor 65, thereby moving the optical head 35 by one pitch equal to the distance between neighboring stimulable phosphor layer regions 12 of the stimulable phosphor sheet 10.

When the control unit 70 determines based on a detection signal indicating the position of the optical head 35 input from the linear encoder 67 that the optical head 35 has been moved by one pitch equal to the distance between neighboring stimulable phosphor layer regions 12 and has reached a position where a laser beam 24 can be projected onto a second stimulable phosphor layer region 12 next to the first stimulable phosphor layer region 12 formed in the stimulable phosphor sheet 10, it outputs a drive signal to the first stimulating ray source 21 to turn it on, thereby causing the laser beam 24 to excite stimulable phosphor contained in the second stimulable phosphor layer region 12 formed in the stimulable phosphor sheet 10 next to the first stimulable phosphor layer region 12.

Similarly to the above, the second stimulable phosphor layer region 12 formed in the support 11 of the stimulable phosphor sheet 10 is irradiated with the laser beam 24 emitted from the first laser stimulating ray source 21 for a predetermined time and when biochemical analysis data have been produced from radiation data recorded in the second stimulable phosphor layer region 12 by photoelectrically detecting stimulated emission 45 released from the second stimulable phosphor layer region 12 in response to the excitation of stimulable phosphor with the photomultiplier 50 to produce analog data and digitizing the analog data by the A/D converter 53, the control unit 70 outputs a drive stop signal to the first stimulating ray source 21, thereby turning it off and outputs a drive signal to the main scanning stepping motor 65, thereby moving the optical head 35 by one pitch equal to the distance between neighboring stimulable phosphor layer regions 12.

In this manner, the on and off operation of the first stimulating ray source 21 is repeated in synchronism with the intermittent movement of the optical head 35 and when the control unit 70 determines based on a detection signal indicating the position of the optical head 35 input from the linear encoder 67 that the optical head 35 has been moved by one scanning line in the main scanning direction and that the stimulable phosphor layer regions 12 included in a first line of the stimulable phosphor layer regions 12 formed in the support 11 of the stimulable phosphor sheet 10 have been scanned with the laser beam 24, it outputs a drive signal to the main scanning stepping motor 65, thereby returning the optical head 35 to its original position and outputs a drive signal to the sub-scanning pulse motor 61, thereby causing it to move the movable base plate 63 by one scanning line in the sub-scanning direction.

When the control unit 70 determines based on a detection signal indicating the position of the optical head 35 input from the linear encoder 67 that the optical head 35 has been returned to its original position and determines that the movable base plate 63 has been moved by one scanning line in the sub-scanning direction, similarly to the manner in which the stimulable phosphor layer regions 12 included in the first line of the stimulable phosphor layer regions 12 formed in the support 11 of the stimulable phosphor sheet 10 were sequentially irradiated with the laser beam 24 emitted from the first laser stimulating ray source 21, the stimulable phosphor layer regions 12 included in a second line of the stimulable phosphor layer regions 12 formed in the support 11 of the stimulable phosphor sheet 10 are sequentially irradiated with the laser beam 24 emitted from the first laser stimulating ray source 21, thereby exciting stimulable phosphor contained in the stimulable phosphor layer regions 12 included in the second line and stimulated emission 45 released from the stimulable phosphor layer regions 12 in the second line is sequentially and photoelectrically detected by the photomultiplier 50.

Analog data produced by photoelectrically detecting stimulated emission 45 with the photomultiplier 50 are converted by an A/D converter 53 into digital data, thereby producing biochemical analysis data from radiation data recorded in the stimulable phosphor layer regions 12 formed in the support 11 of the stimulable phosphor sheet 10.

When all of the stimulable phosphor layer regions 12 formed in the support 11 of the stimulable phosphor sheet 10 have been scanned with the laser beam 24 emitted from the first laser stimulating ray source 21 to excite stimulable phosphor contained in the stimulable phosphor layer regions 12 and biochemical analysis data produced from radiation data recorded in the stimulable phosphor layer regions 12 formed in the support 11 of the stimulable phosphor sheet 10 by photoelectrically detecting stimulated emission 45 released from the stimulable phosphor layer regions 12 with the photomultiplier 50 to produce analog data and digitizing the analog data by the A/D converter 53 have been forwarded to the data processing apparatus 54, the control unit 70 outputs a drive stop signal to the first laser stimulating ray source 21, thereby turning it off.

As described above, radiation data of the radioactive labeling substance recorded in a number of the stimulable phosphor layer regions 12 of the stimulable phosphor sheet 10 are read by the scanner of FIG. 6 to produce biochemical analysis data.

On the other hand, when fluorescence data of a fluorescent substance recorded in a number of the absorptive regions 4 formed in the substrate 2 of the biochemical analysis unit 1 are to be read to produce biochemical analysis data, the biochemical analysis unit 1 is first set by the user on the glass plate 41 of the stage 40.

An instruction signal indicating that fluorescence data recorded in a number of the absorptive regions 4 formed in the substrate 2 of the biochemical analysis unit 1 are to be read is then input by the user through the keyboard 71 together with a labeling substance identifying signal for identifying the kind of a fluorescent substance such as a fluorescent dye labeling a substance derived from a living organism.

When the instruction signal and the labeling substance identifying signal are input by the user through the keyboard 71, the control unit 70 selects based on the instruction signal and the labeling substance identifying signal a laser stimulating ray source for emitting a laser beam 24 of a wavelength capable of efficiently stimulating the input fluorescent substance from among the first laser stimulating ray source 21, the second laser stimulating ray source 22 and the third laser stimulating ray source 23 and selects the filter member for cutting light having a wavelength of the laser beam 24 to be used for stimulating the input fluorescent substance and transmitting light having a longer wavelength than that of the laser beam to be used for stimulation from among the three filter members 51a, 51b and 51c.

Similarly to the case where radiation data recorded in a number of the stimulable phosphor layer regions 12 formed in the support 11 of the stimulable phosphor sheet 10 are read, all of the absorptive regions 4 formed in the substrate 2 of the biochemical analysis unit 1 are scanned by the laser beam 24, thereby stimulating a fluorescent substance contained in the absorptive regions 4, fluorescence emission 45 released from the fluorescent substance is photoelectrically detected by the photomultiplier 50 to produce analog data and the analog data are digitized by the A/D converter 53 to be forwarded to the data processing apparatus 54.

In this embodiment, since the absorptive regions 4 of the biochemical analysis unit 1 are formed by charging nylon-6 in the through-holes 3 formed in the substrate 2 made of stainless steel capable of attenuating light energy, it is possible to effectively prevent the laser beam 24 from scattering in each of the absorptive regions 4 and entering the neighboring absorptive regions 4 to excite a fluorescent substance contained in the neighboring absorptive regions 4.

In this manner, fluorescence data of the fluorescent substance are read to produce biochemical analysis data.

Figure 14:
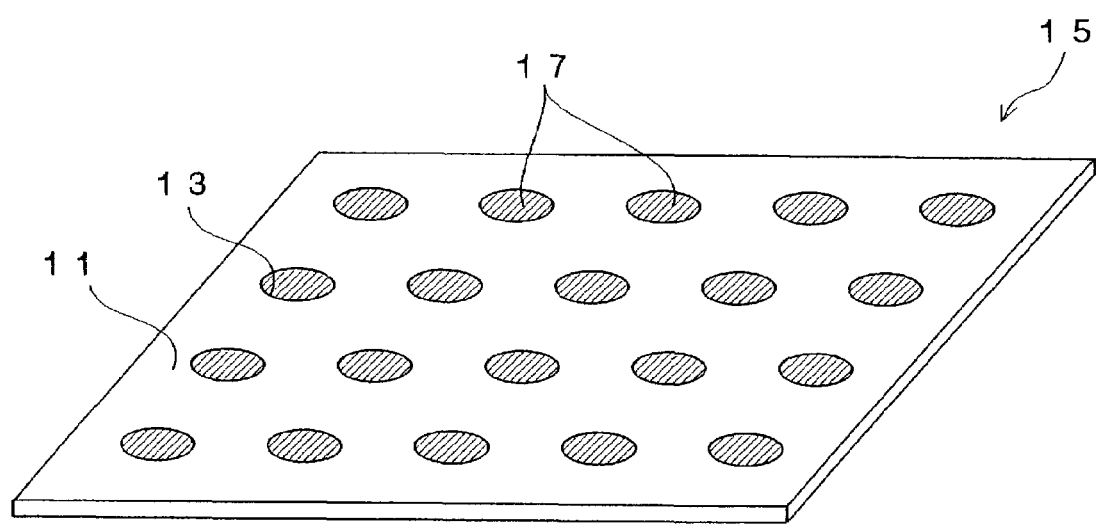
FIG. 14 is a schematic perspective view showing a stimulable phosphor sheet onto which chemiluminescence data recorded in a number of absorptive regions formed in a substrate of a biochemical analysis unit are to be transferred, which is another preferred embodiment of the present invention.

FIG. 14 is a schematic perspective view showing a stimulable phosphor sheet onto which chemiluminescence data recorded in a number of the absorptive regions 4 formed in the substrate 2 of the biochemical analysis unit 1 are to be transferred, which is another preferred embodiment of the present invention.

A stimulable phosphor sheet 15 shown in FIG. 14 has the same configuration as that of the stimulable phosphor sheet 10 shown in FIG. 4 except that a number of stimulable phosphor layer regions 17 are formed by charging SrS system stimulable phosphor capable of absorbing and storing light energy in the through-holes 13 formed in the support 11 made of stainless steel.

Chemiluminescence data recorded in a number of the absorptive regions 4 formed in the substrate 2 of the biochemical analysis unit 1 are transferred onto a number of the stimulable phosphor layer regions 17 of the stimulable phosphor 15 shown in FIG. 14.

When chemiluminescence data recorded in a number of the absorptive regions 4 formed in the substrate 2 of the biochemical analysis unit 1 are to be transferred onto a number of the stimulable phosphor layer regions 17 of the stimulable phosphor 15, a number of the absorptive regions 4 of the biochemical analysis unit 1 are first brought into contact with a chemiluminescent substrate.

As a result, chemiluminescence emission in a wavelength of visible light is selectively released from a number of the absorptive regions 4 of the biochemical analysis unit 1.

Similarly to the manner shown in FIG. 5, the stimulable phosphor sheet 15 is then superposed on the biochemical analysis unit 1 formed of a number of the absorptive regions 4 selectively releasing chemiluminescence emission in such a manner that each of the stimulable phosphor layer regions 17 formed in the support 11 of the stimulable phosphor sheet 15 face the corresponding absorptive region 4 formed in the substrate 2 of the biochemical analysis unit 1.

In this embodiment, since the biochemical analysis unit 1 is formed by charging nylon-6 in a number of the through-holes 3 formed in the substrate 2 made of stainless steel, the biochemical analysis unit 1 does not shrink or stretch when it is subjected to liquid processing such as hybridization and, therefore, it is possible to easily and accurately superpose the stimulable phosphor sheet 15 on the biochemical analysis unit 1 so that each of the stimulable phosphor layer regions 17 formed in the stimulable phosphor sheet 15 accurately faces the corresponding absorptive region 4 formed in the substrate 2 of the biochemical analysis unit 1, thereby exposing the stimulable phosphor layer regions 17 to chemiluminescence emission.

Further, in this embodiment, since a number of the stimulable phosphor layer regions 17 are formed in the support 11 of the stimulable phosphor sheet 15 in the same regular pattern as that of a number of the absorptive regions 4 formed in the substrate 2 of the biochemical analysis unit 1 so that the average diameter Dp thereof is equal to a half of the average diameter Dm of a number of the absorptive regions 4 formed in the substrate 2 of the biochemical analysis unit 1, the stimulable phosphor sheet 15 is typically superposed on the biochemical analysis unit 1 in such a manner that, as shown in FIG. 5, the centers of the absorptive region 4 of the biochemical analysis unit 1 and the stimulable phosphor layer region 17 of the stimulable phosphor sheet 15 facing each other coincide with each other and that a circular area of each absorptive region 4 equal to a quarter of its total area directly faces the corresponding stimulable phosphor layer region 17.

In this manner, each of the stimulable phosphor layer regions 17 formed in the stimulable phosphor sheet 15 is kept to face the corresponding absorptive region 4 formed in the substrate 2 of the biochemical analysis unit 1 for a predetermined time period, whereby a number of the stimulable phosphor layer regions 17 formed in the stimulable phosphor sheet 15 are exposed to chemiluminescence emission released from a number of the absorptive regions 4 formed in the substrate 2 of the biochemical analysis unit 1.

In this embodiment, since the substrate 2 of the biochemical analysis unit 1 is made of stainless steel and is capable of attenuating light energy, chemiluminescence emission released from a particular absorptive region 4 of the biochemical analysis unit 1 can be efficiently prevented from scattering in the substrate 2 of the biochemical analysis unit 1 and entering stimulable phosphor layer regions 17 next the stimulable phosphor layer region 17 corresponding thereto.

Further, chemiluminescence emission released from the circular area of the absorptive region 4 directly facing the corresponding stimulable phosphor layer region 17 reliably impinges on the corresponding stimulable phosphor layer region 17.

On the other hand, chemiluminescence emission released from an area of the absorptive region 4 which does not directly face the corresponding stimulable phosphor layer region 17 may impinge onto stimulable phosphor layer regions 17 next to the corresponding stimulable phosphor layer region 17. However, in this embodiment, since a number of the stimulable phosphor layer regions 17 are formed in the support 11 of the stimulable phosphor sheet 10 so that the average diameter Dp thereof is equal to a half of the average diameter Dm of a number of the absorptive regions formed in the substrate 2 of the biochemical analysis unit 1 and the stimulable phosphor sheet 15 is superposed on the biochemical analysis unit 1 so that a circular area of each absorptive region 4 equal to a quarter of its total area directly faces the corresponding stimulable phosphor layer region 17, even if chemiluminescence emission released from an area of the absorptive region 4 which does not directly face the corresponding stimulable phosphor layer region 17 impinges onto stimulable phosphor layer regions 17 next to the corresponding stimulable phosphor layer region 17, the amount of the chemiluminescence emission is less than a tolerance value and, therefore, it is possible to prevent degradation of the quantitative characteristic of biochemical analysis data produced by irradiating the exposed stimulable phosphor layer regions 17 with a stimulating ray to excite stimulable phosphor contained in the stimulable phosphor layer regions 17 and photoelectrically detecting stimulated emission released from the stimulable phosphor.

To the contrary, in the case where the average diameter Dp of a number of the stimulable phosphor layer regions 17 formed in the support 11 of the stimulable phosphor sheet 15 is smaller than the average diameter Dm of a number of the absorptive regions 4 formed in the substrate 2 of the biochemical analysis unit 1, it has been ascertained that the degradation of the quantitative characteristic of biochemical analysis data caused by the incidence of chemiluminescence emission from an area of the absorptive region 4 which does not directly face the corresponding stimulable phosphor layer region 17 to stimulable phosphor layer regions 17 next to the corresponding stimulable phosphor layer region 17 cannot be ignored.

Furthermore, in this embodiment, since the support 11 of the stimulable phosphor sheet 12 is made of stainless steel and is capable of attenuating radiation energy, chemiluminescence emission released from an area of the absorptive region 4 which does not directly face the corresponding stimulable phosphor layer region 17 can be prevented from entering stimulable phosphor layer regions 12 next to the corresponding stimulable phosphor layer region 17, and, therefore, it is possible to expose each of the stimulable phosphor layer regions 17 to only chemiluminescence emission released from the corresponding absorptive region 4 of the biochemical analysis unit 1.

In this embodiment, since the substrate 2 made of stainless steel capable of attenuating light energy are present around each of the absorptive regions 4 of the biochemical analysis unit 1, chemiluminescence emission released from the absorptive regions 4 of the biochemical analysis unit 1 during the exposure operation can be efficiently prevented from scattering in the biochemical analysis unit 1. Further, since the support 11 of the stimulable phosphor sheet 15 is made of stainless steel capable of attenuating light energy, chemiluminescence emission released from the absorptive regions 4 of the biochemical analysis unit 1 can be efficiently prevented from scattering in the support 11 of the stimulable phosphor sheet 15 and impinging on the stimulable phosphor layer regions 17 neighboring absorptive regions 4 face.

In this manner, chemiluminescence data recorded in a number of the absorptive regions 4 of the biochemical analysis unit 1 are transferred onto and are recorded in a number of the stimulable phosphor layer regions 17 formed in the support 11 of the stimulable phosphor sheet 15.

Figure 15:
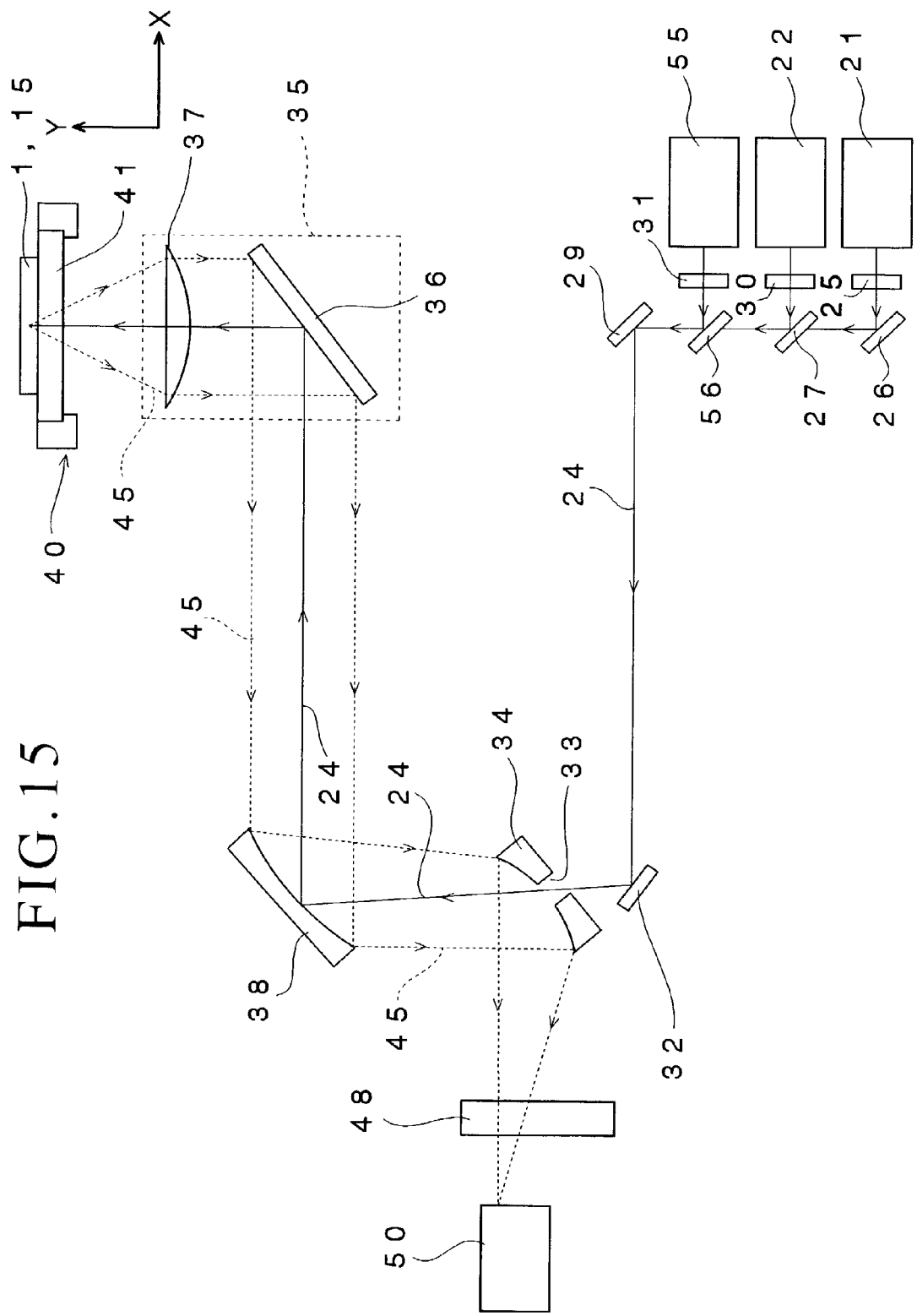
FIG. 15 is a schematic perspective view showing a scanner for reading chemiluminescence data recorded in a number of stimulable phosphor layer regions formed in a support of a stimulable phosphor sheet and producing biochemical analysis data.
Figure 16:
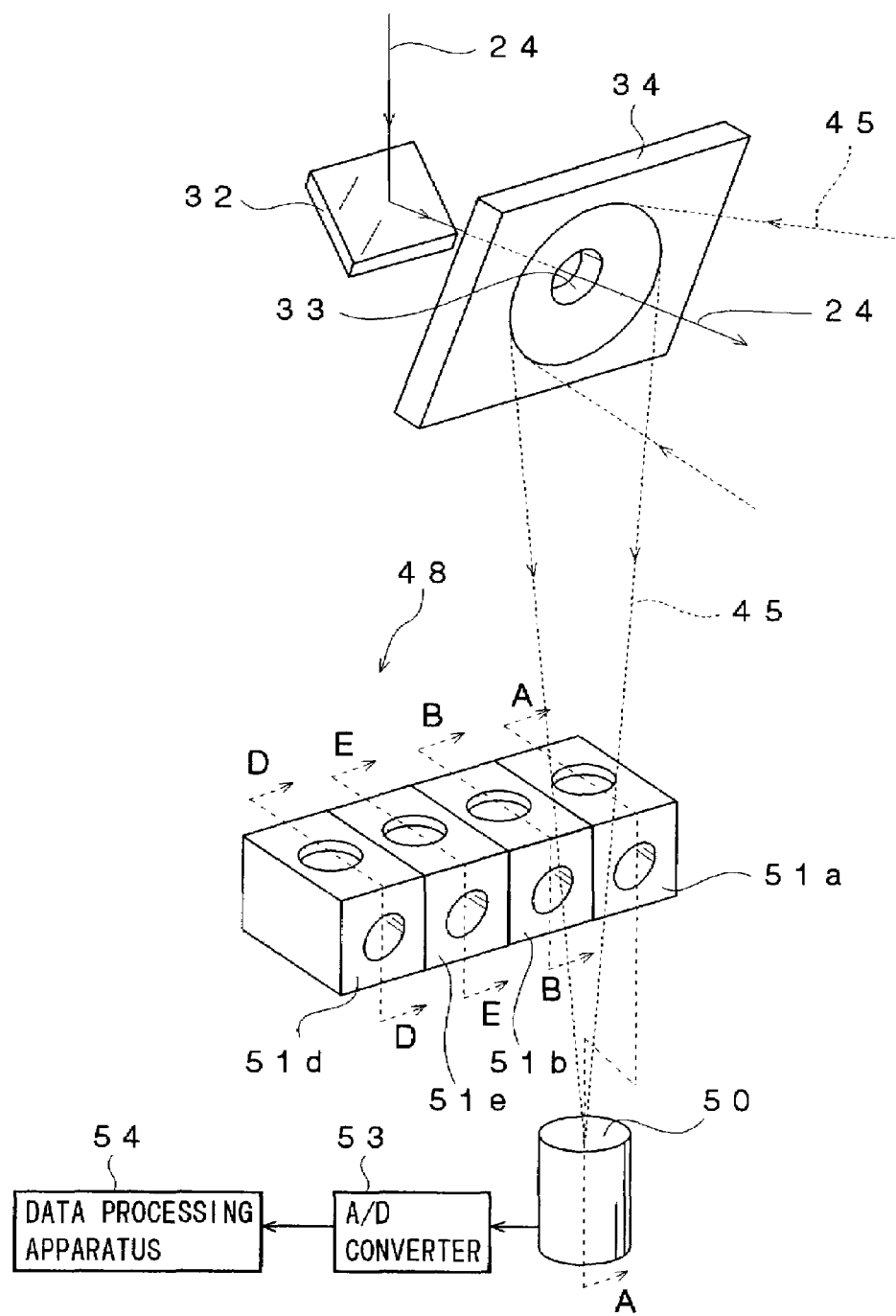
FIG. 16 is a schematic perspective view showing details in the vicinity of a photomultiplier of a scanner shown in FIG. 15.
Figure 17:
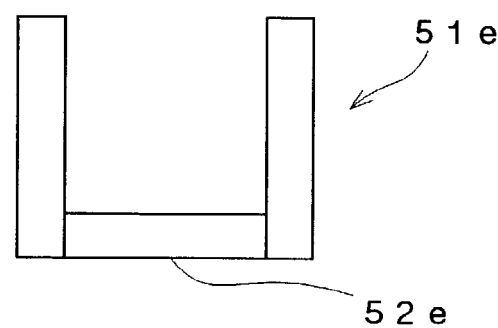
FIG. 17 is a schematic cross-sectional view taken along a line E—E in FIG. 16.

FIG. 15 is a schematic perspective view showing a scanner for reading chemiluminescence data recorded in a number of the stimulable phosphor layer regions 17 formed in the support 11 of the stimulable phosphor sheet 15 and producing biochemical analysis data, FIG. 16 is a schematic perspective view showing details in the vicinity of a photomultiplier of a scanner shown in FIG. 15 and FIG. 17 is a schematic cross-sectional view taken along a line E—E in FIG. 16.

A scanner shown in FIGS. 15 to 17 has the same configuration as that of the scanner shown in FIGS. 6 to 13 except that it includes a fourth laser stimulating ray source 55 for emitting a laser beam 24 having a wavelength of 980 nm which can effectively stimulate SrS system stimulable phosphor instead of the third laser stimulating ray source 23 for emitting a laser beam 24 having a wavelength of 473 nm, includes a filter member 51e provided with a filter having a property of transmitting only light having a wavelength corresponding to that of stimulated emission emitted from stimulable phosphor and cutting off light having a wavelength of 980 nm, and includes a third dichroic mirror 56 for transmitting light having a wavelength equal to and shorter than 640 nm but reflecting light having a wavelength of 980 nm instead of the second dichroic mirror 28 for transmitting light having a wavelength equal to and longer than 532 nm but reflecting light having a wavelength of 473 nm.

The thus constituted scanner reads chemiluminescence data recorded in a number of the stimulable phosphor layer regions 17 of the stimulable phosphor sheet 15 and produces biochemical analysis data in the following manner.

A stimulable phosphor sheet 15 is first set on the glass plate 41 of the stage 40 by a user.

An instruction signal indicating that chemiluminescence data recorded in the stimulable phosphor layer regions 17 formed in the stimulable phosphor sheet 15 are to be read is then input through the keyboard 71.

The instruction signal input through the keyboard 71 is input to the control unit 70 and the control unit 70 outputs a drive signal to the filter unit motor 72 in accordance with the instruction signal, thereby moving the filter unit 48 so as to locate the filter member 51e provided with a filter 52e (FIG. 16) having a property of transmitting only light having a wavelength corresponding to that of stimulated emission emitted from the stimulable phosphor layer regions 17 and cutting off light having a wavelength of 980 nm in the optical path of stimulated emission 45.

The control unit 70 further outputs a drive signal to the main scanning stepping motor 65 to move the optical head 35 in the main scanning direction and when it determines based on a detection signal indicating the position of the optical head 35 input from the linear encoder 67 that the optical head 35 has reached a position where a laser beam 24 can be projected onto a first stimulable phosphor layer region 17 among a number of the stimulable phosphor layer regions 17 formed in the stimulable phosphor sheet 15, it outputs a drive stop signal to the main scanning stepping motor 65 and a drive signal to the fourth stimulating ray source 55, thereby actuating it to emit a laser beam 24 having a wavelength of 980 nm.

A laser beam 24 emitted from the fourth laser stimulating ray source 55 passes through a collimator lens 31, thereby being made a parallel beam, and is reflected by the third dichroic mirror 56, thereby changing its direction by 90 degrees. The laser beam 24 then advances to the mirror 29.

The laser beam 24 advancing to the mirror 29 is reflected by the mirror 29 and advances to the mirror 32 to be reflected thereby.

The laser beam 24 reflected by the mirror 32 passes through the hole 33 of the perforated mirror 34 and advances to the concave mirror 38.

The laser beam 24 advancing to the concave mirror 38 is reflected by the concave mirror 38 and enters the optical head 35.

The laser beam 24 entering the optical head 35 is reflected by the mirror 36 and condensed by the aspherical lens 37 onto the first stimulable phosphor layer region 17 of the stimulable phosphor sheet 15 placed on the glass plate 41 of a stage 40.

In this embodiment, since the stimulable phosphor layer regions 17 are formed by charging stimulable phosphor in a number of the through-holes 13 formed in the support 11 made of stainless steel, it is possible to effectively prevent the laser beam 24 from scattering in each of the stimulable phosphor layer regions 17 and entering the neighboring stimulable phosphor layer regions 17 to excite stimulable phosphor contained in the neighboring stimulable phosphor layer regions 17.

When the laser beam 24 impinges onto the first stimulable phosphor layer region 17 formed in the stimulable phosphor sheet 15, stimulable phosphor contained in the first stimulable phosphor layer region 17 formed in the stimulable phosphor sheet 15 is excited by the laser beam 24, thereby releasing stimulated emission 45 from the first stimulable phosphor layer region 17.

The stimulated emission 45 released from the first stimulable phosphor layer region 17 of the stimulable phosphor sheet 15 is condensed onto the mirror 36 by the aspherical lens 37 provided in the optical head 35 and reflected by the mirror 36 on the side of the optical path of the laser beam 24, thereby being made a parallel beam to advance to the concave mirror 38.

The stimulated emission 45 advancing to the concave mirror 38 is reflected by the concave mirror 38 and advances to the perforated mirror 34.

As shown in FIG. 16, the stimulated emission 45 advancing to the perforated mirror 34 is reflected downward by the perforated mirror 34 formed as a concave mirror and advances to the filter 52e of the filter unit 48.

Since the filter 52e has a property of transmitting only light having a wavelength corresponding to that of stimulated emission emitted from stimulable phosphor and cutting off light having a wavelength of 980 nm, light having a wavelength of 980 nm corresponding to that of the stimulating ray is cut off by the filter 52e and only light having a wavelength corresponding to that of stimulated emission passes through the filter 52e to be photoelectrically detected by the photomultiplier 50.

Analog data produced by photoelectrically detecting stimulated emission 45 with the photomultiplier 50 are converted by an A/D converter 53 into digital data and the digital data are fed to a data processing apparatus 54.

When a predetermined time has passed after the fourth stimulating ray source 55 was turned on, the control unit 70 outputs a drive stop signal to the fourth stimulating ray source 55, thereby turning it off and outputs a drive signal to the main scanning stepping motor 65, thereby moving the optical head 35 by one pitch equal to the distance between neighboring stimulable phosphor layer regions 17 of the stimulable phosphor sheet 15.

When the control unit 70 determines based on a detection signal indicating the position of the optical head 35 input from the linear encoder 67 that the optical head 35 has been moved by one pitch equal to the distance between neighboring stimulable phosphor layer regions 17, it outputs a drive signal to the fourth stimulating ray source 55 to turn it on, thereby causing the laser beam 24 to excite stimulable phosphor contained in a second stimulable phosphor layer region 17 formed in the support 11 of the stimulable phosphor sheet 15 next to the first stimulable phosphor layer region 17.

Similarly to the above, the second stimulable phosphor layer region 17 formed in the stimulable phosphor sheet 15 is irradiated with the laser beam 24 for a predetermined time and when stimulated emission 45 released from the second stimulable phosphor layer region 17 is photoelectrically detected by the photomultiplier 50, the control unit 70 outputs a drive stop signal to the fourth stimulating ray source 55, thereby turning it off and outputs a drive signal to the main scanning stepping motor 65, thereby moving the optical head 35 by one pitch equal to the distance between neighboring stimulable phosphor layer regions 17.

In this manner, the on and off operation of the fourth stimulating ray source 55 is repeated in synchronism with the intermittent movement of the optical head 35 and when the control unit 70 determines based on a detection signal indicating the position of the optical head 35 input from the linear encoder 67 that the optical head 35 has been moved by one scanning line in the main scanning direction and that the stimulable phosphor layer regions 17 included in a first line of the stimulable phosphor layer regions 17 formed in the stimulable phosphor sheet 15 have been scanned with the laser beam 24, it outputs a drive signal to the main scanning stepping motor 65, thereby returning the optical head 35 to its original position and outputs a drive signal to the sub-scanning pulse motor 61, thereby causing it to move the movable base plate 63 by one scanning line in the sub-scanning direction.

When the control unit 70 determines based on a detection signal indicating the position of the optical head 35 input from the linear encoder 67 that the optical head 35 has been returned to its original position and determines that the movable base plate 63 has been moved by one scanning line in the sub-scanning direction, similarly to the manner in which the stimulable phosphor layer regions 17 included in the first line of the stimulable phosphor layer regions 17 formed in the stimulable phosphor sheet 15 were sequentially irradiated with the laser beam 24 emitted from the fourth laser stimulating ray source 55, the stimulable phosphor layer regions 17 included in a second line of the stimulable phosphor layer regions 17 formed in the stimulable phosphor sheet 15 are sequentially irradiated with the laser beam 24 emitted from the fourth laser stimulating ray source 55, thereby exciting stimulable phosphor contained in the stimulable phosphor layer regions 17 included in the second line and stimulated emission 45 released from the stimulable phosphor layer regions 17 is sequentially and photoelectrically detected by the photomultiplier 50.

Analog data produced by photoelectrically detecting stimulated emission 45 with the photomultiplier 50 are converted by an A/D converter 53 into digital data and the digital data are fed to a data processing apparatus 54.

When all of the stimulable phosphor layer regions 17 formed in the support 11 of the stimulable phosphor sheet 15 have been scanned with the laser beam 24 released from the fourth laser stimulating ray source 55 to excite stimulable phosphor contained in the stimulable phosphor layer regions 17 and biochemical analysis data produced from chemiluminescence data recorded in the stimulable phosphor layer regions 17 formed in the support 11 of the stimulable phosphor sheet 15 by photoelectrically detecting stimulated emission 45 released from the stimulable phosphor layer regions 17 with the photomultiplier 50 to produce analog data and digitizing the analog data by the A/D converter 53 have been forwarded to the data processing apparatus 54, the control unit 70 outputs a drive stop signal to the fourth laser stimulating ray source 55, thereby turning it off.

As described above, chemiluminescence data recorded in a number of the stimulable phosphor layer regions 17 of the stimulable phosphor sheet 15 are read by the scanner to produce biochemical analysis data.

According to this embodiment, when a number of the stimulable phosphor layer regions 12 formed in the support 11 of the stimulable phosphor sheet 10 are exposed to a radioactive labeling substance selectively contained in a number of the absorptive regions 4 formed in the substrate 2 of the biochemical analysis unit 1, since a number of the absorptive regions 4 of the biochemical analysis unit 1 are formed spaced apart from each other in the substrate 2 made of stainless steel and the substrate 2 made of stainless steel capable of attenuating radiation energy is present around each of the absorptive regions 4, electron beams (β rays) released from the radioactive labeling substance contained in a particular absorptive region 4 of the biochemical analysis unit 1 can be efficiently prevented from scattering in the substrate 2 of the biochemical analysis unit 1 and entering stimulable phosphor layer regions 12 next to the corresponding stimulable phosphor layer region 12. Therefore, it is possible to effectively prevent noise caused by exposing a particular stimulable phosphor layer region 12 to be exposed to the radioactive labeling substance contained in the corresponding absorptive region 4 to electron beams (β rays) released from the radioactive labeling substance contained in the absorptive regions 4 next to the corresponding absorptive region 4 from being generated in biochemical analysis data and to produce biochemical analysis data having an excellent characteristic.

Further, although electron beams (β rays) released from the radioactive labeling substance contained in an area of the absorptive region 4 which does not directly face the corresponding stimulable phosphor layer region 12 may impinge onto stimulable phosphor layer regions next to the corresponding stimulable phosphor layer region 12, according to this embodiment, since a number of the stimulable phosphor layer regions 12 are formed in the support 11 of the stimulable phosphor sheet 10 so that the average diameter Dp thereof is equal to a half of the average diameter Dm of a number of the absorptive regions formed in the substrate 2 of the biochemical analysis unit 1 and the stimulable phosphor sheet 10 is superposed on the biochemical analysis unit 1 so that a circular area of each absorptive region 4 equal to a quarter of its total area directly faces the corresponding stimulable phosphor layer region 12, even if electron beams (β rays) released from the radioactive labeling substance contained in an area of the absorptive region 4 which does not directly face the corresponding stimulable phosphor layer region 12 impinge onto stimulable phosphor layer regions next to the corresponding stimulable phosphor layer region 12, the amount of the electron beams (β rays) is less than a tolerance value and, therefore, it is possible to prevent degradation of the quantitative characteristic of biochemical analysis data produced by irradiating the exposed stimulable phosphor layer regions 12 with a stimulating ray to excite stimulable phosphor contained in the stimulable phosphor layer regions 12 and photoelectrically detecting stimulated emission released from the stimulable phosphor. Accordingly, it is possible to effectively prevent noise caused by exposing a particular stimulable phosphor layer region 12 to be exposed to the radioactive labeling substance contained in the corresponding absorptive region 4 to electron beams (β rays) released from the radioactive labeling substance contained in the absorptive regions 4 next to the corresponding absorptive region 4 from being generated in biochemical analysis data and to produce biochemical analysis data having an excellent characteristic.

Furthermore, according to this embodiment, since the support 11 of the stimulable phosphor sheet 10 is made of stainless steel and is capable of attenuating radiation energy, electron beams (β rays) released from the radioactive labeling substance contained in an area of the absorptive region 4 which does not directly face the corresponding stimulable phosphor layer region 12 can be prevented from entering stimulable phosphor layer regions 12 next to the corresponding stimulable phosphor layer region 12, and, therefore, it is possible to expose each of the stimulable phosphor layer regions 12 to only electron beams (β rays) released from the radioactive labeling substance contained in the corresponding absorptive region 4 of the biochemical analysis unit 1. Accordingly, it is possible to effectively prevent noise caused by exposing a particular stimulable phosphor layer region 12 to be exposed to the radioactive labeling substance contained in the corresponding absorptive region 4 to electron beams (β rays) released from the radioactive labeling substance contained in the absorptive regions 4 next to the corresponding absorptive region 4 from being generated in biochemical analysis data and to produce biochemical analysis data having an excellent characteristic.

Moreover, according to this embodiment, when a number of the stimulable phosphor layer regions 17 formed in the support 11 of the stimulable phosphor sheet 15 are exposed to chemiluminescence emission released from a number of the absorptive regions 4 formed in the substrate 2 of the biochemical analysis unit 1, since a number of the absorptive regions 4 of the biochemical analysis unit 1 are formed spaced apart from each other in the substrate 2 made of stainless steel and the substrate 2 made of stainless steel capable of attenuating light energy is present around each of the absorptive regions 4, chemiluminescence emission released from a particular absorptive region 4 of the biochemical analysis unit 1 can be efficiently prevented from scattering in the substrate 2 of the biochemical analysis unit 1 and entering stimulable phosphor layer regions 17 next to the corresponding stimulable phosphor layer region 17. Therefore, it is possible to effectively prevent noise caused by exposing a particular stimulable phosphor layer region 17 to be exposed to the chemiluminescence emission released from the corresponding absorptive region 4 to chemiluminescence emission released from the absorptive regions 4 next to the corresponding absorptive region 4 from being generated in biochemical analysis data and to produce biochemical analysis data having an excellent characteristic.

Further, although chemiluminescence emission released from an area of the absorptive region 4 which does not directly face the corresponding stimulable phosphor layer region 17 may impinge onto stimulable phosphor layer regions 17 next to the corresponding stimulable phosphor layer region 17, according to this embodiment, since a number of the stimulable phosphor layer regions 17 are formed in the support 11 of the stimulable phosphor sheet 10 so that the average diameter Dp thereof is equal to a half of the average diameter Dm of a number of the absorptive regions 4 formed in the substrate 2 of the biochemical analysis unit 1 and the stimulable phosphor sheet 15 is superposed on the biochemical analysis unit 1 so that a circular area of each absorptive region 4 equal to a quarter of its total area directly faces the corresponding stimulable phosphor layer region 17, even if chemiluminescence emission released from an area of the absorptive region 4 which does not directly face the corresponding stimulable phosphor layer region 17 impinges onto stimulable phosphor layer regions 17 next to the corresponding stimulable phosphor layer region 17, the amount of the chemiluminescence emission is less than a tolerance value and, therefore, it is possible to prevent degradation of the quantitative characteristic of biochemical analysis data produced by irradiating the exposed stimulable phosphor layer regions 17 with a stimulating ray to excite stimulable phosphor contained in the stimulable phosphor layer regions 17 and photoelectrically detecting stimulated emission released from the stimulable phosphor. Accordingly, it is possible to effectively prevent noise caused by exposing a particular stimulable phosphor layer region 17 to be exposed to the chemiluminescence emission released from the corresponding absorptive region 4 to chemiluminescence emission released from the absorptive regions 4 next to the corresponding absorptive region 4 from being generated in biochemical analysis data and to produce biochemical analysis data having an excellent characteristic.

Furthermore, according to this embodiment, since the support 11 of the stimulable phosphor sheet 12 is made of stainless steel and is capable of attenuating radiation energy, chemiluminescence emission released from an area of the absorptive region 4 which does not directly face the corresponding stimulable phosphor layer region 17 can be prevented from entering stimulable phosphor layer regions 17 next to the corresponding stimulable phosphor layer region 17, and, therefore, it is possible to expose each of the stimulable phosphor layer regions 17 to only chemiluminescence emission released from the corresponding absorptive region 4 of the biochemical analysis unit 1.

Moreover, according to this embodiment, since the support 11 of the stimulable phosphor sheet 15 is made of stainless steel and is capable of attenuating light energy, chemiluminescence emission released from an area of the absorptive region 4 which does not directly face the corresponding stimulable phosphor layer region 17 can be prevented from entering stimulable phosphor layer regions 17 next to the corresponding stimulable phosphor layer region 17, and, therefore, it is possible to expose each of the stimulable phosphor layer regions 17 to only chemiluminescence emission released from the corresponding absorptive region 4 of the biochemical analysis unit 1. Accordingly, it is possible to effectively prevent noise caused by exposing a particular stimulable phosphor layer region 17 to be exposed to chemiluminescence emission released from the corresponding absorptive region 4 to chemiluminescence emission released from the absorptive regions 4 next to the corresponding absorptive region 4 from being generated in biochemical analysis data and to produce biochemical analysis data having an excellent characteristic.

Figure 18:
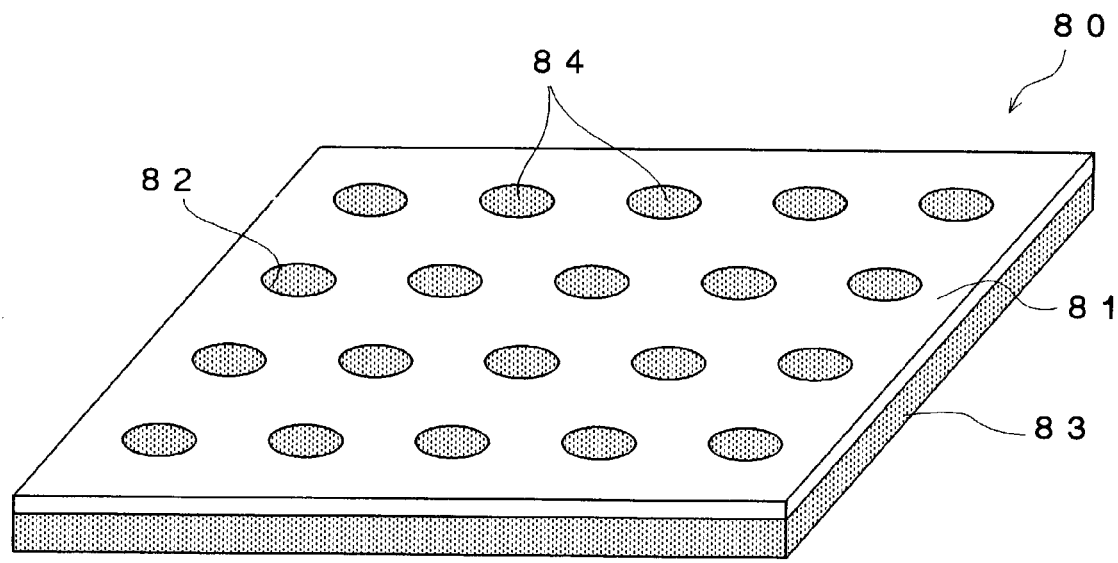
FIG. 18 is a schematic perspective view showing a biochemical analysis unit which is a further preferred embodiment of the present invention.

FIG. 18 is a schematic perspective view showing a biochemical analysis unit which is a further preferred embodiment of the present invention.

As shown in FIG. 18, a biochemical analysis unit 80 according to this embodiment includes a substrate 81 made of stainless steel and formed with a number of substantially circular through-holes 82 in a regular pattern and a number of absorptive regions 84 are dot-like formed in a regular pattern by pressing an absorptive membrane 83 formed of nylon-6 into a number of the through-holes 82 formed in the substrate 81 using the calender processing apparatus.

Although not accurately shown in FIG. 18, in this embodiment, about 10,000 substantially circular absorptive regions 84 having an average diameter Dm are regularly formed in the biochemical analysis unit 80 at a density of about 5,000 per $cm^2$.

In this embodiment, the biochemical analysis unit 80 is produced by pressing the absorptive membrane 83 into a number of the through-holes 82 formed in the substrate 81 so that the surfaces of the absorptive regions 84 and the surface of the substrate 81 lie at the same height level.

In this embodiment, similarly to the biochemical analysis unit 1, a solution containing specific binding substances such as cDNAs is spotted using the spotting device 5 onto a number of the absorptive regions 84 formed in the biochemical analysis unit 80 and the specific binding substances are absorbed in a number of the absorptive regions 84.

Since a number of the absorptive regions 84 of the biochemical analysis unit 80 shown in FIG. 18 are formed by pressing the absorptive membrane 83 into a number of the through-holes 82 formed in the substrate 81, cavities in the absorptive membrane 83 have been eliminated by the pressing operation in regions between neighboring absorptive regions 84. Therefore, a solution of specific binding substances spotted in the absorptive regions 84 can be effectively prevented from permeating the absorptive membrane 83 and the specific binding substances are absorbed only in the absorptive regions 84.

Further, as shown in FIG. 3, the biochemical analysis unit 80 is set in the hybridization reaction vessel 8 accommodating a hybridization reaction solution 9 containing a substance derived from a living organism and labeled with a radioactive labeling substance, a substance derived from a living organism and labeled with a labeling substance which generates chemiluminescence emission when it contacts a chemiluminescent substrate and a substance derived from a living organism and labeled with a fluorescent substance such as a fluorescent dye and specific binding substances absorbed in a number of the absorptive regions 84 of the biochemical analysis unit 80 are selectively hybridized with a substance derived from a living organism, labeled with a radioactive labeling substance and contained in the hybridization reaction solution 9, a substance derived from a living organism, labeled with a labeling substance which generates chemiluminescence emission when it contacts a chemiluminescent substrate and contained in the hybridization reaction solution 9 and a substance derived from a living organism, labeled with a fluorescent substance such as a fluorescent dye and contained in the hybridization reaction solution 9.

Thus, radiation data, chemiluminescence data and fluorescence data are recorded in a number of the absorptive regions 84 formed in the biochemical analysis unit 80.

Similarly to the previous embodiment, fluorescence data recorded in a number of the absorptive regions 84 of the biochemical analysis unit 80 are read by the scanner shown in FIGS. 6 to 13 to produce biochemical analysis data.

On the other hand, radiation data recorded in a number of the absorptive regions 84 of the biochemical analysis unit 80 are transferred onto a stimulable phosphor sheet and chemiluminescence data recorded in a number of the absorptive regions 84 of the biochemical analysis unit 80 are transferred onto another stimulable phosphor sheet.

Figure 19:
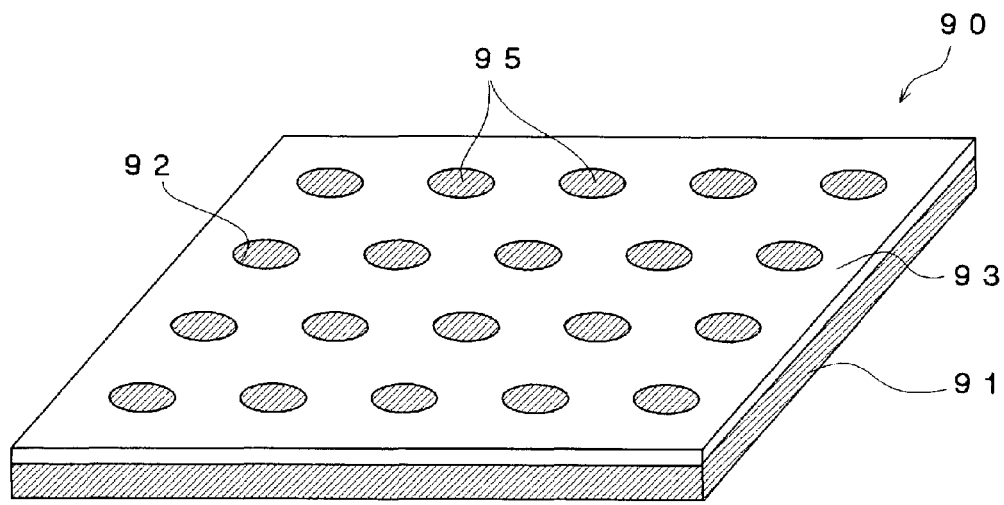
FIG. 19 is a schematic perspective view showing a stimulable phosphor sheet which is a further preferred aspect of the present invention.

FIG. 19 is a schematic perspective view showing a stimulable phosphor sheet onto which radiation data are to be transferred.

As shown in FIG. 19, a stimulable phosphor sheet 90 according to this embodiment includes a stimulable phosphor membrane 91 containing BaFX system stimulable phosphor (where X is at least one halogen atom selected from the group consisting of Cl, Br and I) capable of absorbing and storing radiation energy and a binder and a support 93 made of stainless steel and regularly formed with a number of through-holes 92, and the stimulable phosphor membrane 91 is pressed into a number of the through-holes 92 formed in the support 93 using a calender processing apparatus (not shown), thereby dot-like forming a number of stimulable phosphor layer regions 95 at positions corresponding to those of a number of the through-holes 92 of the support 93.

A number of the through-holes 92 are formed in the support 93 in the same pattern as that of a number of the absorptive regions 84 in the substrate 81 of the biochemical analysis unit 80 shown in FIG. 18 and a number of the stimulable phosphor layer regions 95 are formed so as to have an average diameter Dp.

In this embodiment, a number of the stimulable phosphor layer regions 95 are formed in the support 93 of the stimulable phosphor sheet 90 so that the average diameter Dp thereof is equal to a half of the average diameter Dm of a number of the absorptive regions 84 formed in the substrate 81 of the biochemical analysis unit 80.

Therefore, although not accurately shown in FIG. 19, in this embodiment, about 10,000 substantially circular stimulable phosphor layer regions 95 having the average diameter Dp are dot-like formed at a density of about 5,000 per cm² in the stimulable phosphor sheet 90 in the same regular pattern as that of a number of the absorptive regions 84 formed in the substrate 81 of the biochemical analysis unit 80.

In this embodiment, the stimulable phosphor sheet 90 is prepared by pressing the stimulable phosphor membrane 91 into a number of the through-holes 92 of the support 93 in such a manner that the surface of the support 93 and the surfaces of a number of the stimulable phosphor layer regions 95 lie at the same height level.

Figure 20:
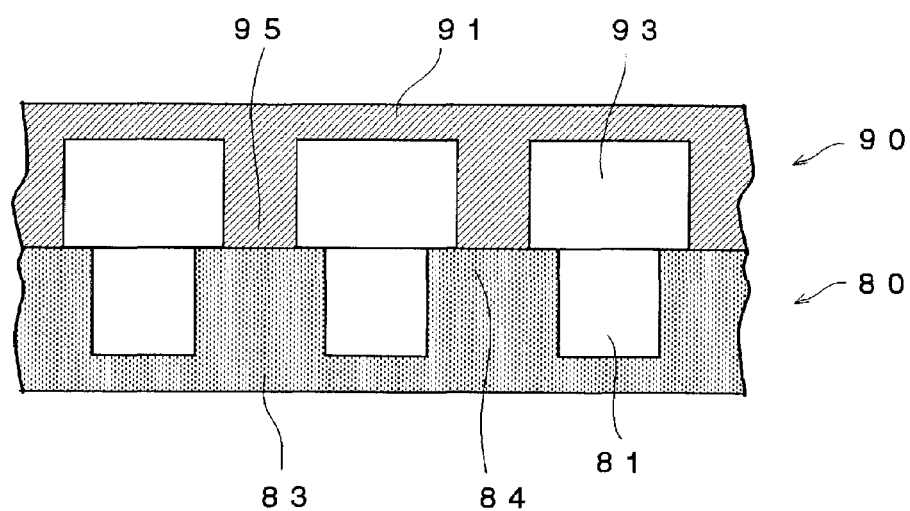
FIG. 20 is a schematic cross sectional view showing a method for exposing a number of stimulable phosphor layer regions formed in a support of a stimulable phosphor sheet shown in FIG. 19 to a radioactive labeling substance contained in a number of absorptive regions formed in a substrate of a biochemical analysis unit shown in FIG. 18.

FIG. 20 is a schematic cross sectional view showing a method for exposing a number of the stimulable phosphor layer regions 95 formed in the stimulable phosphor sheet 90 to a radioactive labeling substance selectively contained in a number of the absorptive layers 84 formed in the biochemical analysis unit 80.

As shown in FIG. 20, when the stimulable phosphor layer regions 95 of a stimulable phosphor sheet 90 are to be exposed, the stimulable phosphor sheet 90 is superposed on the biochemical analysis unit 80 in such a manner that a number of the absorptive regions 84 formed in the biochemical analysis unit 80 face the corresponding stimulable phosphor layer regions 95 formed in the stimulable phosphor sheet 90.

In this embodiment, since the biochemical analysis unit 80 is formed by pressing the absorptive membrane 83 into a number of the through-holes 82 formed in the substrate 81 made of stainless steel, the biochemical analysis unit 80 does not stretch or shrink when it is subjected to liquid processing such as hybridization and, therefore, it is possible to easily and accurately superpose the stimulable phosphor sheet 90 on the biochemical analysis unit 80 so that each of the stimulable phosphor layer regions 95 formed in the stimulable phosphor sheet 90 accurately faces the corresponding absorptive region 84 formed in the biochemical analysis unit 80, thereby exposing a number of the stimulable phosphor layer regions 95.

In this manner, each of the stimulable phosphor layer regions 95 formed in the stimulable phosphor sheet 90 is kept to face the corresponding absorptive region 84 formed in the biochemical analysis unit 80 for a predetermined time period, whereby a number of the stimulable phosphor layer regions 95 formed in the stimulable phosphor sheet 90 are exposed to the radioactive labeling substance selectively contained in a number of the absorptive regions 84 formed in the biochemical analysis unit 80.

In this embodiment, when a number of the stimulable phosphor layer regions 95 formed in the stimulable phosphor sheet 90 are exposed to a radioactive labeling substance selectively contained in a number of the absorptive regions 84 formed in the biochemical analysis unit 80, since a number of the absorptive regions 84 of the biochemical analysis unit 80 are formed by pressing the absorptive membrane 83 into a number of the through-holes 82 formed to be spaced apart from each other in the substrate 81 made of stainless steel and the substrate 81 made of stainless steel capable of attenuating radiation energy is present around each of the absorptive regions 84, electron beams (β rays) released from the radioactive labeling substance contained in a particular absorptive region 84 of the biochemical analysis unit 80 can be efficiently prevented from scattering in the substrate 81 of the biochemical analysis unit 80 and entering stimulable phosphor layer regions 95 next to the corresponding stimulable phosphor layer region 95. Therefore, it is possible to effectively prevent noise caused by exposing a particular stimulable phosphor layer region 95 to be exposed to the radioactive labeling substance contained in the corresponding absorptive region 84 to electron beams (β rays) released from the radioactive labeling substance contained in the absorptive regions 84 next to the corresponding absorptive region 84 from being generated in biochemical analysis data.

Further, although electron beams (β rays) released from the radioactive labeling substance contained in an area of an absorptive region 84 which does not directly face the corresponding stimulable phosphor layer region 95 may impinge onto stimulable phosphor layer regions next to the corresponding stimulable phosphor layer region 95, according to this embodiment, since a number of the stimulable phosphor layer regions 95 are formed in the stimulable phosphor sheet 90 so that the average diameter Dp thereof is equal to a half of the average diameter Dm of a number of the absorptive regions 84 formed in the biochemical analysis unit 80 and the stimulable phosphor sheet 90 is superposed on the biochemical analysis unit 80 so that a circular area of each absorptive region 84 equal to a quarter of its total area directly faces the corresponding stimulable phosphor layer region 95, even if electron beams (β rays) released from the radioactive labeling substance contained in an area of the absorptive region 84 which does not directly face the corresponding stimulable phosphor layer region 95 impinge onto stimulable phosphor layer regions 95 next to the corresponding stimulable phosphor layer region 95, the amount of the electron beams (β rays) can be controlled to less than a tolerance value and, therefore, it is possible to effectively prevent noise caused by exposing a particular stimulable phosphor layer region 95 to be exposed to the radioactive labeling substance contained in the corresponding absorptive region 84 to electron beams (β rays) released from the radioactive labeling substance contained in the absorptive regions 84 next to the corresponding absorptive region 84 from being generated in biochemical analysis data and to produce biochemical analysis data having an excellent characteristic.

Furthermore, in this embodiment, since the support 93 of the stimulable phosphor sheet 90 is made of stainless steel and is capable of attenuating radiation energy, electron beams (β rays) released from the radioactive labeling substance contained in an area of the absorptive region 84 which does not directly face the corresponding stimulable phosphor layer region 95 can be prevented from entering stimulable phosphor layer regions 95 next to the corresponding stimulable phosphor layer region 95, and, therefore, it is possible to expose each of the stimulable phosphor layer regions 95 to only electron beams (β rays) released from the radioactive labeling substance contained in the corresponding absorptive region 84 of the biochemical analysis unit 80.

In this manner, radiation data are recorded in a number of the stimulable phosphor layer regions 95 formed in the stimulable phosphor sheet 90 and similarly to the above described embodiment, the radiation data recorded in a number of the stimulable phosphor layer regions 95 formed in the stimulable phosphor sheet 90 are read by the scanner shown in FIGS. 6 to 13 to produce biochemical analysis data.

To the contrary, chemiluminescence data recorded in a number of the absorptive regions 84 formed in the biochemical analysis unit 80 are transferred onto a stimulable phosphor sheet.

Figure 21:
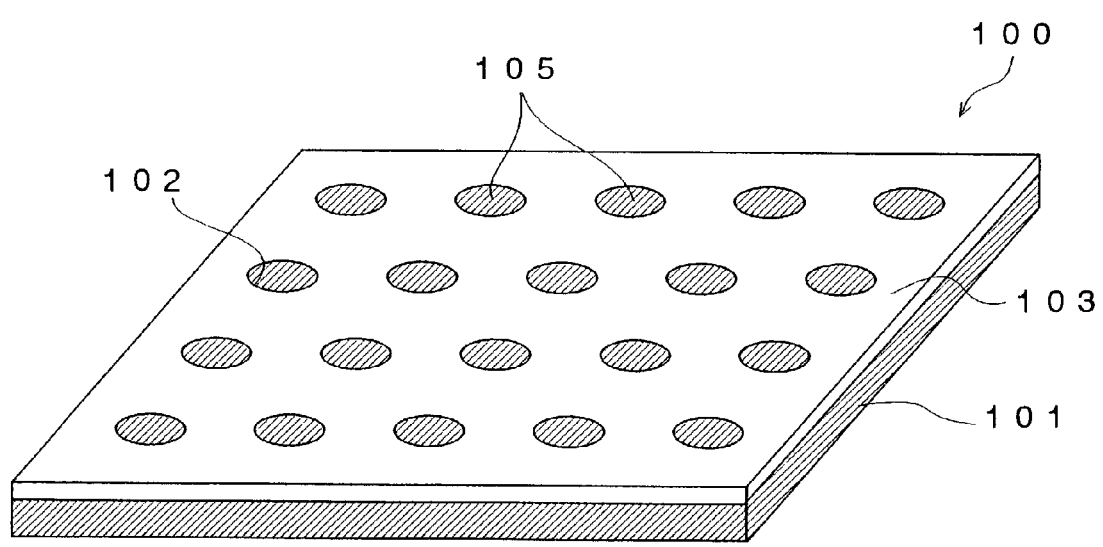
FIG. 21 is a schematic perspective view showing another stimulable phosphor sheet onto which chemiluminescence data are to be transferred, which is a further preferred embodiment of the present invention.

FIG. 21 is a schematic perspective view showing another stimulable phosphor sheet onto which chemiluminescence data are to be transferred, which is a further preferred embodiment of the present invention.

As shown in FIG. 21, a stimulable phosphor sheet 100 has the same configuration as that of the stimulable phosphor sheet 90 shown in FIG. 19 except that a stimulable phosphor membrane 101 contains SrS system stimulable phosphor capable of absorbing and storing light energy and a binder and that a number of stimulable phosphor layer regions 105 are dot-like formed by pressing the stimulable phosphor membrane 101 into a number of through-holes 102 formed in a support 103 made of stainless steel.

A number of the through-holes 102 are formed in the support 103 in the same pattern as that of a number of the absorptive regions 84 in the substrate 81 of the biochemical analysis unit 80 shown in FIG. 18 and a number of the stimulable phosphor layer regions 105 are formed so as to have an average diameter Dp.

In this embodiment, a number of the stimulable phosphor layer regions 105 are formed in the stimulable phosphor sheet 100 so that the average diameter Dp thereof is equal to a half of the average diameter Dm of a number of the absorptive regions 84 formed in the substrate 81 of the biochemical analysis unit 80.

Therefore, although not accurately shown in FIG. 21, in this embodiment, about 10,000 substantially circular stimulable phosphor layer regions 105 having the average diameter Dp are dot-like formed at a density of about 5,000 per $cm^2$ in the stimulable phosphor sheet 100 in the same regular pattern as that of a number of the absorptive regions 84 formed in the substrate 81 of the biochemical analysis unit 80.

In this embodiment, the stimulable phosphor sheet 100 is prepared by pressing the stimulable phosphor membrane 101 into a number of the through-holes 102 of the support 103 in such a manner that the surface of the support 103 and the surfaces of a number of the stimulable phosphor layer regions 105 lie at the same height level.

Chemiluminescence data recorded in a number of the absorptive regions 84 formed in the biochemical analysis unit 80 are transferred onto a number of the stimulable phosphor layer regions 105 of the stimulable phosphor sheet 100 shown in FIG. 21.

When chemiluminescence data recorded in a number of the absorptive regions 84 of the biochemical analysis unit 80 are to be transferred onto a number of the stimulable phosphor layer regions 105 of the stimulable phosphor 100, a number of the absorptive regions 84 of the biochemical analysis unit 80 are first brought into contact with a chemiluminescent substrate.

As a result, chemiluminescence emission in a wavelength of visible light is selectively released from a number of the absorptive regions 84 of the biochemical analysis unit 80.

The stimulable phosphor sheet 100 is then superposed on the biochemical analysis unit 80 formed with a number of the absorptive regions 84 selectively releasing chemiluminescence emission in such a manner that a number of the stimulable phosphor layer regions 105 formed in the stimulable phosphor sheet 100 face the corresponding absorptive regions 84 formed in the biochemical analysis unit 80.

In this manner, each of the stimulable phosphor layer regions 105 formed in the stimulable phosphor sheet 100 is kept to face the corresponding absorptive region 84 formed in the biochemical analysis unit 80 for a predetermined time period, whereby a number of the stimulable phosphor layer regions 105 formed in the stimulable phosphor sheet 100 are exposed to chemiluminescence emission released from a number of the absorptive regions 84 formed in the biochemical analysis unit 80.

In this embodiment, when a number of the stimulable phosphor layer regions 105 formed in the stimulable phosphor sheet 100 are exposed to chemiluminescence emission released from a number of the absorptive regions 84 formed in the biochemical analysis unit 80, since a number of the absorptive regions 84 of the biochemical analysis unit 1 are formed by pressing the absorptive membrane 83 into a number of the through-holes 82 formed to be spaced apart from each other in the substrate 81 made of stainless steel and the substrate 81 made of stainless steel capable of attenuating light energy is present around each of the absorptive regions 84, chemiluminescence emission released from a particular absorptive region 84 of the biochemical analysis unit 80 can be efficiently prevented from scattering in the biochemical analysis unit 80 and entering stimulable phosphor layer regions 105 next to the corresponding stimulable phosphor layer region 105. Therefore, it is possible to effectively prevent noise caused by exposing a particular stimulable phosphor layer region 105 to be exposed to the chemiluminescence emission released from the corresponding absorptive region 84 to chemiluminescence emission released from the absorptive regions 84 next to the corresponding absorptive region 84 from being generated in biochemical analysis data.

Further, although chemiluminescence emission released from an area of an absorptive region 84 which does not directly face the corresponding stimulable phosphor layer region 105 may impinge onto stimulable phosphor layer regions 105 next to the corresponding stimulable phosphor layer region 105, in this embodiment, since a number of the stimulable phosphor layer regions 105 are formed in the stimulable phosphor sheet 100 so that the average diameter Dp thereof is equal to a half of the average diameter Dm of a number of the absorptive regions 84 formed in the biochemical analysis unit 80 and the stimulable phosphor sheet 100 is superposed on the biochemical analysis unit 80 so that a circular area of each absorptive region 84 equal to a quarter of its total area directly faces the corresponding stimulable phosphor layer region 105, even if chemiluminescence emission released from an area of the absorptive region 84 which does not directly face the corresponding stimulable phosphor layer region 105 impinges onto stimulable phosphor layer regions 105 next to the corresponding stimulable phosphor layer region 105, the amount of the chemiluminescence emission can be controlled to less than a tolerance value and, therefore, it is possible to effectively prevent noise caused by exposing a particular stimulable phosphor layer region 105 to be exposed to the chemiluminescence emission released from the corresponding absorptive region 84 to chemiluminescence emission released from the absorptive regions 84 next to the corresponding absorptive region 84 from being generated in biochemical analysis data and to produce biochemical analysis data having an excellent characteristic.

Furthermore, in this embodiment, since the support 103 of the stimulable phosphor sheet 100 is made of stainless steel and is capable of attenuating radiation energy, chemiluminescence emission released from an area of the absorptive region 84 which does not directly face the corresponding stimulable phosphor layer region 105 can be prevented from entering stimulable phosphor layer regions 105 next to the corresponding stimulable phosphor layer region 105, and, therefore, it is possible to expose each of the stimulable phosphor layer regions 105 to only chemiluminescence emission released from the corresponding absorptive region 84 of the biochemical analysis unit 80.

Thus, chemiluminescence data are recorded in a number of the stimulable phosphor layer regions 105 formed in the stimulable phosphor sheet 100 and similarly to the above described embodiment, the chemiluminescence data recorded in a number of the stimulable phosphor layer regions 105 formed in the stimulable phosphor sheet 100 are read by the scanner shown in FIGS. 15 to 17 to produce biochemical analysis data.

According to this embodiment, since a number of the stimulable phosphor layer regions 95 are formed by pressing the stimulable phosphor membrane 91 into a number of the through-holes 92 formed in the support 93 made of stainless steel in the same regular pattern as that of a number of the absorptive regions 84 formed in the substrate 81 made of stainless steel of the biochemical analysis unit 80 so that the average diameter Dp thereof is equal to the average diameter Dm of a number of the absorptive regions 84 formed in the substrate 81 of the biochemical analysis unit 80, similarly to the above described embodiment, it is possible to selectively expose stimulable phosphor contained in only the stimulable phosphor layer region 95 each of the absorptive regions 84 faces to the electron beams (β rays) released from the radioactive labeling substance contained in each of the absorptive regions 84 and to produce biochemical analysis data having an excellent characteristic.

Further, according to this embodiment, since a number of the stimulable phosphor layer regions 105 are formed by pressing the stimulable phosphor membrane 101 into a number of the through-holes 102 formed in the support 103 made of stainless steel in the same regular pattern as that of a number of the absorptive regions 84 formed in the substrate 81 made of stainless steel of the biochemical analysis unit 80 so that the average diameter Dp thereof is equal to the average diameter Dm of a number of the absorptive regions 84 formed in the substrate 81 of the biochemical analysis unit 80, similarly to the above described embodiment, it is possible to selectively expose stimulable phosphor contained in only the stimulable phosphor layer region 105 each of the absorptive regions 84 faces to the chemiluminescence emission released from each of the absorptive regions 84 and to produce biochemical analysis data having an excellent characteristic.

The present invention has thus been shown and described with reference to specific embodiments. However, it should be noted that the present invention is in no way limited to the details of the described arrangements but changes and modifications may be made without departing from the scope of the appended claims.

For example, in the above described embodiments, about 10,000 absorptive regions 4, 84 having an average diameter Dm are formed in the biochemical analysis unit 1, 80 in a regular pattern at a density of about 5,000 per $cm^2$ and about 10,000 stimulable phosphor layer regions 12, 17, 95, 105 having an average diameter Dp are formed in the stimulable phosphor sheet 10, 15, 90, 100 at a density of about 5,000 per $cm^2$ in the same regular pattern as that of a number of the absorptive regions 4, 84 formed in the biochemical analysis unit 1, 80 so that the average diameter Dp of the stimulable phosphor layer regions 12, 17, 95, 105 is equal to a half of the average diameter Dm of the absorptive regions 4, 84. However, it is not absolutely necessary to form a number of the stimulable phosphor layer regions 12, 17, 95, 105 so that the average diameter Dp thereof is equal to a half of the average diameter Dm of the absorptive regions 4, 84 but it is sufficient for a number of the stimulable phosphor layer regions 12, 17, 95, 105 to be formed so that the average diameter Dp thereof is equal to or lager than a quarter of the average diameter Dm of the absorptive regions 4, 84. Preferably, a number of the the stimulable phosphor layer regions 12, 17, 95, 105 are formed so that the average diameter Dp thereof is equal to or lager than ½ times the average diameter Dm of the absorptive regions 4, 84 and more preferably, a number of the stimulable phosphor layer regions 12, 17, 95, 105 are formed so that the average diameter Dp thereof is equal to or lager than the average diameter Dm of the absorptive regions 4, 84.

Further, in the above described embodiments, about 10,000 absorptive regions 4, 84 having an average diameter Dm are formed in the biochemical analysis unit 1, 80 in a regular pattern at a density of about 5,000 per $cm^2$ and about 10,000 stimulable phosphor layer regions 12, 17, 95, 105 having an average diameter Dp are formed in the stimulable phosphor sheet 10, 15, 90, 100 at a density of about 5,000 per $cm^2$ in the same regular pattern as that of a number of the absorptive regions 4, 84 formed in the biochemical analysis unit 1, 80 so that the average diameter Dp of the stimulable phosphor layer regions 12, 17, 95, 105 is equal to a half of the average diameter Dm of the absorptive regions 4, 84. However, the shape of each of the absorptive regions 4, 84 and each of the stimulable phosphor layer regions 12, 17, 95, 105 is not limited to substantially a circular shape but may be formed in an arbitrary shape, for example, a rectangular shape. In the case where a number of the absorptive regions 4, 84 and a number of the stimulable phosphor layer regions 12, 17, 95, 105 are not formed substantially circular, preferably, a number of the stimulable phosphor layer regions 12, 17, 95, 105 are formed so that the average area Sp thereof is equal to or larger than a quarter of the average area Sm of a number of the absorptive regions 4, 84, more preferably, a number of the stimulable phosphor layer regions 12, 17, 95, 105 are formed so that the average area Sp thereof is equal to or larger than a half of the average area Sm of a number of the absorptive regions 4, 84 and most preferably, a number of the stimulable phosphor layer regions 12, 17, 95, 105 are formed so that the average area Sp thereof is equal to or larger than the average area Sm of a number of the absorptive regions 4, 84.

Moreover, although in the above described embodiments, about 10,000 absorptive regions 4, 84 having an average diameter Dm are formed in the biochemical analysis unit 1, 80 in a regular pattern at a density of about 5,000 per $cm^2$, the number or size of the absorptive regions 4, 84 may be arbitrarily selected in accordance with the purpose. Preferably, 10 or more of the absorptive regions 4, 84 having a size of 5 $cm^2$ or less are formed in the biochemical analysis unit 1, 80 at a density of 10/$cm^2$ or greater.

Further, in the above described embodiments, although about 10,000 absorptive regions 4, 84 having an average diameter Dm are formed in the biochemical analysis unit 1, 80 in a regular pattern at a density of about 5,000 per $cm^2$, it is not absolutely necessary to form a number of the absorptive regions 4, 84 in the biochemical analysis unit 1, 80 in a regular pattern.

Furthermore, in the above described embodiments, as specific binding substances, cDNAs each of which has a known base sequence and is different from the others are used. However, specific binding substances usable in the present invention are not limited to cDNAs but all specific binding substances capable of specifically binding with a substance derived from a living organism such as a cell, virus, hormone, tumor marker, enzyme, antibody, antigen, abzyme, other protein, a nuclear acid, cDNA, DNA, RNA or the like and whose sequence, base length, composition and the like are known, can be employed in the present invention as a specific binding substance.

Further, the biochemical analysis unit 1 includes a number of the absorptive regions 4 formed by charging nylon-6 in a number of the through-holes 3 formed in the substrate 2 made of stainless steel in the embodiment shown in FIG. 1 and a number of the absorptive regions 84 formed by pressing the absorptive membrane 83 into a number of the through-holes 82 formed in the substrate 2 made of stainless steel in the embodiment shown in FIG. 18. However, it is not absolutely necessary to form a number of the absorptive regions 4, 84 of the biochemical analysis unit 1, 80 of nylon-6 but a number of the absorptive regions 4, 84 of the biochemical analysis unit 1, 80 may be formed of other absorptive material. A porous material or a fiber material may be preferably used as the absorptive material for forming a number of the absorptive regions 4, 84 of the biochemical analysis unit 1, 80 and a number of the absorptive regions 4, 84 of the biochemical analysis unit 1, 80 may be formed by combining a porous material and a fiber material. A porous material for forming a number of the absorptive regions 4, 84 of the biochemical analysis unit 1, 80 may be any type of an organic material or an inorganic material and may be an organic/inorganic composite material. An organic porous material used for forming a number of the absorptive regions 4, 84 of the biochemical analysis unit 1, 80 is not particularly limited but a carbon porous material such as an activated carbon or a porous material capable of forming a membrane filter can be preferably used. Illustrative examples of porous materials capable of forming a membrane filter include nylons such as nylon-6, nylon-6,6, nylon-4,10; cellulose derivatives such as nitrocellulose, acetyl cellulose, butyric-acetyl cellulose; collagen; alginic acids such as alginic acid, calcium alginate, alginic acid/ poly-L-lysine polyionic complex; polyolefins such as polyethylene, polypropylene; polyvinyl chloride; polyvinylidene chloride; polyfluoride such as polyvinylidene fluoride, polytetrafluoride; and copolymers or composite materials thereof. An inorganic porous material used for forming a number of the absorptive regions 4, 84 of the biochemical analysis unit 1, 80 is not particularly limited. Illustrative examples of inorganic porous materials preferably usable in the present invention include metals such as platinum, gold, iron, silver, nickel, aluminum and the like; metal oxides such as alumina, silica, titania, zeolite and the like; metal salts such as hydroxy apatite, calcium sulfate and the like; and composite materials thereof A fiber material used for forming a number of the absorptive regions 4, 84 of the biochemical analysis unit 1, 80 is not particularly limited. Illustrative examples of fiber materials preferably usable in the present invention include nylons such as nylon-6, nylon-6,6, nylon-4,10; and cellulose derivatives such as nitrocellulose, acetyl cellulose, butyric-acetyl cellulose.

Furthermore, in the above described embodiments, although the substrate 2, 81 of the biochemical analysis unit 1, 80 is made of stainless steel, it is not absolutely necessary to make the substrate 2, 81 of the biochemical analysis unit 1, 80 of stainless steel but the substrate 2, 81 of the biochemical analysis unit 1, 80 may be made of other kinds of material. A material for forming the substrate 2, 81 of the biochemical analysis unit 1, 80 is not particularly limited insofar as it can attenuate radiation energy and/or light energy. The material usable for forming the substrate 2, 81 of the biochemical analysis unit 1, 80 may be any type of inorganic compound material or organic compound material and a metal material, a ceramic material or a plastic material is preferably used for forming the substrate 2, 81 of the biochemical analysis unit 1, 80. Illustrative examples of inorganic compound materials usable for forming the substrate 2, 81 of the biochemical analysis unit 1, 80 and capable of attenuating radiation energy and/or light energy include metals such as gold, silver, copper, zinc, aluminum, titanium, tantalum, chromium, steel, nickel, cobalt, lead, tin, selenium and the like; alloys such as brass, stainless, bronze and the like; silicon materials such as silicon, amorphous silicon, glass, quartz, silicon carbide, silicon nitride and the like; metal oxides such as aluminum oxide, magnesium oxide, zirconium oxide and the like; and inorganic salts such as tungsten carbide, calcium carbide, calcium sulfate, hydroxy apatite, gallium arsenide and the like. High molecular compounds are preferably used as organic compound material for forming the substrate 2, 81 of the biochemical analysis unit 1, 80 and capable of attenuating radiation energy and/or light energy and illustrative examples thereof include polyolefins such as polyethylene, polypropylene and the like; acrylic resins such as polymethyl methacrylate, polybutylacrylate/polymethyl methacrylate copolymer and the like; polyacrylonitrile; polyvinyl chloride; polyvinylidene chloride; polyvinylidene fluoride; polytetrafluoroethylene; polychlorotrifluoroethylene; polycarbonate; polyesters such as polyethylene naphthalate, polyethylene terephthalate and the like; nylons such as nylon-6, nylon-6, 6, nylon-4, 10 and the like; polyimide; polysulfone; polyphenylene sulfide; silicon resins such as polydiphenyl siloxane and the like; phenol resins such as novolac and the like; epoxy resin; polyurethane; polystyrene, butadienestyrene copolymer; polysaccharides such as cellulose, acetyl cellulose, nitrocellulose, starch, calcium alginate, hydroxypropyl methyl cellulose and the like; chitin; chitosan; urushi (Japanese lacquer); polyamides such as gelatin, collagen, keratin and the like; and copolymers of these high molecular materials. These may be a composite compound, and metal oxide particles, glass fiber or the like may be added thereto as occasion demands. Further, an organic compound material may be blended therewith.

Moreover, although the biochemical analysis unit 1 includes a number of the absorptive regions 4 formed by charging nylon-6 in a number of the through-holes 3 formed in the substrate 2 made of stainless steel in the embodiment shown in FIG. 1 and a number of the absorptive regions 84 formed by pressing the absorptive membrane 83 into a number of the through-holes 82 formed in the substrate 2 made of stainless steel in the embodiment shown in FIG. 18, a number of absorptive regions of a biochemical analysis unit may be formed by charging nylon-6 in a number of recesses formed in a substrate.

Further, although the biochemical analysis unit 1 includes a number of the absorptive regions 4 formed by charging nylon-6 in a number of the through-holes 3 formed in the substrate 2 made of stainless steel in the embodiment shown in FIG. 1 and a number of the absorptive regions 84 formed by pressing the absorptive membrane 83 into a number of the through-holes 82 formed in the substrate 2 made of stainless steel in the embodiment shown in FIG. 18, a number of absorptive regions of a biochemical analysis unit may be formed to be spaced apart from each other by closely contacting a perforated plate formed with a number of through-holes onto one surface of an absorptive substrate.

Furthermore, although the stimulable phosphor sheet 10, 15 includes the support 11 made of stainless steel and regularly formed with a number of the substantially circular through-holes 13 and a number of the stimulable phosphor layer regions 12, 17 are formed by charging stimulable phosphor in a number of the through-holes 13 in the embodiment shown in FIG. 1 and the embodiment shown in FIG. 14, a number of the stimulable phosphor layer regions 12 may be formed by regularly forming a number of recesses in the support 11 instead of a number of the through-holes 13 and charging stimulable phosphor in a number of the recesses.

Moreover, although a number of the stimulable phosphor layer regions 95, 105 are formed by pressing the stimulable phosphor membrane 91, 101 into a number of the through-holes 92, 102 formed in the support 93, 103 made of stainless steel using a calender processing apparatus in the embodiment shown in FIG. 19 and the embodiment shown in FIG. 21, it is not absolutely necessary to press the stimulable phosphor membrane 91, 101 into a number of the through-holes 92, 102 formed in the support 93, 103 using a calender processing apparatus to form a number of the stimulable phosphor layer regions 95, 105 and it is possible to press the stimulable phosphor membrane 91, 101 into a number of the through-holes 92, 102 formed in the support 93, 103 using other means such a heat press apparatus. Further, instead of pressing the stimulable phosphor membrane 91, 101, a number of the stimulable phosphor layer regions 95, 105 of the stimulable phosphor sheet 90, 100 may be formed by charging the stimulable phosphor membrane 91, 101 into a number of through-holes 92, 102 formed in the support 93, 103.

Furthermore, a number of the stimulable phosphor layer regions 12, 17 of the stimulable phosphor sheet 10, 15 are formed by charging stimulable phosphor in a number of the through-holes 13 formed in the support 11 made of stainless steel in the embodiment shown in FIG. 4 and the embodiment shown in FIG. 14 and a number of the stimulable phosphor layer regions 95, 105 of the stimulable phosphor sheet 90, 100 are formed by pressing the stimulable phosphor membrane 91, 101 into a number of the through-holes 92, 102 formed in the support 93, 103 made of stainless steel in the embodiment shown in FIG. 19 and the embodiment shown in FIG. 21. However, it is not absolutely necessary to form the support 11, 93, 103 of the stimulable phosphor sheet 10, 15, 90, 100 of stainless steel and the support 11, 93, 103 of the stimulable phosphor sheet 10, 15, 90, 100 can be made of other material. The support 11, 93, 103 of the stimulable phosphor sheet 10, 15, 90, 100 is preferably made of material capable of attenuating radiation energy and light energy but the material for forming the support 11, 93, 103 of the stimulable phosphor sheet 10, 15, 90, 100 is not particularly limited. The support 11, 93, 103 of the stimulable phosphor sheet 10, 15, 90, 100 can be formed of either inorganic compound material or organic compound material and is preferably formed of a metal material, a ceramic material or a plastic material. Illustrative examples of inorganic compound materials preferably usable for forming the support 11, 93, 103 of the stimulable phosphor sheet 10, 15, 90, 100 include metals such as gold, silver, copper, zinc, aluminum, titanium, tantalum, chromium, steel, nickel, cobalt, lead, tin, selenium and the like; alloys such as brass, stainless, bronze and the like; silicon materials such as silicon, amorphous silicon, glass, quartz, silicon carbide, silicon nitride and the like; metal oxides such as aluminum oxide, magnesium oxide, zirconium oxide and the like; and inorganic salts such as tungsten carbide, calcium carbide, calcium sulfate, hydroxy apatite, gallium arsenide and the like. High molecular compounds are preferably used as organic compound material usable for forming the support 11, 93, 103 of the stimulable phosphor sheet 10, 15, 90, 100 and illustrative examples thereof include polyolefins such as polyethylene, polypropylene and the like; acrylic resins such as polymethyl methacrylate, polybutylacrylate/polymethyl methacrylate copolymer and the like; polyacrylonitrile; polyvinyl chloride; polyvinylidene chloride; polyvinylidene fluoride; polytetrafluoroethylene; polychlorotrifluoroethylene; polycarbonate; polyesters such as polyethylene naphthalate, polyethylene terephthalate and the like; nylons such as nylon-6, nylon-6,6, nylon-4,10 and the like; polyimide; polysulfone; polyphenylene sulfide; silicon resins such as polydiphenyl siloxane and the like; phenol resins such as novolac and the like; epoxy resin; polyurethane; polystyrene, butadiene-styrene copolymer; polysaccharides such as cellulose, acetyl cellulose, nitrocellulose, starch, calcium alginate, hydroxypropyl methyl cellulose and the like; chitin; chitosan; urushi (Japanese lacquer); polyamides such as gelatin, collagen, keratin and the like; and copolymers of these high molecular materials. These may be a composite compound, and metal oxide particles, glass fiber or the like may be added thereto as occasion demands. Further, an organic compound material may be blended therewith.

Moreover, in the embodiments, a hybridization reaction solution 9 containing a substance derived from a living organism and labeled with a radioactive labeling substance, a substance derived from a living organism and labeled with a labeling substance which generates chemiluminescence emission when it contacts a chemiluminescent substrate and a substance derived from a living organism and labeled with a fluorescent substance such as a fluorescent dye is prepared. However, it is not absolutely necessary for the hybridization reaction solution 9 to contain a substance derived from a living organism and labeled with a radioactive labeling substance, a substance derived from a living organism and labeled with a labeling substance which generates chemiluminescence emission when it contacts a chemiluminescent substrate and a substance derived from a living organism and labeled with a fluorescent substance such as a fluorescent dye but it is sufficient for the hybridization reaction solution 9 to contain at least one of a substance derived from a living organism and labeled with a radioactive labeling substance and a substance derived from a living organism and labeled with a labeling substance which generates chemiluminescence emission when it contacts a chemiluminescent substrate.

Further, in the above described embodiments, specific binding substances are hybridized with substances derived from a living organism and labeled with a radioactive labeling substance, a substance derived from a living organism and labeled with a labeling substance which generates chemiluminescence emission when it contacts a chemiluminescent substrate and a fluorescent substance. However, it is not absolutely necessary to hybridize substances derived from a living organism with specific binding substances and substances derived from a living organism may be specifically bound with specific binding substances by means of antigen-antibody reaction, receptor-ligand reaction or the like instead of hybridization.

Moreover, in the above described embodiments, the scanner shown in FIGS. 6 to 13 is constituted so as to read radiation data of a radioactive labeling substance recorded in a number of the stimulable phosphor layer regions 12 formed in the support 11 of the stimulable phosphor sheet 10 and fluorescence data of a fluorescent substance such as a fluorescent dye recorded in a number of absorptive regions 4 formed in the substrate 2 of the biochemical analysis unit 1, thereby producing biochemical analysis data and includes the first laser stimulating ray source 21 for emitting a laser beam 24 having a wavelength of 640 nm, the second laser stimulating ray source 22 for emitting a laser beam 24 having a wavelength of 532 nm and the third laser stimulating ray source 23 for emitting a laser beam 24 having a wavelength of 473 nm. However, it is not absolutely necessary to read radiation data of a radioactive labeling substance and fluorescence data of a fluorescent substance by a single scanner but radiation data of a radioactive labeling substance and fluorescence data of a fluorescent substance may be read by separate scanners to produce biochemical analysis data. Therefore, it is not absolutely necessary for the scanner to include three laser stimulating ray sources.

Further, in the above described embodiments, the on and off operation of the first laser stimulating ray source 21, the second laser stimulating ray source 22 or the fourth laser stimulating ray source 55 is controlled by the control unit 70 in synchronism with the intermittent movement of the optical head 35. However, if the moving speed of the optical head 35 is determined so that the laser beam 24 quickly passes portions between neighboring stimulable phosphor layer regions 12, 15 of the stimulable phosphor sheet 10, 15 or neighboring absorptive regions 4 of the biochemical analysis unit 1 in the main scanning direction, biochemical analysis data may be produced by merely intermittently moving the optical head 35 while the first laser stimulating ray source 21, the second laser stimulating ray source 22 or the fourth laser stimulating ray source 55 is kept on, thereby sequentially scanning a number of the stimulable phosphor layer regions 12, 17 of the stimulable phosphor sheet 10, 15 or a number of the absorptive regions 4 of the biochemical analysis unit 1 with the laser beam 24 and photoelectrically detecting stimulated emission released from the stimulable phosphor layer regions 12, 17 or fluorescence emission released from the absorptive regions 4.

Furthermore, in the above described embodiments, the scanner shown in FIGS. 6 to 13 includes the first laser stimulating ray source 21 for emitting a laser beam 24 having a wavelength of 640 nm, the second laser stimulating ray source 22 for emitting a laser beam 24 having a wavelength of 532 nm and the third laser stimulating ray source 23 for emitting a laser beam 24 having a wavelength of 473 nm, and the scanner shown in FIGS. 15 to 17 includes the first laser stimulating ray source 21 for emitting a laser beam 24 having a wavelength of 640 nm, the second laser stimulating ray source 22 for emitting a laser beam 24 having a wavelength of 532 nm and the fourth laser stimulating ray source 55 for emitting a laser beam 24 having a wavelength of 980 nm. However, it is not absolutely necessary to employ a laser stimulating ray source as a stimulating ray source and an LED (light emitting diode) light source may be employed as a stimulating ray source instead of a laser stimulating ray source. Further, it is possible to employ a halogen lamp as a stimulating ray source and to provide a spectral filter to cut wavelength components which cannot contribute to the excitation.

Moreover, in the above described embodiments, the scanner shown in FIGS. 6 to 13 and the scanner shown in FIGS. 15 to 17 are constituted so that all of the stimulable phosphor layer regions 12, 17 formed in the support 11 of the stimulable phosphor sheet 10, 15 or all of the absorptive regions 4 formed in the substrate 2 of the biochemical analysis unit 1 are scanned with a laser beam 24 to excite stimulable phosphor or a fluorescent substance such as a fluorescent dye by moving the optical head 35 using a scanning mechanism in the main scanning direction indicated by the arrow X direction and the sub-scanning direction indicated by the arrow Y in FIG. 12. However, all of the stimulable phosphor layer regions 12, 17 formed in the support 11 of the stimulable phosphor sheet 10, 15 or all of the absorptive regions 4 formed in the substrate 2 of the biochemical analysis unit 1 may be scanned with a laser beam 24 to excite stimulable phosphor or a fluorescent substance such as a fluorescent dye by moving the stage 40 in the main scanning direction indicated by the arrow X direction and the sub-scanning direction indicated by the arrow Y in FIG. 12, while holding the optical head 35 stationary, or moving the optical head 35 in the main scanning direction indicated by the arrow X direction or the sub-scanning direction indicated by the arrow Y in FIG. 12 and moving the stage 40 in the sub-scanning direction indicated by the arrow Y or the main scanning direction indicated by the arrow X in FIG. 12.

Further, in the above described embodiments, the scanner shown in FIGS. 6 to 13 and the scanner shown in FIGS. 15 to 17 are constituted so as to photoelectrically detect stimulated emission and fluorescence emission are detected using the photomultiplier 50 as a light detector. However, it is sufficient for the light detector used in the present invention to be able to photoelectrically detect fluorescence emission or stimulated emission and it is possible to employ a light detector such as a line CCD or a two-dimensional CCD instead of the photomultiplier 50.

Furthermore, in the above-described embodiments, a solution containing specific binding substances such as cDNAs are spotted using the spotting device 5 including an injector 6 and a CCD camera 7 so that when the tip end portion of the injector 6 and the center of the absorptive region 4, 84 into which a solution containing specific binding substances is to be spotted are determined to coincide with each other as a result of viewing them using the CCD camera 7, the solution containing the specific binding substances such as cDNA is spotted from the injector 6. However, the solution containing specific binding substances such as cDNAs can be spotted by detecting the positional relationship between a number of the absorptive regions 4, 84 formed in the biochemical analysis unit 1, 80 and the tip end portion of the injector 6 in advance and two-dimensionally moving the biochemical analysis unit 1, 80 or the tip end portion of the injector 6 so that the tip end portion of the injector 6 coincides with each of the absorptive regions 4, 84.

According to the present invention, it is possible to provide a biochemical analysis kit and a method for exposing a stimulable phosphor sheet which can prevent noise caused by the scattering of electron beams (β rays) released from a radioactive labeling substance selectively contained in a plurality of spot-like regions of a biochemical analysis unit from being generated in biochemical analysis data and produce biochemical analysis data having an excellent quantitative characteristic by reading radiation data with high resolution even in the case of forming a plurality of spot-like regions containing specific binding substances, which can specifically bind with a substance derived from a living organism and whose sequence, base length, composition and the like are known, in the biochemical analysis unit at a high density, selectively labeling the plurality of spot-like regions of the biochemical analysis unit with a radioactive labeling substance to record radiation data therein, facing the thus prepared biochemical analysis unit toward a stimulable phosphor layer of a stimulable phosphor sheet to expose the stimulable phosphor layer to a radioactive labeling substance, irradiating the thus exposed stimulable phosphor layer with a stimulating ray, and photoelectrically detecting stimulated emission released from the stimulable phosphor layer to produce biochemical analysis data, and can also prevent noise caused by the scattering of chemiluminescence emission selectively released from a plurality of spot-like regions of a biochemical analysis unit from being generated in biochemical analysis data and produce biochemical analysis data having an excellent quantitative characteristic by reading radiation data with high resolution even in the case of forming a plurality of spot-like regions containing specific binding substances, which can specifically bind with a substance derived from a living organism and whose sequence, base length, composition and the like are known, in the biochemical analysis unit at a high density, selectively labeling the plurality of spot-like regions of the biochemical analysis unit with a labeling substance which generates chemiluminescence emission when it contacts a chemiluminescent substrate to record chemiluminescence data therein, bringing the plurality of spot-like regions of the biochemical analysis unit into contact with a chemiluminescent substrate, thereby causing the plurality of spot-like regions of the biochemical analysis unit to release chemiluminescence emission, facing the biochemical analysis unit releasing chemiluminescence emission toward a stimulable phosphor layer of a stimulable phosphor sheet to expose the stimulable phosphor layer to chemiluminescence emission, irradiating the thus exposed stimulable phosphor layer with a stimulating ray, and photoelectrically detecting stimulated emission released from the stimulable phosphor layer to produce biochemical analysis data.

The invention claimed is:

1. A method for exposing a stimulable phosphor sheet comprising the steps of superposing a biochemical analysis unit including a substrate capable of attenuating radiation energy and formed with a plurality of absorptive regions spaced apart from each other and selectively containing a radioactive labeling substance and a stimulable phosphor sheet including a support formed with a plurality of stimulable phosphor layer regions to be space apart from each other in substantially the same pattern as that of the plurality of absorptive regions formed in the substrate of the biochemical analysis unit and exposing the plurality of stimulable phosphor layer regions of the stimulable phosphor sheet to a radioactive labeling substance selectively contained in the plurality of absorptive regions of the biochemical analysis unit, the plurality of absorptive regions of the biochemical analysis unit and the plurality of stimulable phosphor layer regions of the stimulable phosphor sheet being formed so that an average area Sm of the plurality of absorptive regions of the biochemical analysis unit and an average area Sp of the plurality of stimulable phosphor layer regions of the stimulable phosphor sheet meet a requirement that Sp is equal to or larger than a quarter of Sm.

2. A method for exposing a stimulable phosphor sheet comprising the steps of superposing a biochemical analysis unit including a substrate formed with a plurality of absorptive regions spaced apart from each other, and selectively releasing chemiluminescence emission and a stimulable phosphor sheet including a support formed with a plurality of stimulable phosphor layer regions to be spaced apart from each other in substantially the same pattern as that of the plurality of absorptive regions formed in the substrate of the biochemical analysis unit and exposing the plurality of stimulable phosphor regions of the biochemical analysis unit, the substrate of the biochemical analysis unit being made of a material capable of attenuating light energy, the plurality of stimulable phosphor layer regions of the stimulable phosphor sheet being formed so that an average area Sm of the plurality of absorptive regions of the biochemical analysis unit and an average area Sp of the plurality of stimulable phosphor layer regions of the stimulable phosphor sheet meet a requirement that Sp is equal to or larger than a quarter of Sm.

3. A method for exposing a stimulable phosphor sheet in accordance with claim 1 wherein the plurality of absorptive regions of the biochemical analysis unit and the plurality of stimulable phosphor layer regions of the stimulable phosphor sheet are formed so that an average area Sm of the plurality of absorptive regions of the biochemical analysis unit and an average area Sp of the plurality of stimulable phosphor layer regions off the stimulable phosphor sheet meet a requirement that Sp is equal to or larger than a half of Sm.

4. A method for exposing a stimulable phosphor sheet in accordance with claim 2 wherein the plurality of absorptive regions of the biochemical analysis unit and the plurality of stimulable phosphor layer regions of the stimulable phosphor sheet are formed so that an average area Sm of the plurality of absorptive regions of the biochemical analysis unit and an average area Sp of the plurality of stimulable phosphor layer regions off the stimulable phosphor sheet meet a requirement that Sp is equal to or larger than a half of Sm.

5. A method for exposing a stimulable phosphor sheet in accordance with claim 3 wherein the plurality of absorptive regions of the biochemical analysis unit and the plurality of stimulable phosphor layer regions of the stimulable phosphor sheet are formed so that an average 15 area Sm of the plurality of absorptive regions of the biochemical analysis unit and an average area Sp of the plurality of stimulable phosphor layer regions of the stimulable phosphor sheet meet a requirement that Sp is equal to or larger than Sm.

6. A method for exposing a stimulable phosphor sheet in accordance with claim 4 wherein the plurality of absorptive regions of the biochemical analysis unit and the plurality of stimulable phosphor layer regions of the stimulable phosphor sheet are formed so that an average area Sm of the plurality of absorptive regions of the biochemical analysis unit and an average area Sp of the plurality of stimulable phosphor layer regions of the stimulable phosphor sheet meet a requirement that Sp is equal to or larger than Sm.

7. A method for exposing a stimulable phosphor sheet in accordance with claim 1 wherein the plurality of absorptive regions of the biochemical analysis unit and the plurality of stimulable phosphor layer regions of the stimulable phosphor sheet are formed substantially circular so that an average diameter Dm of the plurality of absorptive regions of the biochemical analysis unit and an average diameter Dp of the plurality of stimulable phosphor layer regions of the stimulable phosphor sheet meet a requirement that Dp is equal to or larger than a half of Dm.

8. A method for exposing a stimulable phosphor sheet in accordance with claim 2 wherein the plurality of absorptive regions of the biochemical analysis unit and the plurality of stimulable phosphor layer regions of the stimulable phosphor sheet are formed substantially circular so that an average diameter Dm of the plurality of absorptive regions of the biochemical analysis unit and an average diameter Dp of the plurality of stimulable phosphor layer regions of the stimulable phosphor sheet meet a requirement that Dp is equal to or larger than a half of Dm.

9. A method for exposing a stimulable phosphor sheet in accordance with claim 7 wherein the plurality of absorptive regions of the biochemical analysis unit and the plurality of stimulable phosphor layer regions of the stimulable phosphor sheet are formed substantially circular so that an average diameter Dm of the plurality of absorptive regions of the biochemical analysis unit and an average diameter Dp of the plurality of stimulable phosphor layer regions of the stimulable phosphor sheet meet a requirement that Dp is equal to or larger than $Dm^{1/2}$.

10. A method for exposing a stimulable phosphor sheet in accordance with claim 8 wherein the plurality of absorptive regions of the biochemical analysis unit and the plurality of stimulable phosphor layer regions of the stimulable phosphor sheet are formed substantially circular so that an average diameter Dm of the plurality of absorptive regions of the biochemical analysis unit and an average diameter Dp of the plurality of stimulable phosphor layer regions of the stimulable phosphor sheet meet a requirement that Dp is equal to or larger than $Dm^{1/2}$.

11. A method for exposing a stimulable phosphor sheet in accordance with claim 9 wherein the plurality of absorptive regions of the biochemical analysis unit and the plurality of stimulable phosphor layer regions of the stimulable phosphor sheet are formed substantially circular so that an average diameter Dm of the plurality of absorptive regions of the biochemical analysis unit and an average diameter Dp of the plurality of stimulable phosphor layer regions of the stimulable phosphor sheet meet a requirement that Dp is equal to or larger than Dm.

12. A method for exposing a stimulable phosphor sheet in accordance with claim 10 wherein the plurality of absorptive regions of the biochemical analysis unit and the plurality of stimulable phosphor layer regions of the stimulable phosphor sheet are formed substantially circular so that an average diameter Dm of the plurality of absorptive regions of the biochemical analysis unit and an average diameter Dp of the plurality of stimulable phosphor layer regions of the stimulable phosphor sheet meet a requirement that Dp is equal to or larger than Dm.

13. A method for exposing a stimulable phosphor sheet in accordance with claim 1 wherein the substrate of the biochemical analysis unit is formed with 10 or more absorptive regions.

14. A method for exposing a stimulable phosphor sheet in accordance with claim 2 wherein the substrate of the biochemical analysis unit is formed with 10 or more absorptive regions.

15. A method for exposing a stimulable phosphor sheet in accordance with claim 1 wherein each of the plurality of absorptive regions formed in the substrate of the biochemical analysis unit has a size of less than 5 mm².

16. A method for exposing a stimulable phosphor sheet in accordance with claim 2 wherein each of the plurality of absorptive regions formed in the substrate of the biochemical analysis unit has a size of less than 5 mm².

17. A method for exposing a stimulable phosphor sheet in accordance with claim 1 wherein the plurality of absorptive regions are formed in the substrate of the biochemical analysis unit at a density of 10 or more per cm².

18. A method for exposing a stimulable phosphor sheet in accordance 10 with claim 2 wherein the plurality of absorptive regions are formed in the substrate of the biochemical analysis unit at a density of 10 or more per cm².

19. A method for exposing a stimulable phosphor sheet in accordance with claim 1 wherein the plurality of absorptive regions are formed by charging an absorptive material in a plurality of holes formed in the substrate of the biochemical analysis unit.

20. A method for exposing a stimulable phosphor sheet in accordance with claim 2 wherein the plurality of absorptive regions are formed by charging an absorptive material in a plurality of holes formed in the substrate of the biochemical analysis unit.

21. A method for exposing a stimulable phosphor sheet in accordance with claim 1 wherein the substrate of the biochemical analysis unit has a property of reducing the energy of radiation and/or the energy of light to ⅕ or less when the radiation and/or light travels in the substrate by a distance equal to that between neighboring absorptive layers.

22. A method for exposing a stimulable phosphor sheet in accordance with claim 2 wherein the substrate of the biochemical analysis unit has a property of reducing the energy of radiation and/or the energy of light to ⅕ or less when the radiation and/or light travels in the substrate by a distance equal to that between neighboring absorptive layers.

23. A method for exposing a stimulable phosphor sheet in accordance with claim 1 wherein the substrate of the biochemical analysis unit is made of a material selected from a group consisting of a metal material, a ceramic material and a plastic material.

24. A method for exposing a stimulable phosphor sheet in accordance with claim 2 wherein the substrate of the biochemical analysis unit is made of a material selected from a group consisting of a metal material, a ceramic material and a plastic material.

25. A method for exposing a stimulable phosphor sheet in accordance with claim 1 wherein the substrate of the biochemical analysis unit is made of a porous carbon material or a porous material capable of a membrane filter.

26. A method for exposing a stimulable phosphor sheet in accordance with claim 2 wherein the substrate of the biochemical analysis unit is made of a porous carbon material or a porous material capable of a membrane filter.

27. A method for exposing a stimulable phosphor sheet in accordance with claim 1 wherein the substrate of the biochemical analysis unit is made of a bundle of a plurality of fibers.

28. A method for exposing a stimulable phosphor sheet in accordance with claim 2 wherein the substrate of the biochemical analysis unit is made of a bundle of a plurality of fibers.

29. A method for exposing a stimulable phosphor sheet in accordance with claim 1 wherein specific binding substances whose sequence, base length, composition and the like are known are absorbed in the plurality of absorptive regions of the biochemical analysis unit and the plurality of absorptive regions of the biochemical analysis unit are selectively labeled with a radioactive labeling substance by selectively specifically binding a substance derived from a living organism and labeled with the radioactive labeling substance with the specific binding substances absorbed in the plurality of absorptive regions of the biochemical analysis unit.

30. A method for exposing a stimulable phosphor sheet in accordance with claim 2 wherein specific binding substances whose sequence, base length, composition and the like are known are absorbed in the plurality of absorptive regions of the biochemical analysis unit and the plurality of absorptive regions of the biochemical analysis unit are selectively labeled with a labeling substance which generates chemiluminescence emission when it contacts a chemiluminescent substrate by selectively specifically binding a substance derived from a living organism and labeled with the labeling substance which generates chemiluminescence emission when it contacts a chemiluminescent substrate with the specific binding substances absorbed in the plurality of absorptive regions of the biochemical analysis unit.

31. A method for exposing a stimulable phosphor sheet in accordance with claim 1 wherein the plurality of stimulable phosphor layer regions of the stimulable phosphor sheet are formed by charging stimulable phosphor in a plurality of holes formed in the support of the stimulable phosphor sheet.

32. A method for exposing a stimulable phosphor sheet in accordance with claim 2 wherein the plurality of stimulable phosphor layer regions of the stimulable phosphor sheet are formed by charging stimulable phosphor in a plurality of holes formed in the support of the stimulable phosphor sheet.

33. A method for exposing a stimulable phosphor sheet in accordance with claim 1 wherein the support of the stimulable phosphor sheet is capable of attenuating radiation energy and/or light energy.

34. A method for exposing a stimulable phosphor sheet in accordance with claim 2 wherein the support of the stimulable phosphor sheet is capable of attenuating radiation energy and/or light energy.

35. A method for exposing a stimulable phosphor sheet in accordance with claim 1 wherein the support of the stimulable phosphor sheet has a property of reducing the energy of radiation and/or the energy of light to $1/5$ or less when the radiation and/or light travels in the support by a distance equal to that between neighboring stimulable phosphor layer regions.

36. A method for exposing a stimulable phosphor sheet in accordance with claim 2 wherein the support of the stimulable phosphor sheet has a property of reducing the energy of radiation and/or the energy of light to $1/5$ or less when the radiation and/or light travels in the support by a distance equal to that between neighboring stimulable phosphor layer regions.

37. A method for exposing a stimulable phosphor sheet in accordance with claim 1 wherein the support of the stimulable phosphor sheet is made of a material selected from a group consisting of a metal material, a ceramic material and a plastic material.

38. A method for exposing a stimulable phosphor sheet in accordance with claim 2 wherein the support of the stimulable phosphor sheet is made of a material selected from a group consisting of a metal material, a ceramic material and a plastic material.

\* \* \* \* \*